(12) United States Patent
Levner et al.

(10) Patent No.: US 11,248,203 B2
(45) Date of Patent: *Feb. 15, 2022

(54) OPEN-TOP MICROFLUIDIC DEVICE WITH STRUCTURAL ANCHORS

(71) Applicant: EMULATE, INC., Boston, MA (US)

(72) Inventors: Daniel Levner, Brookline, MA (US); Christopher David Hinojosa, Cambridge, MA (US); Norman Wen, West Roxbury, MA (US); Antonio Varone, West Roxbury, MA (US); Justin Nguyen, Medford, MA (US); Lina Williamson, Chapel Hill, NC (US); S. Jordan Kerns, Reading, MA (US); Catherine Karalis, Brookline, MA (US); Geraldine Hamilton, Cambridge, MA (US); Carol Lucchesi, Westwood, MA (US)

(73) Assignee: EMULATE, INC, Boston, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/160,617

(22) Filed: Jan. 28, 2021

(65) Prior Publication Data
US 2021/0214670 A1  Jul. 15, 2021

Related U.S. Application Data

(62) Division of application No. 15/781,370, filed as application No. PCT/US2016/064814 on Dec. 2, 2016, now Pat. No. 10,961,496.

(60) Provisional application No. 62/263,492, filed on Dec. 4, 2015.

(51) Int. Cl.
| | |
|---|---|
| *C12M 3/06* | (2006.01) |
| *C12M 1/12* | (2006.01) |
| *C12M 1/00* | (2006.01) |
| *C12M 1/42* | (2006.01) |
| *G01N 33/50* | (2006.01) |
| *G01N 33/543* | (2006.01) |
| *C12N 5/0793* | (2010.01) |
| *C12N 5/079* | (2010.01) |
| *C12N 5/071* | (2010.01) |
| *C12N 5/077* | (2010.01) |

(52) U.S. Cl.
CPC ............ *C12M 35/04* (2013.01); *C12M 23/16* (2013.01); *C12M 23/38* (2013.01); *C12M 25/02* (2013.01); *C12M 35/08* (2013.01); *C12N 5/069* (2013.01); *C12N 5/0619* (2013.01); *C12N 5/0622* (2013.01); *C12N 5/0629* (2013.01); *C12N 5/0656* (2013.01); *C12N 5/0688* (2013.01); *C12N 5/0697* (2013.01); *C12N 5/0698* (2013.01); *G01N 33/50* (2013.01); *G01N 33/5082* (2013.01); *G01N 33/54366* (2013.01); *C12N 2501/165* (2013.01)

(58) Field of Classification Search
CPC .. C12N 5/0656; C12N 5/0698; C12N 5/0622; C12N 5/0629; C12N 5/0688; C12N 5/069; C12N 2501/165; C12N 5/0619; C12N 5/0697; B01L 3/502761; B01L 3/502715; B01L 2300/0645; B01L 2300/0887; B01L 2200/0668; B01L 2300/0681; C12M 25/02; C12M 35/04; C12M 23/16; C12M 23/38; C12M 35/08; G01N 33/5082; G01N 33/50; G01N 33/54366

See application file for complete search history.

(56) References Cited

U.S. PATENT DOCUMENTS

| | | | |
|---|---|---|---|
| 8,647,861 B2 | 2/2014 | Ingber et al. | 435/289.1 |
| 2003/0120471 A1 | 6/2003 | Izmailov et al. | 703/11 |
| 2007/0141552 A1 | 6/2007 | Warren et al. | 424/93.1 |
| 2012/0034677 A1 | 2/2012 | Delamarche et al. | 435/305.1 |
| 2012/0135452 A1 | 5/2012 | Shuler et al. | 435/382 |
| 2012/0164679 A1 | 6/2012 | Vrouwe et al. | 435/29 |
| 2012/0195810 A1 | 8/2012 | Cohen et al. | 422/502 |
| 2012/0322097 A1 | 12/2012 | Charest et al. | 435/293.1 |
| 2013/0203086 A1 | 8/2013 | Achyuta et al. | 435/7.92 |
| 2014/0038279 A1 | 2/2014 | Ingber et al. | 435/297.2 |
| 2014/0057311 A1 | 2/2014 | Kamm et al. | 435/29 |
| 2014/0093905 A1 | 4/2014 | Ingber et al. | 435/289.1 |
| 2014/0349396 A1 | 11/2014 | West et al. | 435/366 |
| 2015/0004077 A1 | 1/2015 | Wikswo et al. | 422/502 |
| 2015/0111239 A1 | 4/2015 | Collins et al. | 436/180 |
| 2015/0218502 A1 | 8/2015 | Vanzieleghem et al. | 422/502 |

FOREIGN PATENT DOCUMENTS

| | | |
|---|---|---|
| WO | WO/2014/197999 | 12/2014 |
| WO | WO/2015/006751 | 1/2015 |
| WO | WO/2015/138032 | 9/2015 |
| WO | WO/2015/138034 | 9/2015 |

OTHER PUBLICATIONS

Bhatia, S. N. et al. (2014) "Microfluidic organs-on-chips," *Nature Biotechnology* 32(8), 760-772.
Huh, D. et al. (2010) "Reconstituting Organ-Level Lung Functions on a Chip," *Science* 328(5986), 1662.
Wagner, I. et al. (2013) "A dynamic multi-organ-chip for long-term cultivation and substance testing proven by 3D human liver and skin tissue co-culture," *Lab on a Chip* 13(18), 3538-3547.
PCT International Search Report of International Application No. PCT/US2016/064814 dated Feb. 7, 2017.
Australian Examiner Report for Application No. 2016363000 dated Oct. 2, 2019.

(Continued)

*Primary Examiner* — Satyendra K Singh
(74) *Attorney, Agent, or Firm* — Medlen & Carroll, LLP

(57) ABSTRACT

A microfluidic device is contemplated comprising an open-top cavity with structural anchors on the vertical wall surfaces that serve to prevent gel shrinkage-induced delamination, a porous membrane (optionally stretchable) positioned in the middle over a microfluidic channel(s). The device is particularly suited to the growth of cells mimicking dermal layers.

13 Claims, 49 Drawing Sheets

(56) References Cited

OTHER PUBLICATIONS

Temiz, Y. et al. (2015) "Lab-on-a-chip devices: How to close and plug the lab?," *Microelectronic Engineering 132*, 156-175.
Australian Examiner Report for Application No. 2020202721 dated Nov. 26, 2020.

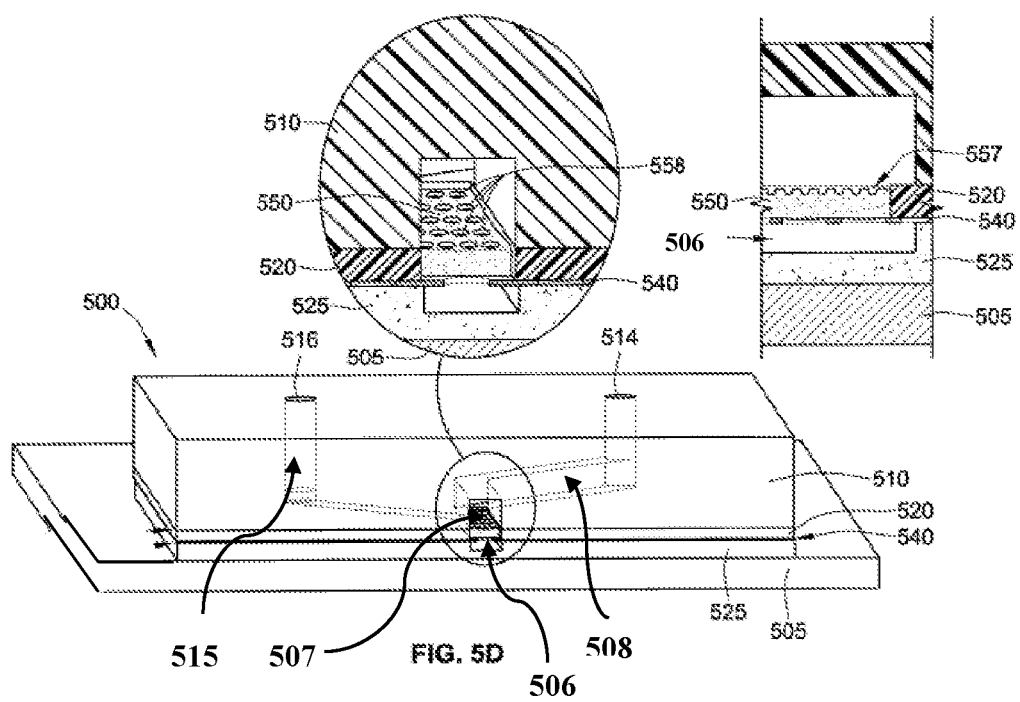

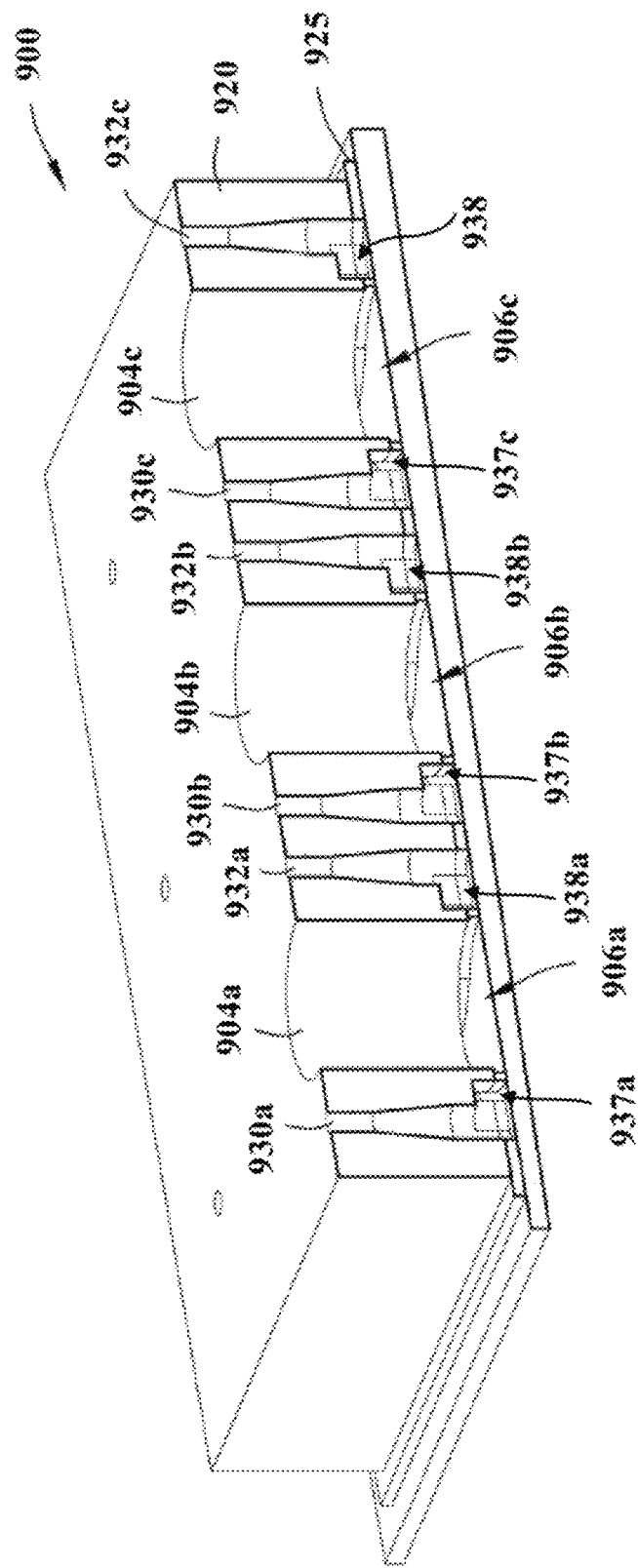

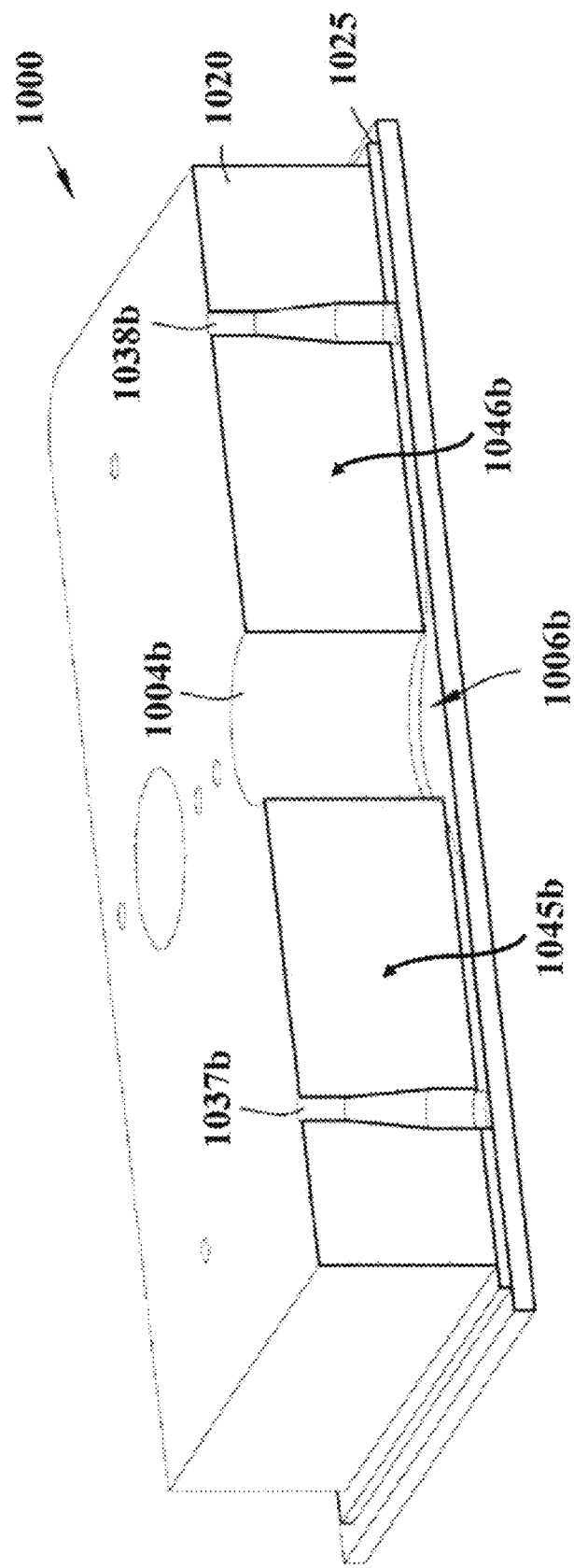

OPEN-TOP MICROFLUIDIC DEVICE WITH STRUCTURAL ANCHORS

CROSS-REFERENCE TO RELATED APPLICATIONS

This application is a Divisional of, and claims priority to, co-pending U.S. patent application Ser. No. 15/781,370, filed Jun. 4, 2018; which claims priority to PCT/US2016/064814, filed Dec. 2, 2016; which claims priority to Provisional Application Ser. No. 62/263,492 filed on Dec. 4, 2015, the contents of which are incorporated herein in their entirety.

FIELD OF THE INVENTION

A microfluidic device is contemplated comprising an open-top cavity with structural anchors on the vertical wall surfaces that serve to prevent gel shrinkage-induced delamination, a porous membrane (optionally stretchable) positioned in the middle over a microfluidic channel(s).

BACKGROUND

In vitro models involving thick gels, i.e. >0.2 mm in thickness (and more typically >0.5 mm in thickness), have a common problem of shrinkage due to evaporation of water and tissue-induced stresses, which cause delamination from surfaces containing the gel. This issue prevents robust implementation of 3D gels with microfluidic systems, which can introduce physiologically relevant shear forces and concentration gradients. In addition, such delamination will prevent any attempt to apply mechanical forces, for example stretching or compressing, on the gel itself.

3D gel in vitro models are currently performed in tranwells or well plates, where shrinkage-induced delamination is not important. Prior art solutions to gel shrinkage include transplanting the 3D gel post-shrinking, and pre-compressing the gel, both of which are equivalent to pre-shrinking the gel before its use. Past microfluidic systems that include mechanical stretching focused on stretching a thin membrane as opposed to uniformly stretching a thick (>0.5 mm) gel.

SUMMARY OF THE INVENTION

A microfluidic device is contemplated comprising an open-top cavity with structural anchors on the vertical wall surfaces that serve to prevent gel shrinkage-induced delamination, a porous membrane (optionally stretchable) positioned in the middle over a microfluidic channel(s). By preventing delamination, this allows for implementation of 3D gels with microfluidic systems. The device is particularly suited to the growth of cells mimicking dermal layers, allowing for the testing of cosmetics and candidate drugs (including aerosols).

In one embodiment, the present invention contemplates making measurements relating to electrophysiology of cells in an open-top chip. It is not intended that the present invention be limited by the type of cells; a variety of excitable cells is contemplated. Moreover, such measurements can be done whether the open-top chip comprises a gel or not. In one embodiment, the present invention contemplates a device, comprising a first structure defining a first chamber, the first chamber comprising an open top surface region; a second chamber, wherein a first interface region is formed between the first chamber and the second chamber; a membrane disposed at the first interface region, the membrane including a first side facing the first chamber and a second side facing the second chamber; one or more cells disposed in at least one of the first chamber and the second chamber; and one or more electrodes. In one embodiment, at least one of the first chamber and second chamber comprises a fluidic channel. In one embodiment, at least one of the one or more electrodes is disposed in physical contact with said membrane. In one embodiment, said performing an electrophysiological measurement comprises performing a patch-clamp measurement. In one embodiment, said device further comprises a cover disposed on top of at least part of the said open top surface region, and wherein at least one of the one or more electrodes is disposed in physical contact with the cover. In one embodiment, at least one of the one or more electrodes is present within the first chamber and crosses the open top surface region. While not intending to be limited to the cell type, in one embodiment, said cells comprise at least one of neurons and astrocytes. In another embodiment, said cells comprise at least one of retinal rods and retinal cones. In one embodiment, said cells comprise at least one of skeletal muscle, smooth muscle and cardiac muscle.

The present invention also contemplates, in one embodiment, a layered structure comprising i) fluidic channels covered by ii) a porous membrane, said membrane comprising iii) a layer of cells and said membrane positioned below iv) a gel matrix. In one embodiment, there is a removable cover over the gel matrix (and/or cells). While not intending to be limited to any particular cell type, in one embodiment, the cells are brain microvascular endothelial cells. In one embodiment of the layered structure, it further comprises neurons on, in or under the gel matrix. In still another embodiment of the layered structure, it further comprises astrocytes on, in or under the gel matrix. Cells can be positioned in various different places (in or on the layered structure). In one embodiment, the layer of brain microvascular endothelial cells is positioned on the bottom of the membrane so as to be in contact with the fluidic channels. It is not intended that the present invention be limited to any particular source of cells. In one embodiment, the brain microvascular endothelial cells are primary cells.

It is not intended that the present invention be limited to embodiments with only one gel or gel layer. In one embodiment, the layered structure further comprises a second gel matrix (e.g. positioned under said membrane).

The gel(s) or coatings can be patterned or not patterned. Moreover, when patterned, the pattern need not extend to the entire surface. For example, in one embodiment, at least a portion of said gel matrix is patterned.

To make measurements, electrodes can be included in the layered structure, i.e. electrodes configured for measuring the electrophysiology of cells, such as brain microvascular endothelial cells. Other cells can also be tested (e.g. muscle cells).

It is not intended that the present invention be limited by the nature or components of the gel matrix or gel coating. In one embodiment, gel matrix comprises collagen. A variety of thickness is contemplated. In one embodiment of the layered structure, said gel matrix is between 0.2 and 6 mm in thickness.

In yet another embodiment, the present invention contemplates a microfluidic device comprising i) a chamber, said chamber comprising a lumen and projections in the lumen, said lumen comprising ii) a gel matrix anchored by said projections, said gel matrix positioned above iii) a porous membrane, said membrane in contact with iv) fluidic channels. In one embodiment, said membrane comprises cells. The projections serve as anchors for the gel. The projections, in one embodiment, project outward from the side walls. The projections, in another embodiment, project upward. The projects, in another embodiment, project downward. The projections can take a number of forms (e.g. a T structure, a Y structure, a structure with straight or curving edges, etc.). In some embodiments, there are two or more projections; in other embodiments, there are four or more projections to anchor the gel matrix. In one embodiment, the membrane is above said fluidic channels. In one embodiment the cells comprise a layer of brain microvascular endothelial cells (BMECs). In one embodiment, the BMECs are positioned on the bottom of the membrane so as to be in contact with the fluidic channels. In one embodiment, it further comprises neurons on, in or under the gel matrix. In one embodiment, it further comprises a second gel matrix (e.g. positioned under said membrane). While not limited to the nature or source of the cells, in one embodiment, the brain microvascular endothelial cells are primary cells. In one embodiment, it further comprises pericytes on, in or under the gel matrix. In one embodiment, said gel matrix is under a removable cover. In one embodiment, said gel matrix is patterned (or at least a portion of it is patterned). In one embodiment, the device further comprises electrodes, e.g. electrodes are configured for measuring the electrophysiology of said brain microvascular endothelial cells. In one embodiment, said gel matrix comprises collagen. In one embodiment, said collagen matrix is between 0.2 and 6 mm in thickness.

The present invention also contemplates, in one embodiment, a method of testing, comprising 1) providing a layered structure comprising i0 fluidic channels covered by ii) a porous membrane, said membrane comprising iii) a layer of cells in contact with said fluidic channels, said membrane positioned below iv) a gel matrix, said gel matrix under a removable cover; and 2) measuring the electrophysiology of said cells. A variety of cell types can be tested. In one embodiment, the cells are brain microvascular endothelial cells. In another embodiment, the cells are muscle cells. In one embodiment of this method, the layered structure further comprises v) electrodes configured for measuring the electrophysiology of said brain microvascular endothelial cells. In one embodiment, said measuring comprises TEER measurements with said electrodes. In one embodiment, said TEER measurements indicate tight cell-to-cell junctions between said brain microvascular endothelial cells. In another embodiment, said measuring of step 2) comprises patch clamp measurements, extracellular electrophysiology measurements, imaging using calcium-sensitive dyes or proteins, or imaging using voltage-sensitive dyes or proteins. In one embodiment, said brain microvascular endothelial cells express the marker Glut 1. In one embodiment of this method, said layered structure further comprises neurons on, in or under said gel matrix. In one embodiment, the layered structure further comprises a second gel matrix positioned under said membrane.

The present invention contemplates a variety of uses for these devices and methods. In one embodiment, the present invention contemplates a method of topically testing an agent (whether a drug, food, gas, or other substance) comprising 1) providing a) an agent and b) microfluidic device comprising i) a chamber, said chamber comprising a lumen and projections into the lumen, said lumen comprising ii) a gel matrix anchored by said projections and comprising cell in, on or under said gel matrix, said gel matrix positioned above iii) a porous membrane and under iv) a removable cover, said membrane comprising brain microvascular endothelial cells in contact with v) fluidic channels; 2) removing said removable cover; and 3) topically contacting said cells in, on or under said gel matrix with said agent. In one embodiment, said agent is in an aerosol. In one embodiment, agent is in a liquid, gas, gel, semi-solid, solid, or particulate form.

The present invention also contemplates a skin model in the form of a microfluidic device or layered structure. In one embodiment, the present invention contemplates a device or layered structure comprising i) fluidic channels covered by ii) a porous membrane, said membrane comprising iii) a layer of endothelial cells and said membrane positioned below iv) a gel matrix comprising fibroblasts and keratinocytes. In one embodiment, the gel matrix (and or cells) is covered by a removable cover. In one embodiment, the fibroblasts are within the gel matrix and the keratinocytes are on top of the gel matrix. In one embodiment, the keratinocytes comprise more than one layer on top of the gel matrix.

In one embodiment, the present invention contemplates a microfluidic device comprising i) a chamber, said chamber comprising a lumen and projections into the lumen, said lumen comprising ii) a gel matrix anchored by said projections, said gel matrix comprising fibroblasts and keratinocytes, said gel matrix positioned above iii) a porous membrane, said membrane comprising endothelial cells in contact with iv) fluidic channels. In one embodiment, the gel matrix (and/or cells) is covered by a removable cover. In one embodiment, the membrane is above said fluidic channels and wherein the layer of endothelial cells is positioned on the bottom of the membrane so as to be in contact with the fluidic channels. In one embodiment, the fibroblasts are within the gel matrix and the keratinocytes are on top of the gel matrix.

The present invention contemplates, in one embodiment, a method of treating endothelial cells, comprising 1) providing a) an angiogenic or arteriogenic growth factor in solution, b) a layered structure comprising i) fluidic channels covered by ii) a porous membrane, said membrane comprising iii) a layer of endothelial cells in contact with said fluidic channels, said membrane position below iv) a gel matrix comprising fibroblasts and keratinocytes; and 2) introducing said solution into said fluidic channels comprising said angiogenic or arteriogenic growth factor so as to treat said endothelial cells. In one embodiment, the gel matrix (and/or cells) is covered by a removable cover. In one embodiment, prior to said introducing of step 2), the cover is removed.

The present invention also contemplates, in one embodiment, a method of testing a drug or other agent on keratinocytes, comprising 1) providing a) a candidate drug and b) microfluidic device comprising i) a chamber, said chamber comprising a lumen and projections into the lumen, said lumen comprising ii) a gel matrix anchored by said projections, said gel matrix comprising fibroblasts and keratinocytes, said gel matrix positioned above iii) a porous membrane, said membrane comprising endothelial cells in contact with iv) fluidic channels; and 2) contacting said keratinocytes with said candidate drug. In one embodiment, the gel matrix (and or cells) is covered by a removable cover. In one embodiment, prior to said contacting of step 2), said cover is removed. In one embodiment, the agent or drug is in the form of an aerosol.

The present invention also contemplates, in one embodiment, microfluidic device for simulating a function of a tissue, comprising: a first structure defining a first chamber, the first chamber comprising a gel disposed therein and including an opened region, said gel comprising intestinal epithelial cells in or on said gel; a second structure defining a second chamber; and a membrane located at an interface region between the first chamber and the second chamber, the membrane including a first side facing toward the first chamber and a second side facing toward the second chamber, said second side comprising living endothelial cells. In one embodiment, the gel has a patterned surface.

The present invention also contemplates, in one embodiment, a microfluidic device for simulating a function of a tissue, comprising: a first structure defining a first chamber, the first chamber comprising a gel disposed therein and including an opened region, said gel comprising muscle cells in or on said gel; a second structure defining a second chamber; and a membrane located at an interface region between the first chamber and the second chamber, the membrane including a first side facing toward the first chamber and a second side facing toward the second chamber. In one embodiment, the gel has a patterned surface.

In one embodiment, the present invention contemplates a device comprising i) a chamber, said chamber comprising a non-linear lumen, said lumen comprising ii) a gel matrix, said gel matrix positioned above iii) a porous membrane, said membrane positioned above one or more iv) fluidic channels. In one embodiment, the fibroblasts are within the gel matrix and keratinocytes are on top of the gel matrix. In one embodiment, the keratinocytes comprise more than one layer on top of the gel matrix. In one embodiment, the layer of endothelial cells is positioned on the bottom of the membrane so as to be in contact with the fluidic channels. In one embodiment, the endothelial cells are primary cells. In one embodiment, the primary cells are small vessel human dermal microvascular endothelial cells. In one embodiment, the primary cells are human umbilical vein endothelial cells. In one embodiment, the primary cells are bone marrow-derived endothelial progenitor cells. In one embodiment, the keratinocytes are epidermal keratinocytes. In one embodiment, the non-linear lumen is circular. In one embodiment, the device further comprises a removable cover. In one embodiment, the device is a microfluidic device and said fluidic channels are microfluidic channels.

In one embodiment, the present invention contemplates a microfluidic device comprising i) a chamber, said chamber comprising a circular lumen, said lumen comprising ii) a gel matrix comprising fibroblasts and keratinocytes, said gel matrix positioned above iii) a porous membrane, said membrane comprising endothelial cells in contact with iv) microfluidic channels. In one embodiment, the membrane is above said fluidic channels and wherein the layer of endothelial cells is positioned on the bottom of the membrane so as to be in contact with the fluidic channels. In one embodiment, the fibroblasts are within the gel matrix and the keratinocytes are on top of the gel matrix. In one embodiment, the keratinocytes comprise more than one layer on top of the gel matrix. In one embodiment, the endothelial cells are primary cells. In one embodiment, the primary cells are small vessel human dermal microvascular endothelial cells. In one embodiment, the primary cells are human umbilical vein endothelial cells. In one embodiment, the primary cells are bone marrow-derived endothelial progenitor cells. In one embodiment, the keratinocytes are epidermal keratinocytes. In one embodiment, the keratinocytes are human foreskin keratinocytes. In one embodiment, the matrix comprises collagen. In one embodiment, the collagen matrix is between 0.2 and 6 mm in thickness.

In one embodiment, the present invention contemplates a method of treating endothelial cells, comprising 1) providing a) an angiogenic or arteriogenic growth factor in solution, b) a layered structure comprising i) fluidic channels covered by ii) a porous membrane, said membrane comprising iii) a layer of endothelial cells in contact with said fluidic channels, said membrane position below iv) a gel matrix comprising fibroblasts and keratinocytes; and 2) introducing said solution into said fluidic channels comprising said angiogenic or arteriogenic growth factor so as to treat said endothelial cells. In one embodiment, the gel matrix comprises collagen. In one embodiment, the collagen matrix is between 0.2 and 6 mm in thickness.

In one embodiment, the present invention contemplates a fluidic cover comprising a fluidic channel, said fluidic cover configured to engage a microfluidic device. In one embodiment, the microfluidic device comprises an open chamber, and wherein said fluidic cover configured to cover and close said open chamber. In one embodiment, the fluidic cover further comprises one or more electrodes.

In one embodiment, the present invention contemplates an assembly comprising a fluidic cover comprising a fluidic channel, said fluidic cover detachably engaged with a microfluidic device. In one embodiment, the microfluidic device comprises an open chamber, and wherein said fluidic cover configured to cover and close said open chamber. In one embodiment, the open chamber comprises a non-linear lumen. In one embodiment, the non-linear lumen is circular. In one embodiment, the fluidic cover further comprises one or more electrodes.

In one embodiment, the present invention contemplates a method of making an assembly, comprising: a) providing a fluidic cover comprising a fluidic channel, said fluidic cover configured to engage b) a microfluidic device, said microfluidic device comprises an open chamber, and wherein said fluidic cover configured to cover and close said open chamber; and b) detachably engaging said microfluidic device with said fluidic cover so as to make an assembly. In one embodiment, the open chamber comprises a non-linear lumen. In one embodiment, the non-linear lumen is circular. In one embodiment, the fluidic cover further comprises one or more electrodes.

In one embodiment, the present invention contemplates a microfluidic device comprising i) a chamber, said chamber comprising a lumen, said lumen comprising ii) a gel matrix comprising at least one of neurons and astrocytes, said gel matrix positioned above iii) a porous membrane, said membrane comprising brain microvascular endothelial cells in contact with iv) microfluidic channels. In one embodiment, the neurons are on, in or under the gel matrix. In one embodiment, the astrocytes are on, in or under the gel matrix.

DESCRIPTION OF THE FIGURES

FIG. 5D illustrates a perspective view of the exemplary open-top microfluidic device of FIG. 5C including a patterned gel in the opened region of the top structure and a removable cover disposed above the top structure according to embodiments of the present disclosure.

FIGS. 9 and 10 illustrate exemplary perspective views of cross-sections through the stretchable open-top microfluidic device of FIG. 8A.

It is not intended that the figures be limiting. The open-top cavity/chamber can have various geometries other than the one depicted above: e.g. oval, rectangular slot, ellipse. Structural anchors can have various geometries other than the one depicted above. For example, they can have different 'head' geometries and sizes.

Figure 20A:
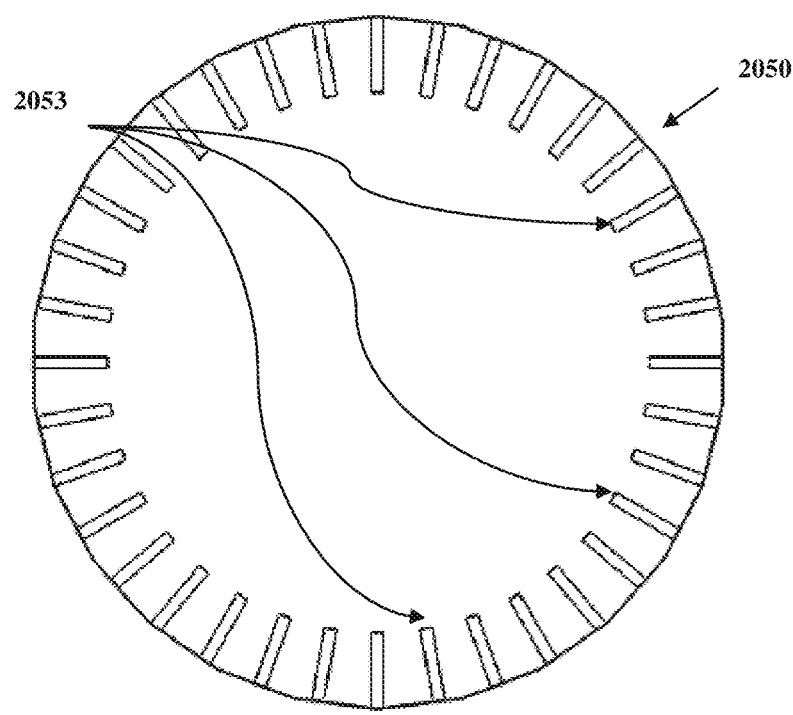
Figure 20B:
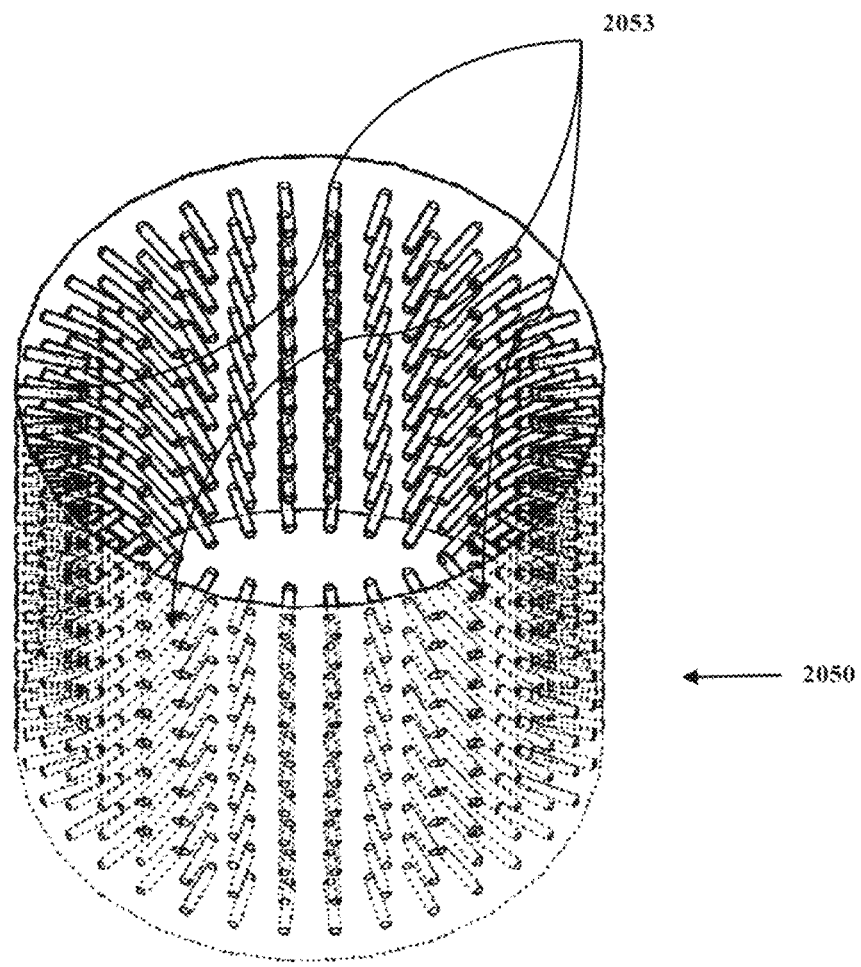
Figure 21A:
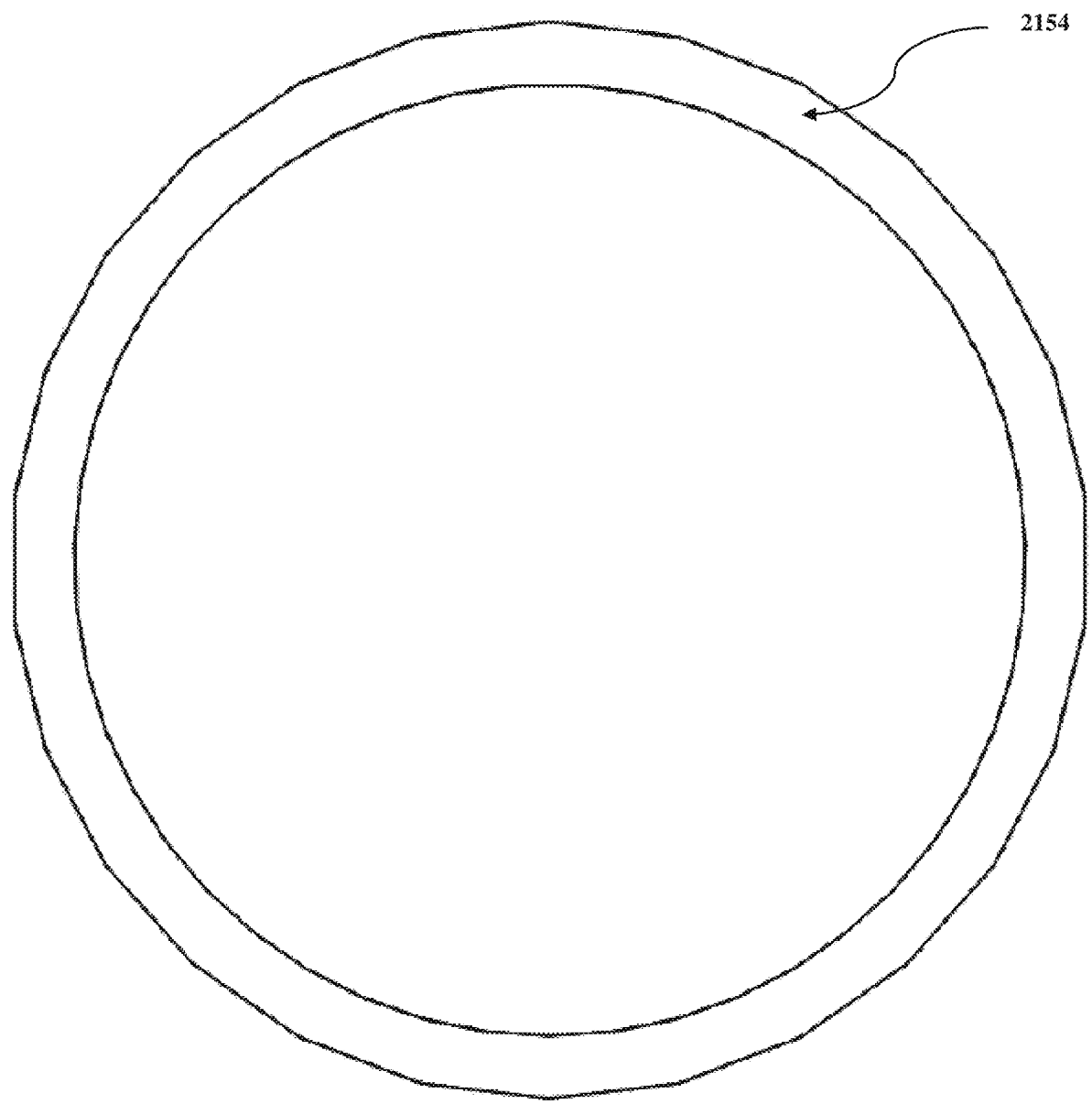
Figure 21B:
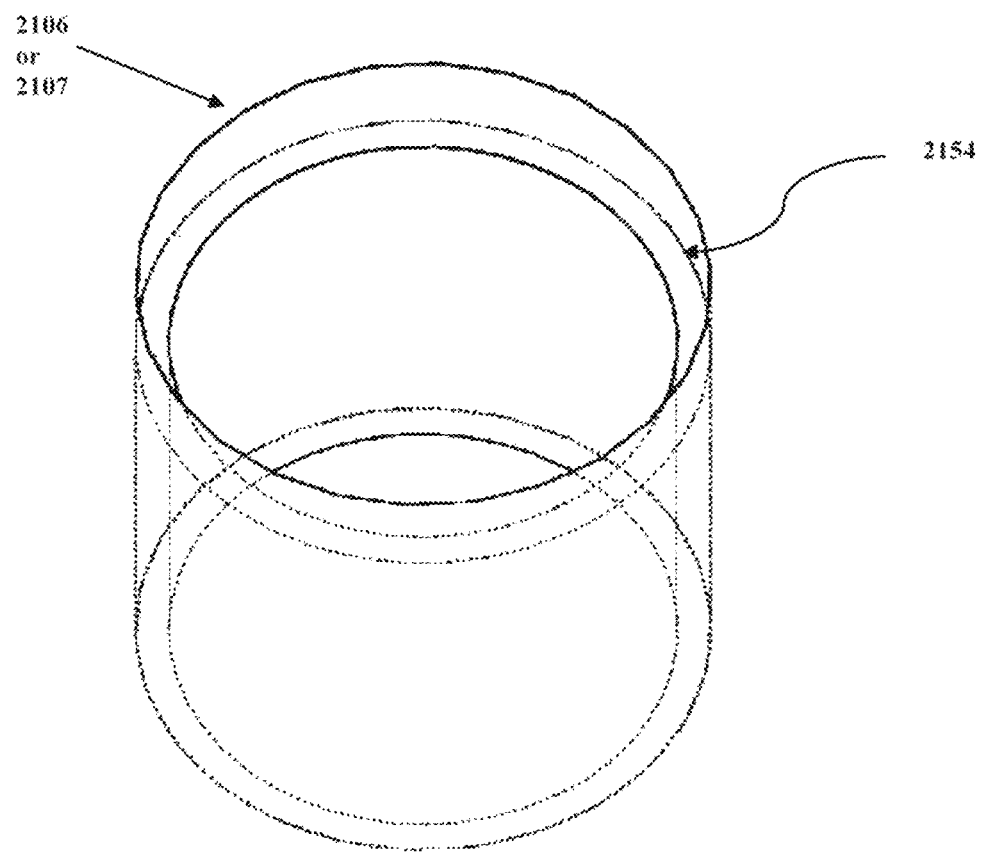

Alternatively, the gel can be maintained with a mesh wall or micro-pillar array. FIG. 20A-B shows a top view and elevated side view of one embodiment of a micro-pillar array. FIG. 21A-B shows a top view and elevated side view of one embodiment of a mesh wall or insert.

Figure 22:
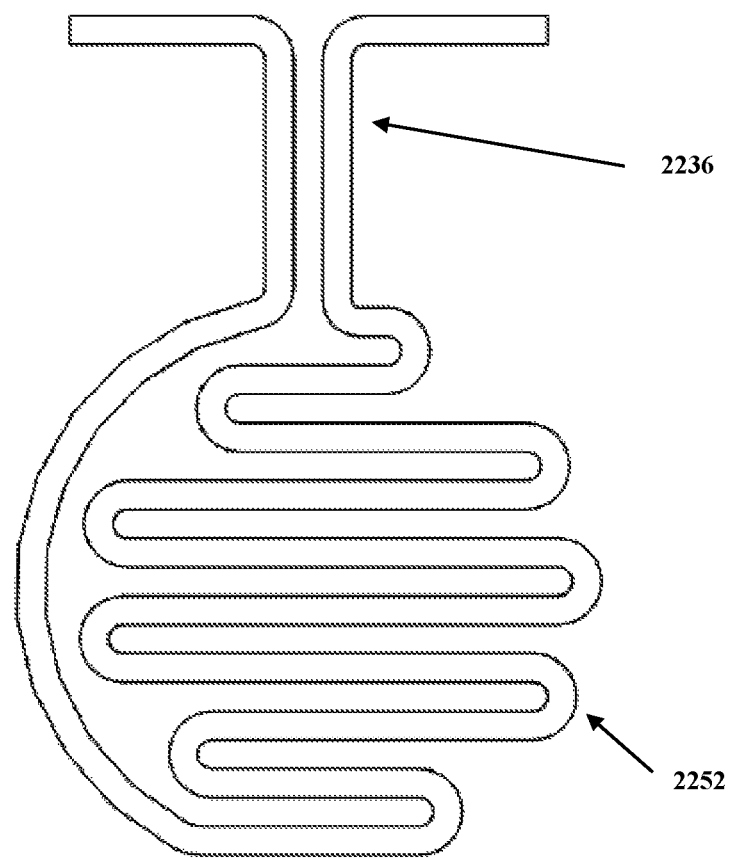

The bottom-layer microfluidics can have various channel geometries other than the one depicted above, i.e. the channel height, channel width, and channel path geometry can be changed. FIG. 22 shows a different design for the microfluidic channels.

FIGS. 23-26 show various embodiments for microfluidic devices as contemplated herein that are configured for electrophysiological measurements (e.g., for example, patch clamp measurements using transepithelial electric resistance (TEER).

Figure 13:
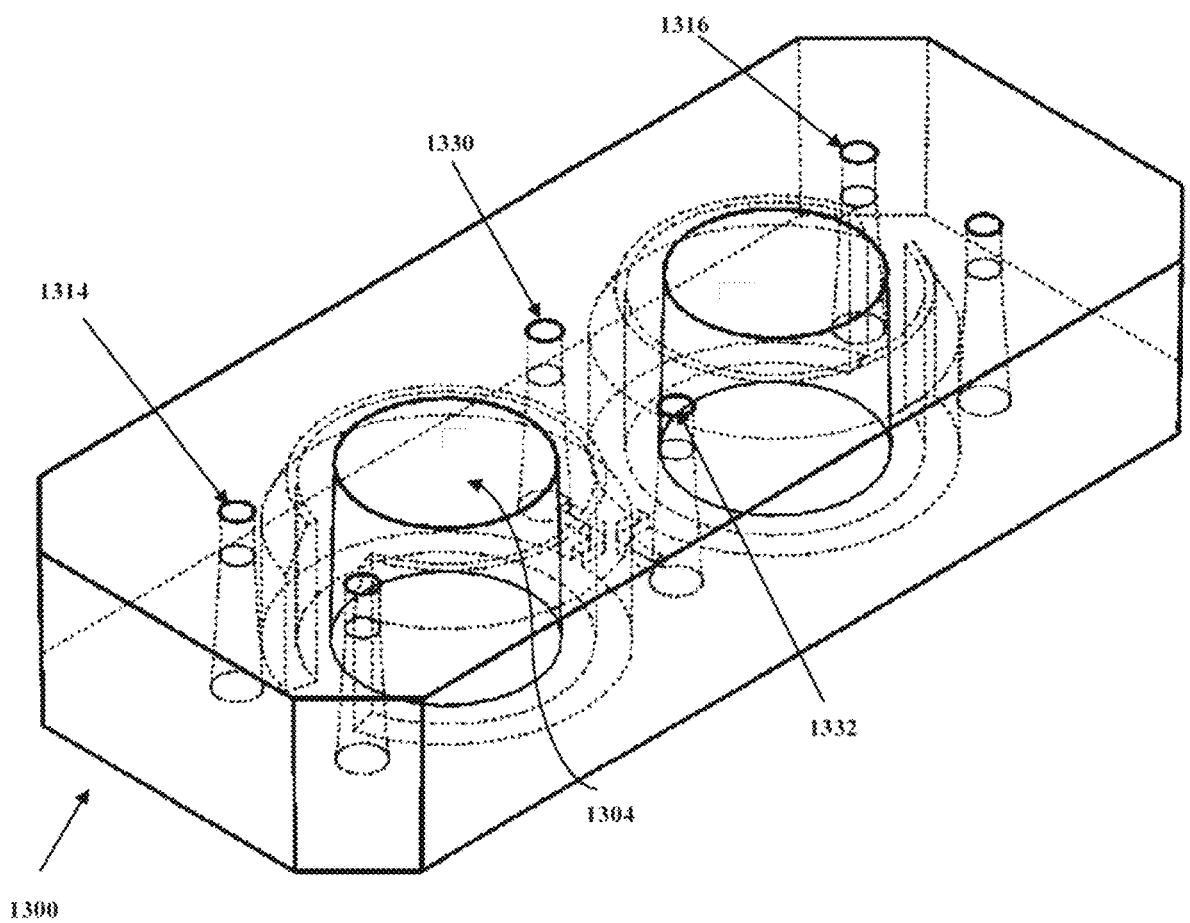
FIG. 13 shows one plan view embodiment of a device comprising more than one open-top cavity or chamber, which allows for direct gel dispensing, cell seeding, and treatments (including treatment with aerosols and topicals).
Figure 27:
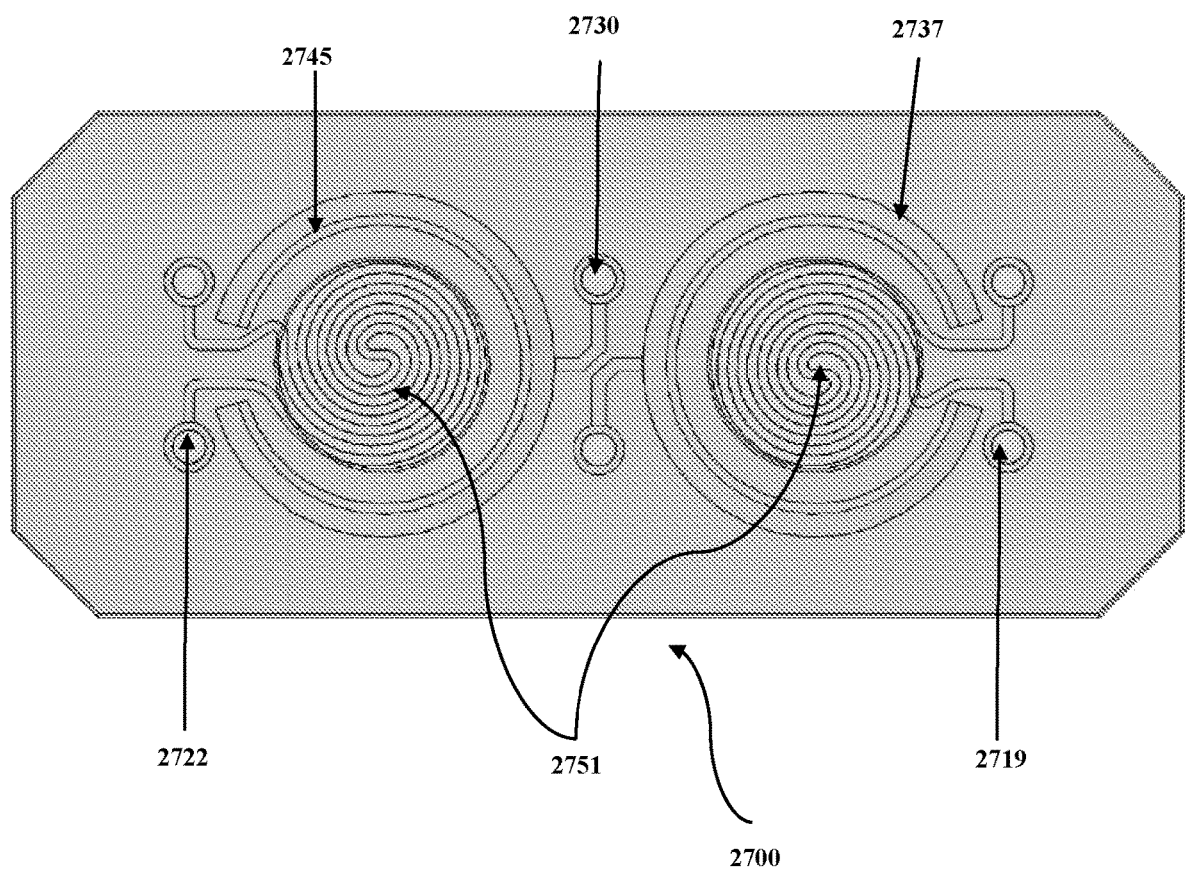

FIG. 27 illustrates one embodiment of a top view of an assembled open-top chip microfluidic device of the device depicted in FIG. 13.

Figure 28:
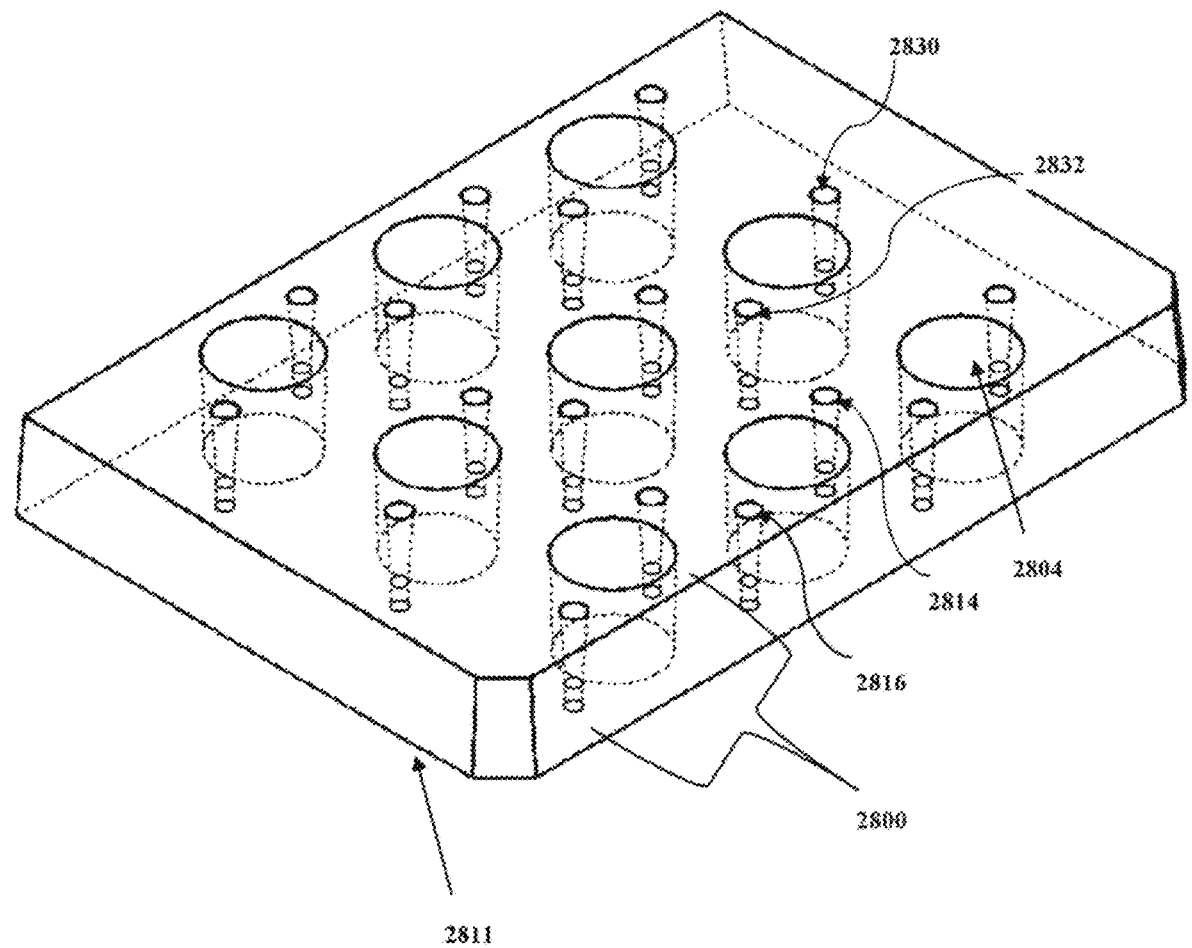

FIG. 28 illustrates one embodiment of an array of open chambers in an open-top chip device as contemplated herein.

Figure 29A:
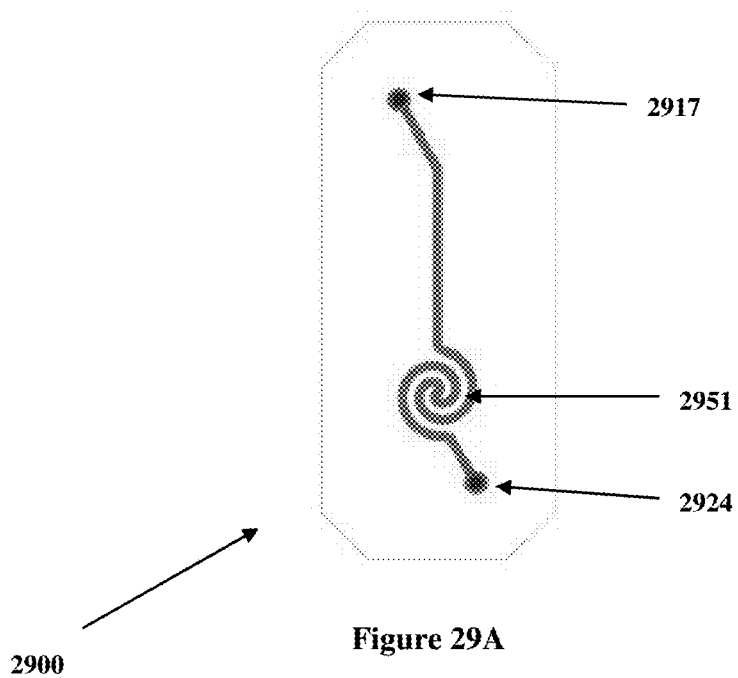
Figure 29B:
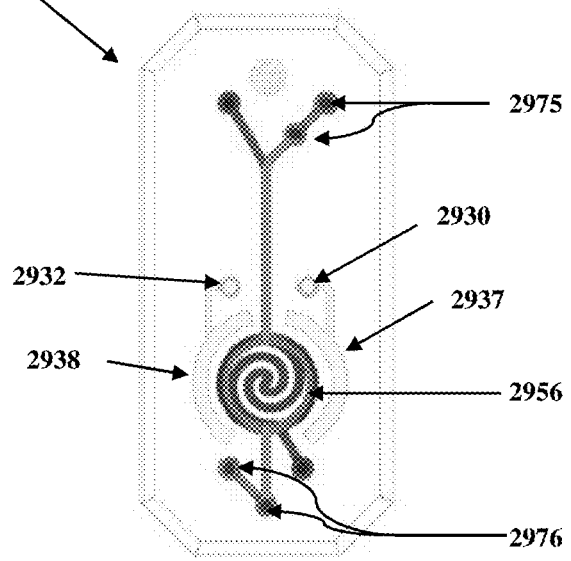

FIG. 29A-B illustrates one embodiment of a stretchable open top chip device.

FIG. 29A: A bottom structure with a spiral microchannel with an inlet well and and outlet well.

FIG. 29B: A top view of a spiral microchannel configured with a circular vacuum chamber.

Figure 30:
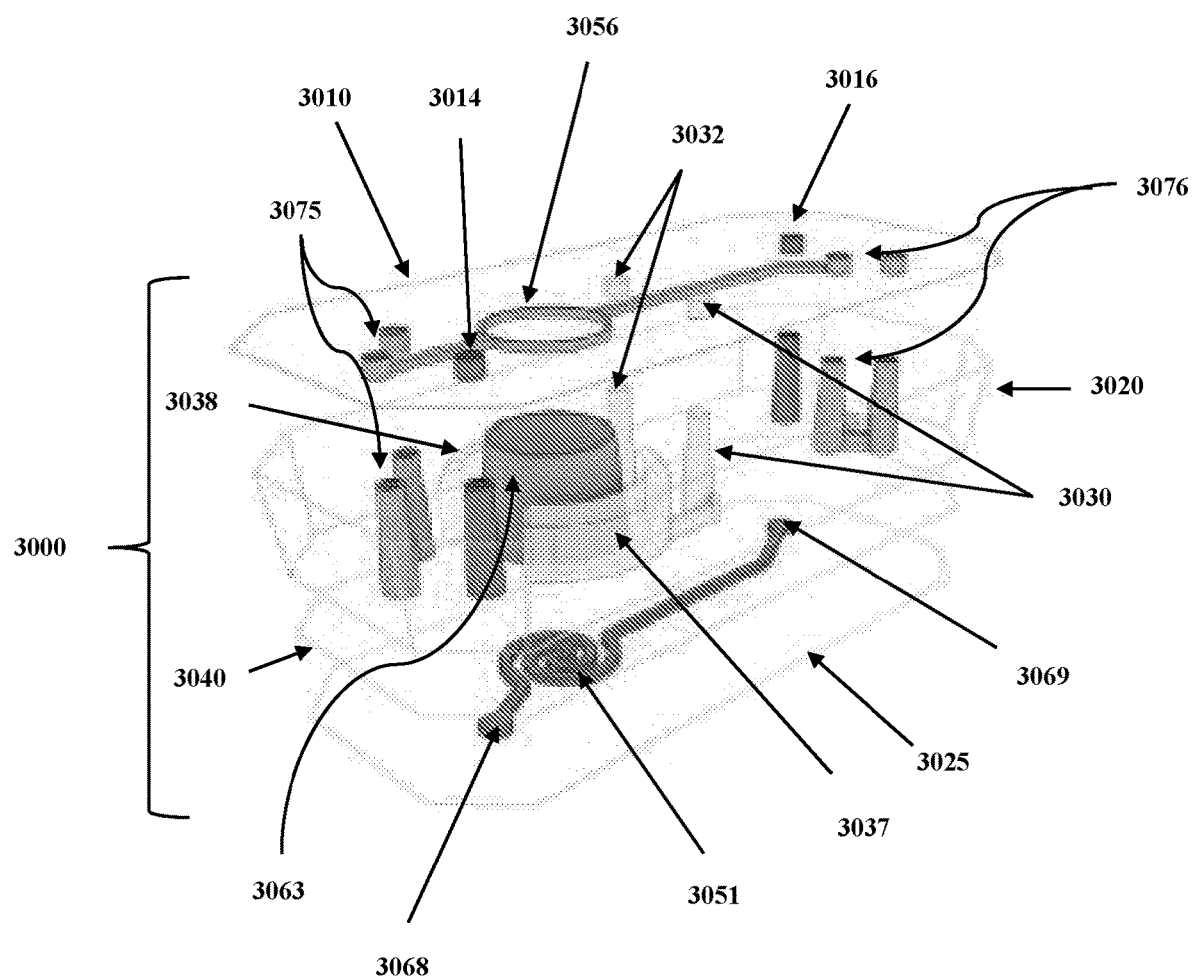

FIG. 30 illustrates an exploded view of one embodiment of a stretchable open top chip device demonstrating the layering of a fluidic top, top structure and bottom structure.

Figure 31A:
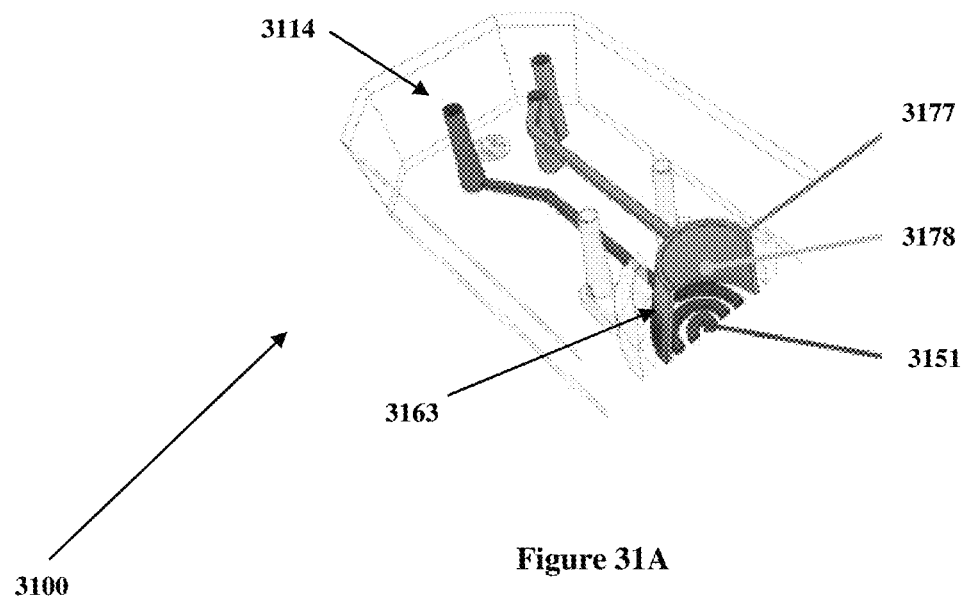
Figure 31B:
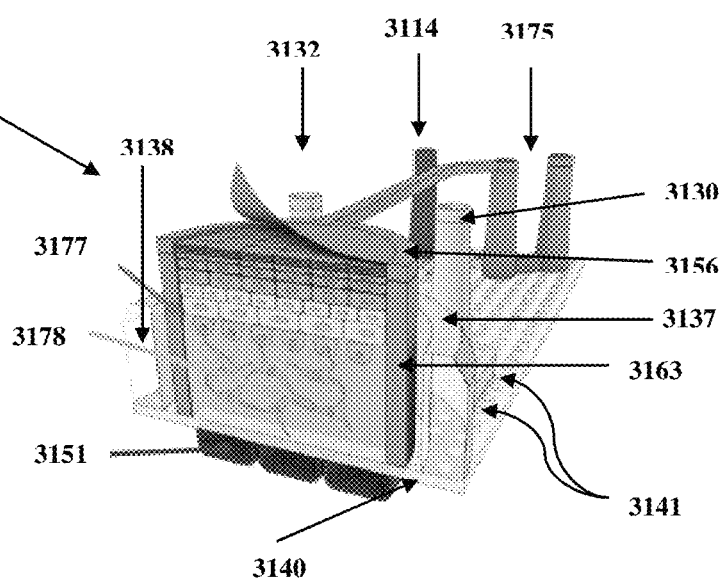

FIG. 31A-B illustrates a cut-away view of one embodiment of a stretchable open top chip device showing the regional placement of assay cells (e.g., epithelial cells, dermal cells and/or vascular cells).

Figure 32:
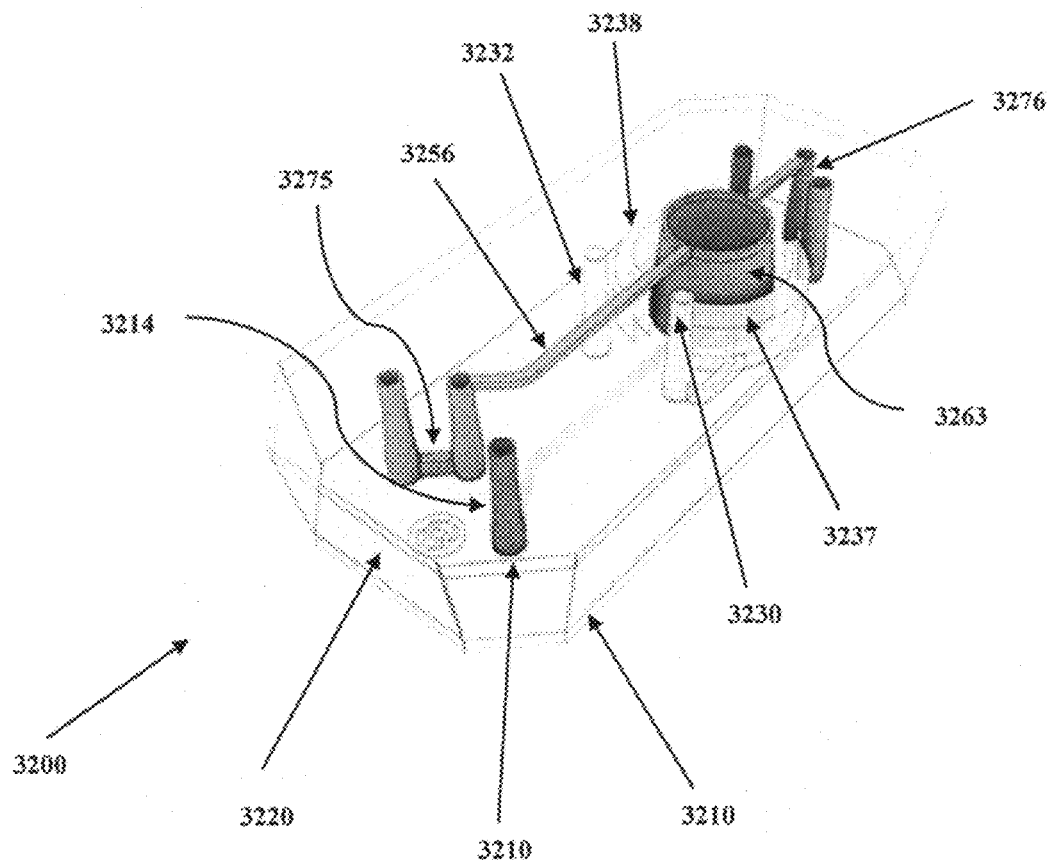

FIG. 32 illustrates a fully assembled view of one embodiment of a stretchable open top chip device.

Figure 33A:
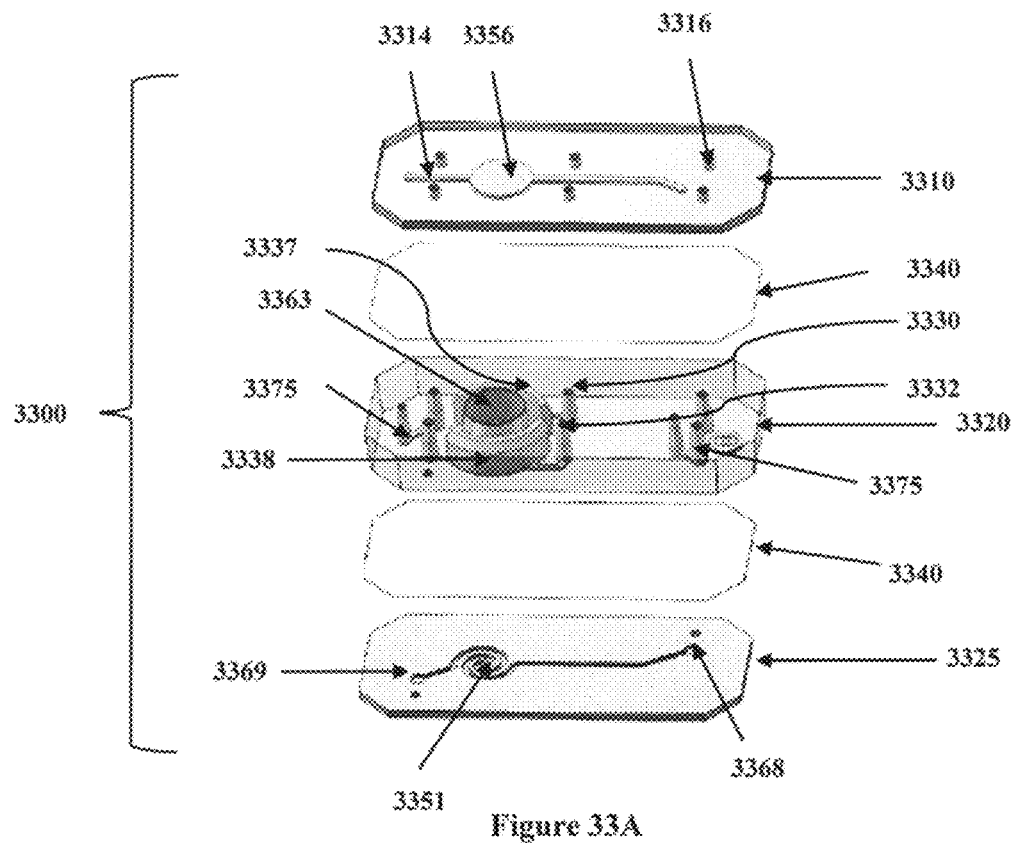
Figure 33B:
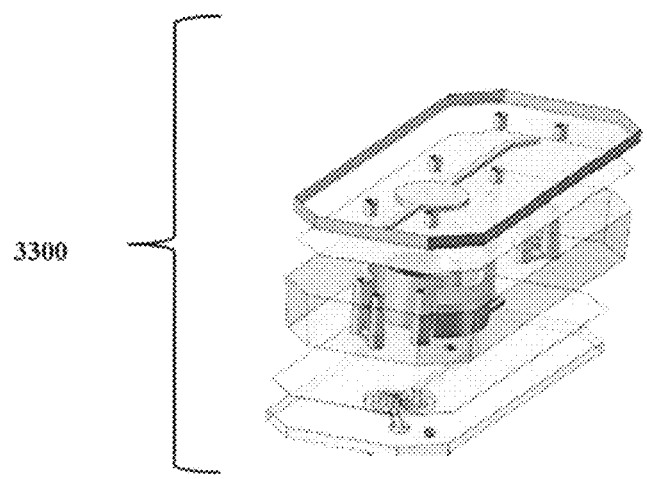

FIGS. 33A and 33B illustrate exploded views of two embodiments of a stretchable open top chip device.

Figure 34A:
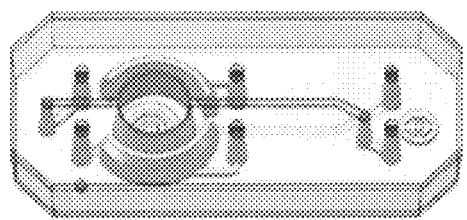
Figure 34B:
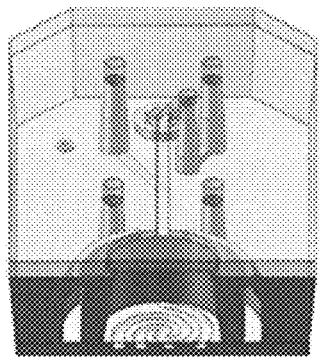

FIGS. 34A and 34B illustrate assembled views of a stretchable open top chip device as depicted in FIGS. 33A and 33B.

Figure 35A:
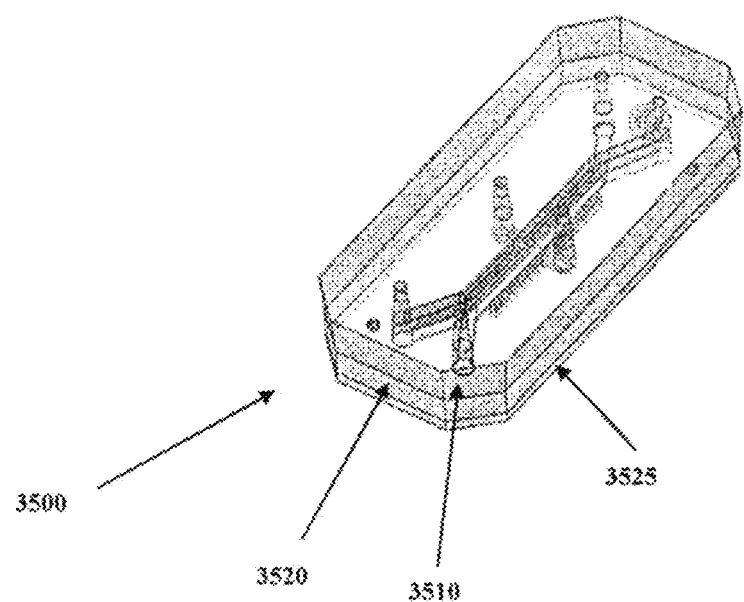
Figure 35B:
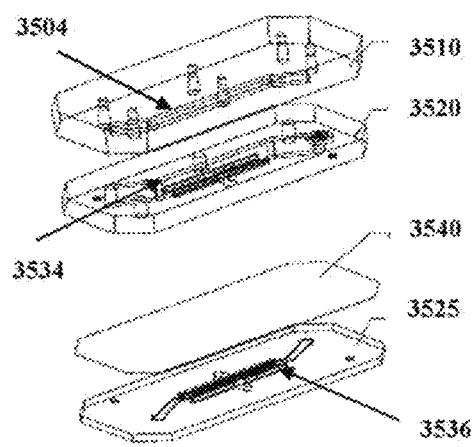

FIGS. 35A and 35B respectively illustrate an assembled isometric view and an exploded view of a tall channel stretchable open top chip device.

Figure 36:
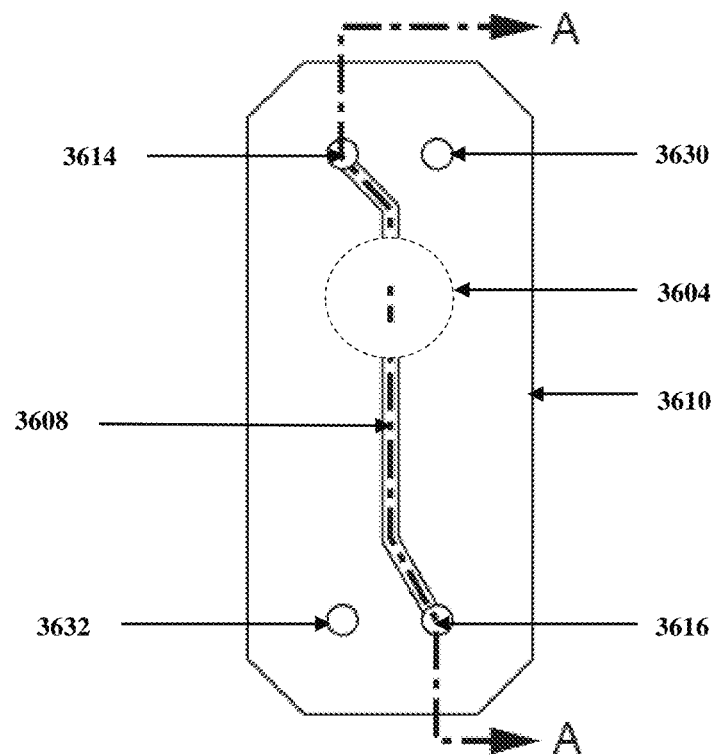

FIG. 36 presents a top assembled view of one embodiment of a stretchable open-top microfluidic chip comprising a fluidic cover and a single channel.

Figure 37A:
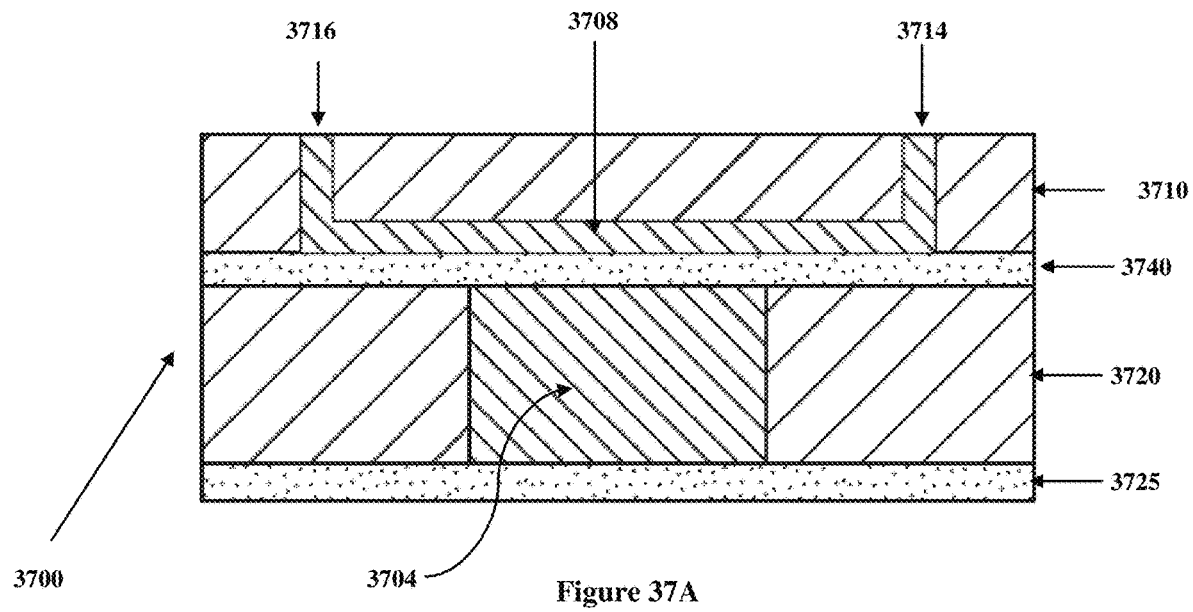
Figure 37B:
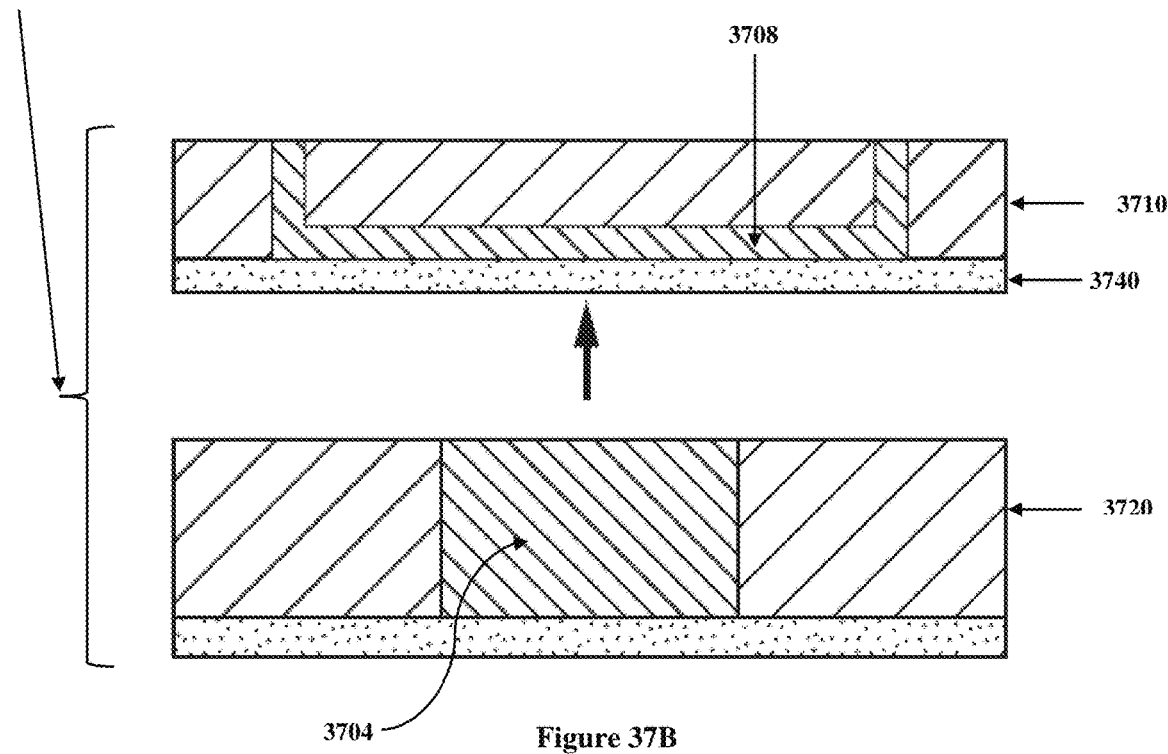

FIG. 37A-B presents a crossectional view of a first embodiment of a stretchable open top microfluidic chip along plane A of FIG. 36.

Figure 38A:
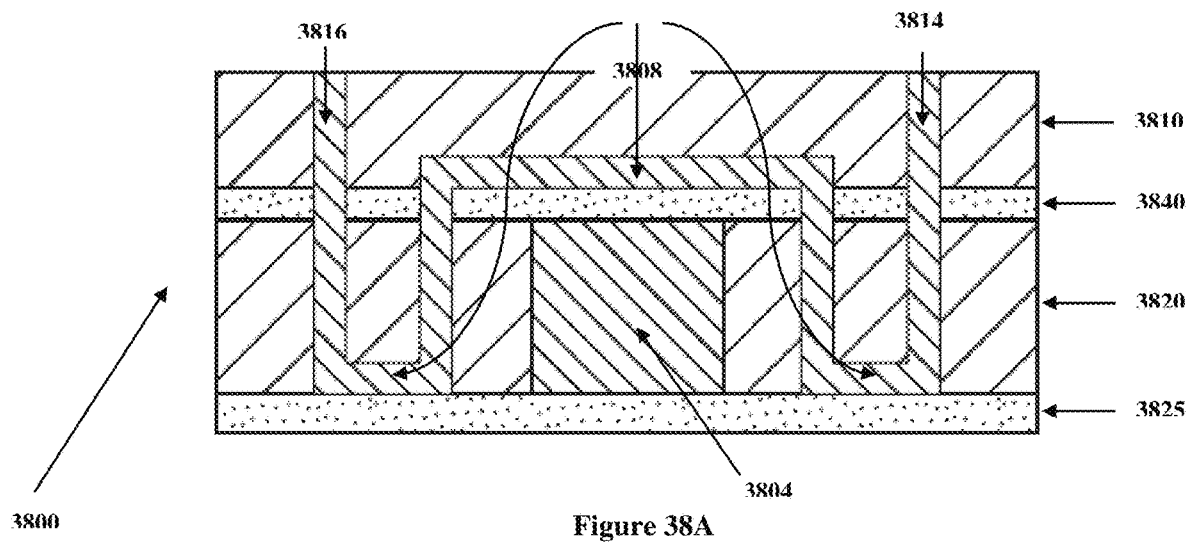
Figure 38B:
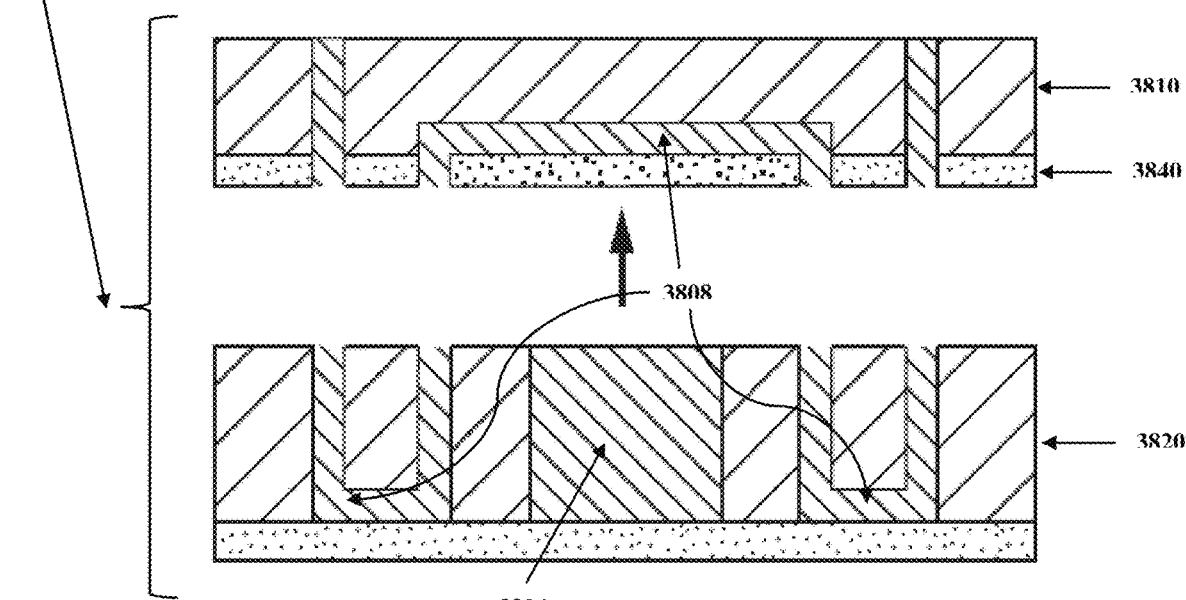

FIG. 37A: Illustrates a fluidic cover in a closed position.
FIG. 37B: Illustrates a fluidic cover in an open position.
FIG. 38A-B presents a crossection view of a second embodiment of a stretchable open top microfluidic chip along plane A of FIG. 36.

FIG. 38A: Illustrates a fluidic cover in a closed position.

FIG. 38B: Illustrates a fluidic cover in an open position.

Figure 39:
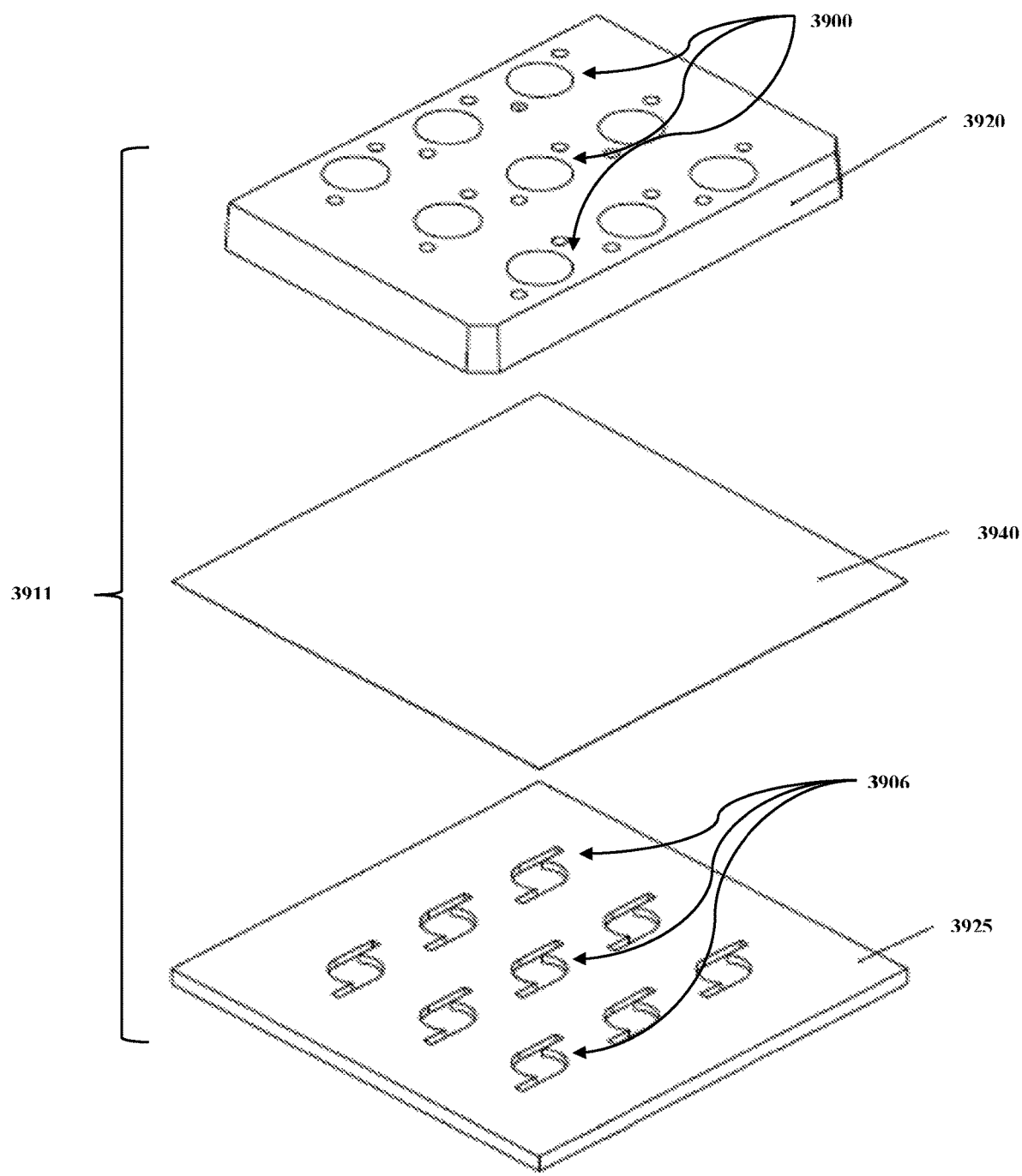

FIG. 39 presents an exploded view of the array device depicted in FIG. 28.

DESCRIPTION OF THE INVENTION

A microfluidic device is contemplated comprising an open-top cavity with structural anchors on the vertical wall surfaces that serve to prevent gel shrinkage-induced delamination, a porous membrane (optionally stretchable) positioned in the middle over a microfluidic channel(s). The device can be used in many ways with many types of tissues and cells. For example, the organ mimic device described herein can be used for the identification of markers of disease; assessing efficacy of anti-cancer therapeutics; testing gene therapy vectors; drug development; screening; and for studies of particular cells (and arrangements of cells). In one embodiment, the device serves as a skin model. In this embodiment, the open-top device provides an uncovered chamber comprising a skin-like, human or animal tissue that can be tested with drugs, including topicals and aerosols.

A. Gel-Containing Skin Model

In one embodiment, the present invention contemplates a construct comprising a "dermis" with fibroblasts embedded in a matrix having a thickness between 0.2 and 6.0 mm, e.g. a collagen I gel matrix, and an "epidermis", which is comprised of keratinocytes, e.g. stratified, differentiated keratinocytes. A matrix such as a collagen gel provides scaffolding, nutrient delivery, and potential for cell-to-cell interaction. In one embodiment, the construct further comprises a functional basement membrane, which separates the epidermis from the dermis.

In one embodiment, the present invention contemplates a layered structure comprising i) fluidic channels covered by ii) a porous membrane, said membrane comprising iii) a layer of endothelial cells and said membrane position below iv) a gel matrix comprising fibroblasts and keratinocytes. In a preferred embodiment, the fibroblasts are within the gel matrix and the keratinocytes are on top of the gel matrix. In a preferred embodiment, the keratinocytes comprise more than one layer on top of the gel matrix. In a preferred embodiment, the layer of endothelial cells is positioned on the bottom of the membrane and is in contact with the fluidic channels. In a preferred embodiment, the fluidic channels provide shear to said endothelial cells.

It is not intended that the present invention be limited to the thickness of the gel matrix. However, a preferred range of thickness is between 0.2 and 6 mm, and more preferably between 0.5 mm and 3.5 mm, and still more preferably approximately 1-2 mm. In a preferred embodiment, the gel matrix is stretchable. In a preferred embodiment, the gel matrix is stretched in a manner such that the entire gel matrix expands, not just a portion of the gel matrix (such as only the bottom or top of the matrix). In a preferred embodiment, the gel matrix is stretched by vacuum channels that are designed to provide pneumatic stretching that is uniform across the thickness of the gel.

In a preferred embodiment, the layered structure is positioned in an open-top microfluidic device (i.e. a device lacking a top covering), wherein the gel matrix is secured in a chamber of the device by anchors. In a preferred embodiment, the surfaces of the device that contact the gel matrix have been treated to enhance attachment of the gel matrix. In a preferred embodiment, the surfaces have been plasma treated, i.e. the surface is activated with ionized gas. It has been found that the surface treatment, in combination with the anchors, prevent delamination of the gel from the walls of the chamber.

In one embodiment, the fluidic channels bring one or more compounds that will induce the endothelial cells to differentiate. In one embodiment, the fluidic channels comprise a solution comprising a vascular endothelial growth factor (VEGF).

The open-top device provides an uncovered chamber comprising a skin-like tissue that can be tested with topicals and aerosols. In one embodiment, drugs are applied topically or transdermally to the keratinocyte layer(s). As used herein, the term "topical" refers to administration of an agent or agents (e.g. cosmetic, medication, vitamin, etc.) on the skin. "Transdermal" refers to the delivery of an agent (e.g. cosmetic, medication, vitamin, etc.) through the skin (e.g. so that at least some portion of the population of molecules reaches underlying layers of the skin).

In one embodiment, a candidate cosmetic is applied to the keratinocyte layer(s). As used herein, a "cosmetic" refers to a substance that aids in the enhancement or protection of the appearance (e.g. color, texture, look, feel, etc.) or odor of a subject's skin. A cosmetic may or may not change the underlying structure of the skin.

In this skin model, a layer of endothelial cells (ECs) is positioned on the underside of the membrane facing the fluidic channels. Endothelial cells and endothelial stem cells will, under appropriate conditions, migrate and differentiate. In terms of migration, while not limited to any particular mechanism, it is believed that this motile process is directionally regulated by chemotactic, haptotactic, and mechanotactic stimuli and (where applicable) may require degradation of the extracellular matrix to enable progression of the migrating cells. It is believed to involve the activation of several signaling pathways that converge on cytoskeletal remodeling. Generally, it is been observed that the endothelial cells extend, contract, and progress forward. In a preferred embodiment, ECs are grown on a membrane with a porosity sufficient to allow for this cell migration, i.e. through the membrane.

In some embodiments, growth factors or compounds that enhance the production of the desired cell type(s) can be added to the perfusion fluid in the fluidic channels. By way of non-limiting example, erythropoietin stimulates the production of red blood cells, VEGF stimulates angiogenesis, and thrombopoietin stimulates the production of megakaryocytes and platelets. "Vascular growth" is defined here as at least one of vasculogenesis and angiogenesis and includes formation of one or more of the following: capillaries, arteries, veins or lymphatic vessels. Blood vessel formation de novo (vasculogenesis) and from existing vessels (angiogenesis) results in blood vessels lined by endothelial cells (ECs).

Vascular endothelial growth factor (VEGF) is an interesting inducer of angiogenesis and lymphangiogenesis because it is highly specific endothelial cells. The VEGF family currently comprises seven members: VEGF-A, VEGF-B, VEGF-C, VEGF-D, VEGF-E, VEGF-F, and PlGF. All members have a common VEGF homology domain. Signal transduction involves binding to tyrosine kinase receptors and results in endothelial cell proliferation, migration, and new vessel formation. In a preferred embodiment, VEGF (and/or other known angiogenic or arteriogenic growth factors) is used to induce EC differentiation, proliferation, infiltration, angiogenesis, vascularization, etc., or any combination thereof.

It is not intended that the present invention be limited to only one source or type of endothelial cell (EC). In one embodiment, primary ECs are used in the open-top device. In one embodiment, freshly isolated small vessel human dermal microvascular endothelial cells are employed on the open-top-chip. In one embodiment, an endothelial cell line is employed. In yet another embodiment, human umbilical vein endothelial cells (HUVECs) are used. In still another embodiment, bone marrow-derived endothelial progenitor cells are seeded in the chip. In still another embodiment, stem cells that can differentiate into ECs are used.

It is not intended that the present invention be limited to only one place for seeding the open-top-chip with ECs. While placement of ECs on the underside of the membrane (in contact with the fluidics) is preferred, placement on the topside of the membrane and placement within the gel matrix itself are alternative embodiments. With regard to the latter, in one embodiment, microfluidic pathways in the gel itself are created that are thereafter seeded with the endothelial cells.

For example, in one embodiment, microfluidic vessel networks are engineered by seeding human endothelial cells [e.g. umbilical vein endothelial cells (HUVECs)] into microfluidic circuits formed via soft lithography in a type I collagen gel. Native, type I collagen at 6-10 mg/mL is of an appropriate stiffness to allow high reproducibility of vessel microstructure and also enables remodeling through degradation and deposition of extracellular matrix. The lithographic process enables the formation of endothelium along the microfluidic channels and the incorporation of living cells within the bulk collagen gel matrix within the open-top-chip.

In one embodiment, endothelial cells are seeded into the gel containing (or onto confluent lawns of) human fibroblasts and cultured in the presence of high levels of ascorbate 2-phosphate to create a tissue-like structure in which endothelial cells organize into tube-like structures.

It is not intended that the skin model be limited to just one type of keratinocyte. Indeed, the model can be used with many types of cells of the integumentary system including but not limited to Keratinizing epithelial cells, Epidermal keratinocyte (differentiating epidermal cell), Epidermal basal cell (stem cell), Keratinocyte of fingernails and toenails, Nail bed basal cell (stem cell), Medullary hair shaft cell, Cortical hair shaft cell, Cuticular hair shaft cell, Cuticular hair root sheath cell, Hair root sheath cell of Huxley's layer, Hair root sheath cell of Henle's layer, External hair root sheath cell, and Hair matrix cells (stem cell). In one embodiment, human foreskin keratinocytes are employed.

B. Other Cells and Tissues

A variety of different cells and tissue types can be modeled and tested with the open-top spacer chip described herein. Indeed, the system can virtually be adapted to all epithelial tissues. In addition to skin, preferred models include (but are not limited) to Lung, the Small Airway, the gut, muscle (including skeletal, cardiac and or smooth muscle, and the Blood Brain Barrier (BBB). Both human and animal cells are contemplated. Cell types which can be used in the open-top devices include, but are not limited to Wet stratified barrier epithelial cells, such as Surface epithelial cell of stratified squamous epithelium of cornea, tongue, oral cavity, esophagus, anal canal, distal urethra and vagina, basal cell (stem cell) of epithelia of cornea, tongue, oral cavity, esophagus, anal canal, distal urethra and vagina, Urinary epithelium cell (lining urinary bladder and urinary ducts); Exocrine secretory epithelial cells, such as Salivary gland mucous cell (polysaccharide-rich secretion), Salivary gland serous cell (glycoprotein enzyme-rich secretion), Von Ebner's gland cell in tongue (washes taste buds), Mammary gland cell (milk secretion), Lacrimal gland cell (tear secretion), Ceruminous gland cell in ear (wax secretion), Eccrine sweat gland dark cell (glycoprotein secretion), Eccrine sweat gland clear cell (small molecule secretion), Apocrine sweat gland cell (odoriferous secretion, sex-hormone sensitive), Gland of Moll cell in eyelid (specialized sweat gland), Sebaceous gland cell (lipid-rich sebum secretion), Bowman's gland cell in nose (washes olfactory epithelium), Brunner's gland cell in duodenum (enzymes and alkaline mucus), Seminal vesicle cell (secretes seminal fluid components, including fructose for swimming sperm), Prostate gland cell (secretes seminal fluid components), Bulbourethral gland cell (mucus secretion), Bartholin's gland cell (vaginal lubricant secretion), Gland of Littre cell (mucus secretion), Uterus endometrium cell (carbohydrate secretion), Isolated goblet cell of respiratory and digestive tracts (mucus secretion), Stomach lining mucous cell (mucus secretion), Gastric gland zymogenic cell (pepsinogen secretion), Gastric gland oxyntic cell (hydrochloric acid secretion), Pancreatic acinar cell (bicarbonate and digestive enzyme secretion), pancreatic endocrine cells, Paneth cell of small intestine (lysozyme secretion), intestinal epithelial cells, Types I and II pneumocytes of lung (surfactant secretion), and/or Clara cell of lung.

One can also coat the membrane with Hormone secreting cells, such as endocrine cells of the islet of Langerhands of the pancreas, Anterior pituitary cells, Somatotropes, Lactotropes, Thyrotropes, Gonadotropes, Corticotropes, Intermediate pituitary cell, secreting melanocyte-stimulating hormone; and Magnocellular neurosecretory cells secreting oxytocin or vasopressin; Gut and respiratory tract cells secreting serotonin, endorphin, somatostatin, gastrin, secretin, cholecystokinin, insulin, glucagon, bombesin; Thyroid gland cells such as thyroid epithelial cell, parafollicular cell, Parathyroid gland cells, Parathyroid chief cell, Oxyphil cell, Adrenal gland cells, chromaffin cells secreting steroid hormones (mineralcorticoids and gluco corticoids), Leydig cell of testes secreting testosterone, Theca interna cell of ovarian follicle secreting estrogen, Corpus luteum cell of ruptured ovarian follicle secreting progesterone, Granulosa lutein cells, Theca lutein cells, Juxtaglomerular cell (renin secretion), Macula densa cell of kidney, Peripolar cell of kidney, and/or Mesangial cell of kidney.

Additionally or alternatively, one can treat at least one side of the membrane with Metabolism and storage cells such as Hepatocyte (liver cell), White fat cell, Brown fat cell, Liver lipocyte. One can also use Barrier function cells (Lung, Gut, Exocrine Glands and Urogenital Tract) or Kidney cells such as Kidney glomerulus parietal cell, Kidney glomerulus podocyte, Kidney proximal tubule brush border cell, Loop of Henle thin segment cell, Kidney distal tubule cell, and/or Kidney collecting duct cell.

Different geometries can be employed with dimensions related to the different tissue types. For example, in one embodiment, relatively tall spacer open top chip dimensions are contemplated for the skin model, bronchial model, Kidney model and Gut model, i.e. chamber height between 500 microns to 5 mm, chamber width 1 mm, chamber length 1.6 mm.

In another embodiment, relatively short spacer open top chip dimensions are employed: chamber height between 100 to 500 microns, chamber width 1 mm, chamber length 1.6 mm. These dimensions are better suited to the Brain barrier and Lung models.

An example of the importance of its application is the small airway model: Small Airway cells feel the paracrine stimulation of neighbor cells, which stimulate their fully differentiation. In the normal chip design cytokines are continuously flushed away from the epithelial compartment by the constant flow, and this reduces or impedes epithelial cell differentiation. The presence of this porous matrix efficiently buffers the effect of flow reducing or annul the effect of flow under cells.

The physical properties of the gels and fluids can vary (in addition to the different geometries and dimensions for each of the different tissue types). For example, for the Skin model and bronchial model, a relatively high concentration collagen (8-11 mg/ml) is used. For the Kidney model and Gut model, a 1:1 mixture of high concentration collagen: Matrigel is employed. For the Brain barrier and lung models, a 1:1 low concentration (e.g. 3 mg/ml) of collagen/matrigel and/or fibronectin is employed. All in all, concentrations above 0.3 mg/ml are required to form gels. Preferred concentrations range between 3 mg/ml and 10 mg/ml. However, concentrations above 5 mg/ml are particularly suitable for use in the open top chip.

Not all of the organ models require a gel. Indeed, some organ chips are ideally used without a gel (e.g. lung). When gels are used, more than one gel layer can be employed. For example, hepatocytes can have a gel on both sides of the cells (e.g. a matrigel layer on top and a collagen layer on the bottom. Importantly, the gel can have a variety of thicknesses, including a thin (molecular) coating. In one embodiment, the coating is made with by ink jet printing.

Some cells do very well on patterned gels. For example, muscle cells do well when they can deform to the surface. Indeed, in one embodiment, the present invention contemplates a gel pattern such that the sarcomeres align.

Importantly, the present invention contemplates electrophysiological measurements in more than the blood brain barrier (BBB) model. The present invention contemplates such measurements for muscle (whether skeletal, cardiac or smooth muscle) cells.

DETAILED DESCRIPTION OF THE INVENTION

While this invention is susceptible of embodiment in many different forms, there is shown in the drawings and will herein be described in detail preferred embodiments of the invention with the understanding that the present disclosure is to be considered as an exemplification of the principles of the invention and is not intended to limit the broad embodiment of the invention to the embodiment illustrated. For purposes of the present detailed description, the singular includes the plural and vice versa (unless specifically disclaimed); the word "or" shall be both conjunctive and disjunctive; the word "all" means "any and all"; the word "any" means "any and all"; and the word "including" means "including without limitation."

Those of ordinary skill in the art will realize that the following description is illustrative only and is not intended to be in any way limiting. Other embodiments will readily suggest themselves to such skilled persons having the benefit of this disclosure. Reference will now be made in detail to implementations of the example embodiments as illustrated in the accompanying drawings. The same or similar reference indicators will be used throughout the drawings and the following description to refer to the same or like items. It is understood that the phrase "an embodiment" encompasses more than one embodiment and is thus not limited to only one embodiment.

As used herein, the term "rigid" refers to a material that is stiff and does not stretch easily, or maintains very close to its original form after a force or pressure has been applied to it. The term "elastomeric" as used herein refers to a material or a composite material that is not rigid as defined herein. An elastomeric material can be generally moldable, extrudable, cuttable, machinable, castable, and/or curable, and can have an elastic property that enables the material to deform (e.g., stretching, expanding, contracting, retracting, compressing, twisting, and/or bending) when subjected to a mechanical force or pressure and partially or completely resume its original form or position in the absence of the mechanical force or pressure. In some embodiments, the term "elastomeric" can also refer to a material that is flexible/stretchable but it does not resume its original form or position after pressure has been applied to it and removed thereafter. The terms "elastomeric" and "flexible" are used interchangeably herein.

The functionality of cells, tissue types, organs, or organ-components can be implemented in one or more microfluidic devices or "chips" that enable researchers to study these cells, tissue types, organs, or organ-components outside of the body while mimicking much of the stimuli and environment that the tissue is exposed to in-vivo. In some embodiments, it is desirable to implement these microfluidic devices into interconnected components that can simulate the function of groups of organs, organ-components, or tissue systems. In some cases it is desirable to configure the microfluidic devices so that they can be easily inserted and removed from an underlying fluidic system that connects to these devices in order to vary the simulated in-vivo conditions and organ systems (e.g., in situ conditions).

Many of the problems associated with earlier systems can be solved by providing an open-top style microfluidic device that allows topical access to one or more parts of the device or cells that it comprises. For example, the microfluidic device can include a removable cover, that when removed, provides access to the cells of interest in the microfluidic device. In some embodiments, the microfluidic devices include systems that constrain fluids, cells, or biological components to desired area(s). The improved systems provide for more versatile experimentation when using microfluidic devices, including improved application of treatments being tested, improved seeding of additional cells, and/or improved aerosol delivery for select tissue types. In a preferred embodiment, the open-top microfluidic device comprises a gel matrix.

The present disclosure additionally relates to organ-on-chips ("OOCs"), such as fluidic devices comprising one or more cells types for the simulation one or more of the function of organs or organ-components. Accordingly, the present disclosure additionally describes open-top organ-on-chips that solve problems associated with earlier fluidic systems. Without limitation, specific examples include models of skin, bronchial, and gut.

It is also desirable in some embodiments to provide access to regions of a cell-culture device. For example, it can be desirable to provide topical access to cells to (i) apply topical treatments with liquid, gaseous, solid, semi-solid, or aerosolized reagents, (ii) obtain samples and biopsies, or (iii) add additional cells or biological/chemical components.

The present disclosure relates to fluidic systems that include a fluidic device, such as a microfluidic device with an opening that provides direct access to device regions or components (e.g. access to the gel region, access to one or more cellular components, etc.). Although the present disclosure provides an embodiment wherein the opening is at the top of the device (referred to herein with the term "open top"), the present invention contemplates other embodiments where the opening is in another position on the device. For example, in one embodiment, the opening is on the bottom of the device. In another embodiment, the opening is on one or more of the sides of the device. In another embodiment, there is a combination of openings (e.g. top and sides, top and bottom, bottom and side, etc.).

While detailed discussion of the "open top" embodiment is provided herein, those of ordinary skill in the art will appreciate that many embodiments of the "open top" embodiment apply similarly to open bottom embodiments, as well as open side embodiments or embodiments with openings in any other regions or directions, or combinations thereof. Similarly, the device need not remain "open" throughout its use; rather, as several embodiments described herein illustrate, the device may further comprise a cover or seal, which may be affixed reversibly or irreversibly. For example, removal of a removable cover creates an opening, while placement of the cover back on the device closes the device. The opening, and in particular the opening at the top, provides a number of advantages, for example, allowing (i) the creation of one or more gel layers for simulating the application of topical treatments on the cells, tissues, or organs, or (ii) the addition of chemical or biological components such as the seeding of additional cell types for simulating the function of tissue and organ systems. The present disclosure further relates to improvement in fluidic system(s) that improve the delivery of aerosols to simulate the function of tissue and organ systems, such as simulated function of lung tissues.

Furthermore, the present disclosure contemplates improvements to fluidic systems that include a fluidic device, such as a microfluidic device with an open-top region that reduces the impact of stress that can cause the delamination of tissue or related component(s) (e.g., such as a gel layer).

Improvements to microfluidic devices for simulating the function of a tissue are contemplated by the present disclosure that include one or more of an open-top microfluidic device with two or more chambers (e.g., microchannels) separated by a membrane. In some embodiments, one or more of the devices further comprises a gel in a chamber (e.g., microchannel or cavity) accessible through an opening, including but not limited to an open-top structure, of the microfluidic device. In some embodiments, the device further comprises a removable or permanent cover for the microfluidic device where the cover optionally has a fluidic chamber or microchannel therein. Other desirable improvements that are contemplated include a patterned gel in a microfluidic device.

The present disclosure further describes a method for culturing cells in open-top devices. In some embodiments, the method comprises placing a gel into an open-top structure. In some embodiments, the method further comprises patterning the gel using a shaping device, such as a patterned plunger stamp, a shaping stamp, or similar devices. In some embodiments, the method comprises permanently or reversibly applying a cover or other shaping device to the open-top.

The present disclosure further relates to the use of fluidic systems that include a fluidic device, such as a microfluidic device with an open-top, to construct a model simulating the structure and/or one or more functions of, for example, skin, bronchial, or gut. In some embodiments, these models benefit from the presence of gels, which for example, can provide a mechanical, biochemical environment for one or more cells types, augment the mass-transport characteristics, or provide an additional compartment that may be used, for example, to house an additional cell type (e.g. fibroblasts).

A system that provides for the use of a gel can be particularly desirable for a skin model. For example, the current state-of-the-art skin model, the living skin equivalent (LSE), is a 3D gel, 2 mm to 3 mm thick, that is embedded with fibroblasts with differentiated keratinocytes on top of the gel. The actual thickness of the gel can range from 0.1 mm to 5 mm. It is known that a 3D gel is preferred to properly culture the fibroblasts that, in turn, enables keratinocytes to fully differentiate. An open-top architecture as described by some embodiments herein is desirable because it enables LSE-like and similar cultures of fibroblasts and keratinocytes, while further allowing the introduction of an endothelial layer, the application of shear forces, and the application of stretching to create a more physiologically relevant model. Each of these optional features, individually and collectively, provides desirable improvements over current state-of-the-art LSE-like skin models.

Figure 1:
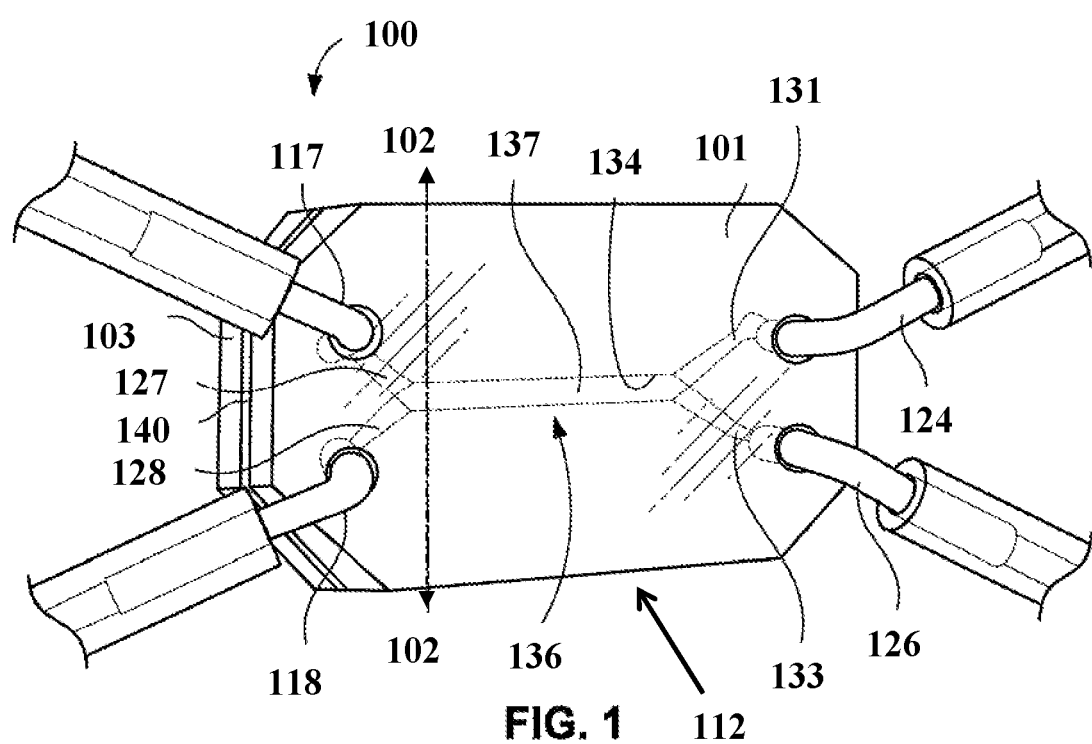
FIG. 1 illustrates an exemplary microfluidic device with a membrane region having cells thereon according to embodiments of the present disclosure.
Figure 2:
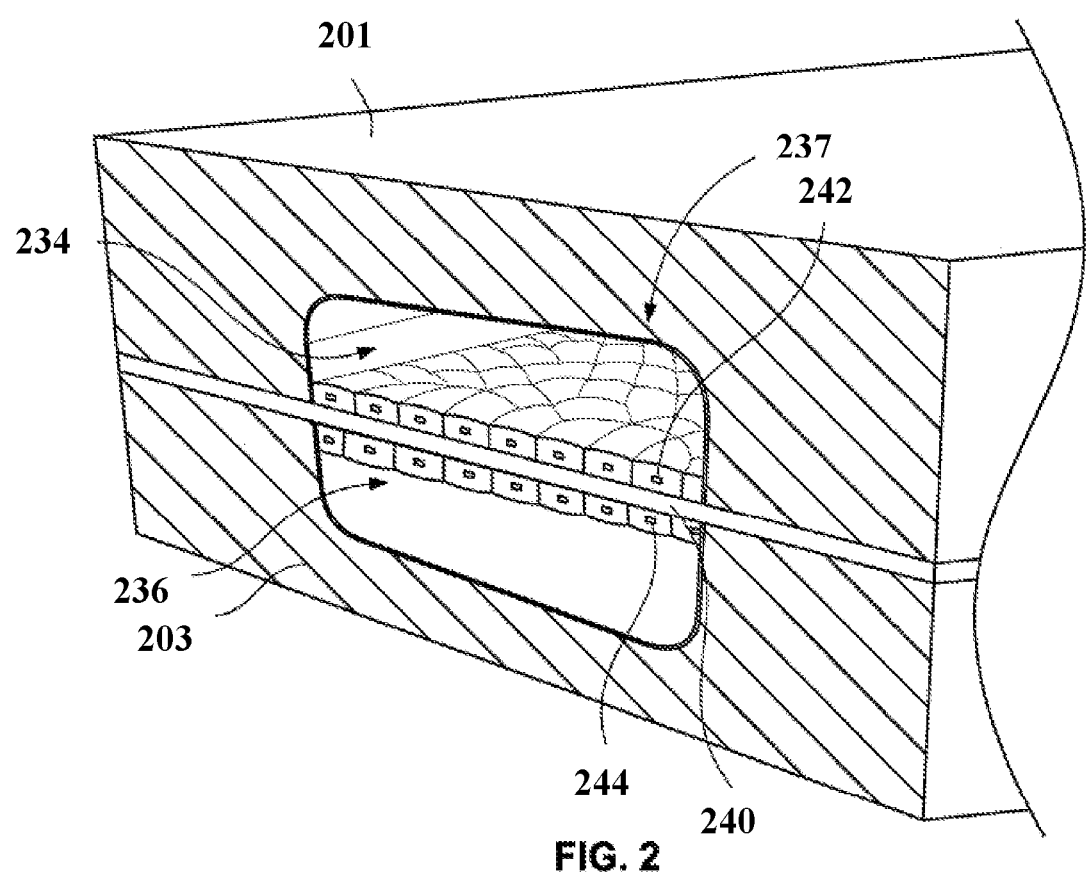
FIG. 2 is a cross-section of the microfluidic device taken along line 102-102 of FIG. 1, illustrating the membrane separating the first microchannel and the second microchannel.

Referring now to FIGS. 1 and 2, one type of a microfluidic device referred to as an organ-on-chip ("OOC") device 100 is illustrated that may be modified to include open-top embodiments that are described in more detail later in this disclosure (see, e.g., FIGS. 3-5A-F and 8A-C-12). The OOC device 100 includes a body 112 that typically comprises an upper body segment 101 and a lower body segment 103. The upper body segment 101 and the lower body segment 103 are typically made of a polymeric material, including, but not limited to, PDMS (poly-dimethylsiloxane), polycarbonate, polyethylene terephthalate, polystyrene, polypropylene, cyclo-olefin polymers, polyurethanes, fluoropolymers, styrene derivatives like styrene ethylene butylene styrene (SEBS), or other polymer materials. The upper body segment 101, while illustrated with a first fluid inlet 117 and a second fluid inlet 118, can be modified to include an open region 104 (not shown) to optionally allow the application of a gel layer 150 (not shown) to a membrane 140 and optionally modified to exclude the illustrated first fluid inlet 117 and/or second fluid inlet 118. A first fluid path for a first fluid includes the first fluid inlet 117, a first seeding channel 127, an upper microchannel 134, an exit channel 131, and then the first fluid outlet 124. A second fluid path for a second fluid includes the second fluid inlet 118, a second seeding channel 128, a lower microchannel 136, an outlet channel 133, and then the second fluid outlet 126.

Referring to FIG. 2, a membrane 240 extends between the upper body segment 201 and the lower body segment 203. The membrane 240 is preferably an inert, polymeric, micromolded membrane having uniformly distributed pores with sizes normally in the range of about 0.1 μm to 20 μm, though other pore sizes are also contemplated. In some embodiments, the pore size is in the range of about 0.1 μm to 20 μm. The overall dimensions of the membrane 240 include any size that is compatible with or otherwise based on the dimensions of upper body segment 201 and lower body segment 103, such as about 0.05-100 mm (channel width) by about 0.5-300 mm (channel length), though other overall dimensions are also contemplated. In some embodiments, the overall dimensions of the membrane 240 are about 1-100 mm (channel width) by about 1-100 mm (channel length). In one embodiment, the thickness of the membrane 240 is generally in the range of about 5 μm to about 500 μm, and in some embodiments, the thickness is about 20-50 μm. In some embodiments, the thickness can be less than 1 μm or greater than 500 μm. It is contemplated that the membrane 240 can be made of materials including, but not limited to poly-dimethylsiloxane (PDMS), polycarbonate, polyethylene terephthalate, styrene derivatives (e.g, styrene ethylene butylene styrene, SEBS), fluoropolymers, and/or other elastomeric or rigid materials. Additionally, the membrane 240 can be made of biological materials including, but not limited to, polylactic acid, collagen, gelatin, cellulose and its derivatives, poly(lactic-co-glycolic acid), and/or comprise such materials in addition to one or more polymeric materials. The membrane 240 separates an upper microchannel 234 from the lower microchannel 236 in an active region 237, which includes a bilayer of cells in the illustrated embodiment. In some embodiments, a first cell layer 242 is adhered to a first side of the membrane 240, and in some embodiments a second cell layer 244 is adhered to a second side of the membrane 240. The first cell layer 242 may include the same type of cells as the second cell layer 244. Or, the first cell layer 242 may include a different type of cell than the second cell layer 244. And, while a single layer of cells is shown for the first cell layer 242 and the second cell layer 244, either the first cell layer 242, the second cell layer 244, or both may include multiple cell layers or cells in a non-layer structure. Further, while the illustrated embodiment includes a bilayer of cells on the membrane 240, the membrane 240 may include only cells disposed on one of its sides. Furthermore, while the illustrated embodiment includes cells adherent to the membrane, cells on one or both sides may instead be not be adherent to the membrane as drawn; rather, cells may be adherent on the opposing chamber surface or embedded in a substrate. In some embodiments, the said substrate may be a gel.

The OOC device 100 is configured to simulate a biological function that typically includes cellular communication between the first cell layer 242 and the second cell layer 244, as would be experienced in-vivo within organs, tissues, cells, etc. Depending on the application, the membrane 240 is designed to have a porosity to permit the migration of cells, particulates, media, proteins, and/or chemicals between an upper microchannel 234 and a lower microchannel 36. The working fluids within microchannels 234 and 236 may be the same fluid or different fluids. As one example, as OOC device 100 simulating a lung may have air as a fluid in one channel and a fluid simulating blood in the other channel. As another example, when developing the cell layers 242 and 244 on the membrane 240, the working fluids may be a tissue-culturing fluid. Although it is not necessary to understand the mechanism of an invention, it is believed that an organ-on-chip device offers utility even in the absence of cells on one side of the membrane, as the independent perfusion on either side of the membrane can serve to better simulate the functions of mass-transport, shear forces, and other embodiments of the biological environment. In one embodiment, the active region 237 defined by an upper microchannel 234 and a lower microchannel 236 having lengths of about 0.1-10 cm, and widths of about 10-2000 μm.

The OOC device 100 preferably includes an optical window that permits viewing of the fluids, media, particulates, etc. as they move across the first cell layer 242 and the second cell layer 244. Various image-gathering techniques, such as spectroscopy and microscopy, can be used to quantify and evaluate the effects of the fluid flow in an upper microchannel 234 and a lower microchannel 236, as well as cellular behavior and cellular communication through the membrane 240. More details on OOC devices can be found in, for example, U.S. Pat. No. 8,647,861, and is incorporated by reference in its entirety. Consistent with the disclosure in U.S. Pat. No. 8,647,861, in one preferred embodiment, the membrane 240 is capable of stretching and expanding in one or more planes to simulate functions of the physiological effects of expansion and contraction forces that are commonly experienced by cells.

Micro- and mesofluidic devices and membranes can be fabricated from or coated with or otherwise produced from a variety of materials, including, but not limited to, plastics, glass, silicones, biological materials (e.g., gelatin, collagen, fibronectin, laminin, Matrigel®, chitosan, and others).

Turning now to FIGS. 3 through 12 various exemplary open-top microfluidic devices (e.g., open-top OOC devices) and components are illustrated that can be used for creating gel layers, such as for an open-top skin-on-a-chip device or for creating gel layers for an open-top OOC device for simulating other biological functions.

Figure 3:
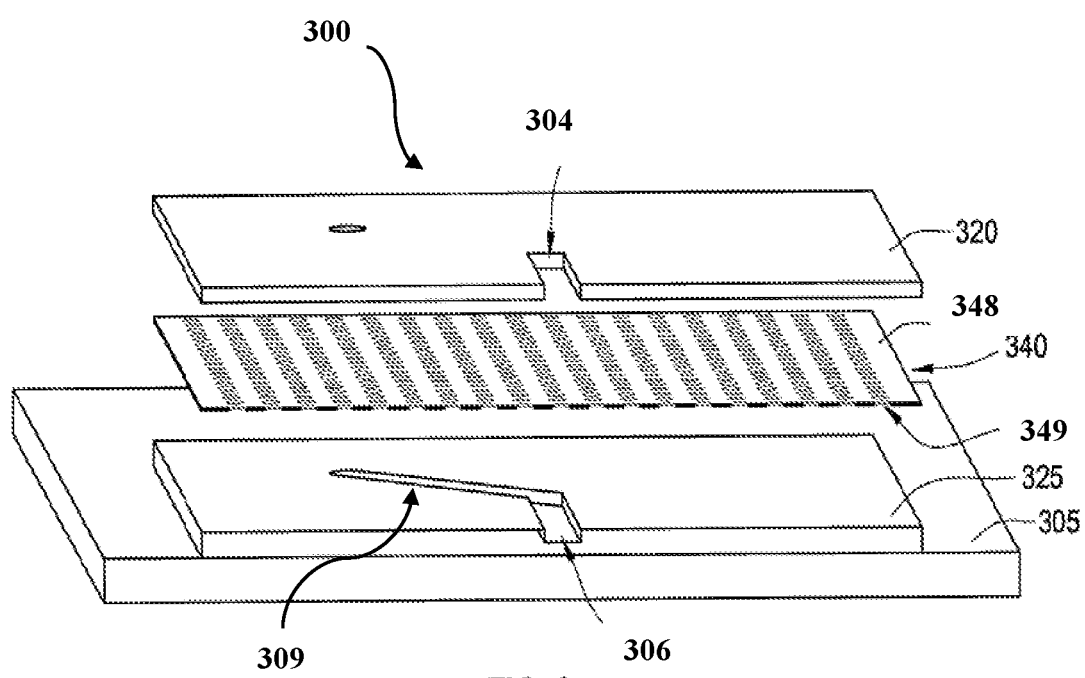
FIG. 3 illustrates an exploded perspective view of an exemplary cross-section through an open-top microfluidic device according to embodiments of the present disclosure.

FIG. 3 illustrates an exploded perspective view of a cross-section through an exemplary open-top microfluidic device 300 (e.g., an open-top OOC device). Open-top microfluidic devices, such as an open-top OOC device, that allow access to the top of a chip offer several benefits. Topical treatment, such as for a skin-on-a-chip, can be applied directly through the open top to the tissue of interest. Topical treatments can include, for example, liquid, gas, gel, semi-solid, solid, particulate or aerosol. Furthermore, additional chemical or biological components can be added by means of the open top; as a particular example, additional cell types can be seeded within the open top of the device. Aerosol delivery, such as for a lung-tissue chip, is also contemplated and can be completed through the open top, as well.

The microfluidic device 300 can optionally include a base 305, such as a glass slide, polymeric or metal support or a similar structure, optionally providing an optical window. The base 305 can support a bottom structure 325 of the microfluidic device 300. The bottom structure 325 defines a bottom chamber 336 connected to a bottom fluidic channel 409 in the microfluidic device 300. Above the bottom structure 325 is a membrane 340 having a membrane top side 348 and a membrane bottom side 349. The membrane bottom side 349 is disposed on the top surface of bottom structure 325 such that membrane bottom side 349 rests above the bottom chamber 306. A top structure 320 is disposed on the membrane top side 348 of membrane 340 and defines an open region 304 for the open-top microfluidic device 300 (e.g., the open-top chip). When the top structure 320 is disposed on the membrane 340, it may be desirable that all or substantially all of the open region 304 is bounded on the bottom by the membrane top side 348 of the membrane 340.

Figure 4:
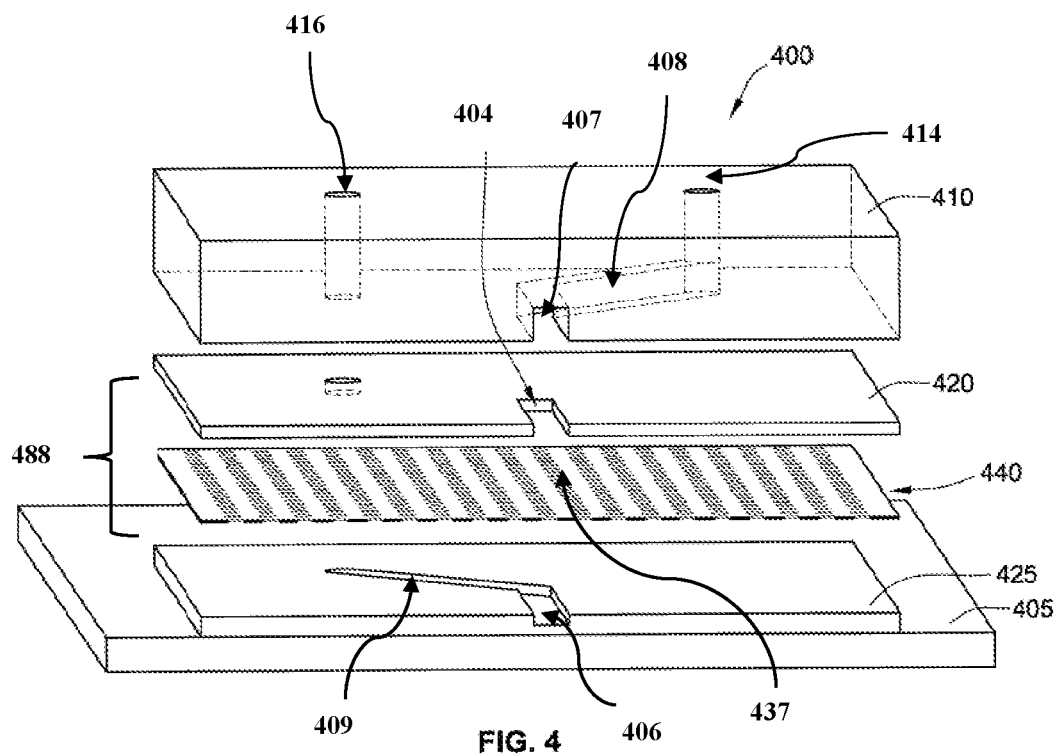
FIG. 4 illustrates an exploded perspective view of an exemplary cross-section through an open-top microfluidic device with a removable cover according to embodiments of the present disclosure.
Figure 5A:
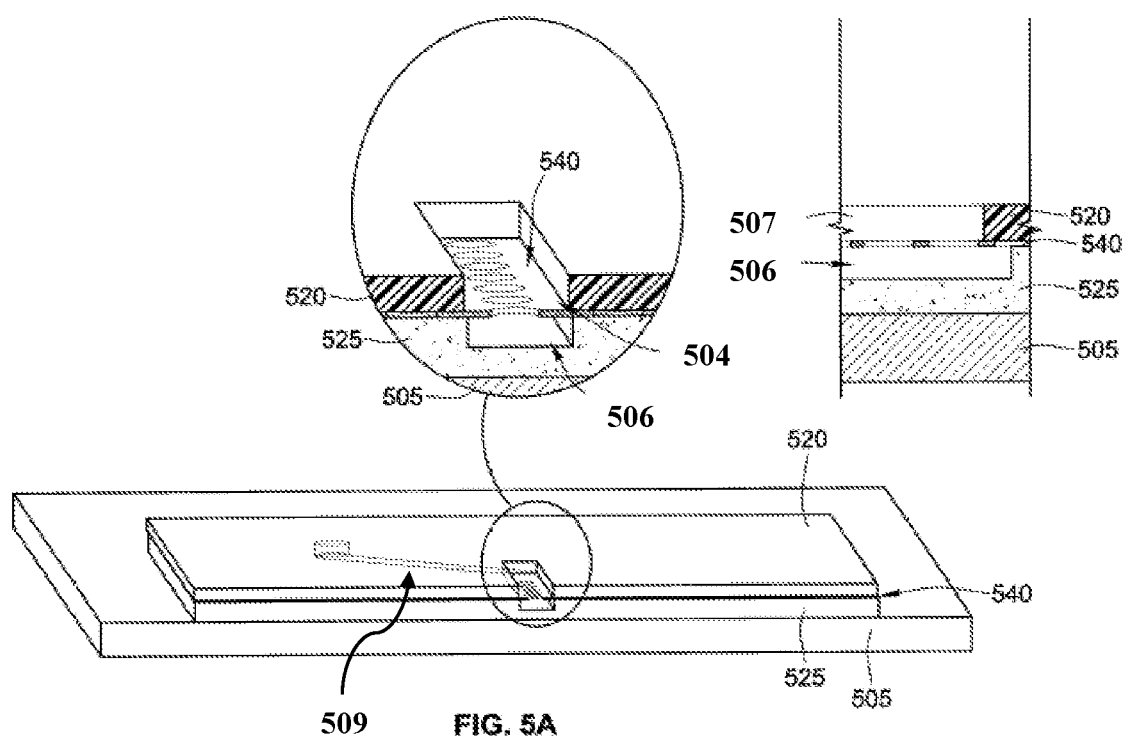
FIG. 5A illustrates a perspective view of an exemplary cross-section through an open-top microfluidic device according to embodiments of the present disclosure.
Figure 5B:
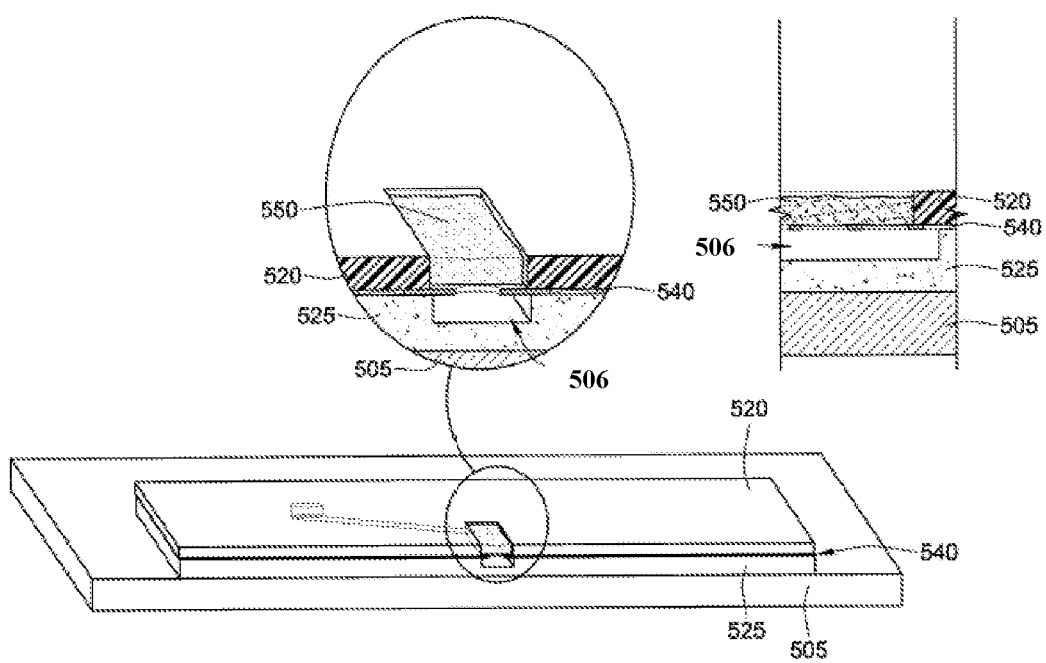
FIG. 5B illustrates a perspective view of the exemplary open-top microfluidic device of FIG. 5A including a gel layer above a membrane layer in an opened region of a top structure according to embodiments of the present disclosure.

In some embodiments, the chamber of the top structure 320 can further include a top microfluidic cover fluidic channel 308 (not shown) such as a top microfluidic cover fluidic channel 508 (e.g., as illustrated in FIG. 5A). In FIG. 5A-F, such a top microfluidic cover fluidic channel 508 may permit perfusion of a top chamber 507, particularly while top chamber 507 is covered by an optional fluidic cover 510 (FIG. 5B). In some embodiments, the present invention contemplates that embodiments one or both of a bottom structure fluidic channel 509 and a top microfluidic cover fluidic channel 508 are microchannels. In some embodiments, the present invention further contemplates that embodiments, an optional fluidic covers, such as fluidic cover 410 or fluidic cover 510 (see, FIGS. 4 and 5A-F, respectively) are disposed above a top structure 520 and may further be in fluid communication with, and define a top chamber 507 and an open region 504. Although it is not necessary to understand the mechanism of an invention, it is believed that a fluidic cover, such as fluidic cover 410, may be designed for a one-time application (e.g. by means of bonding it in place) or for subsequent removal.

An open region 304 in the open-top structure 320 may have any shape, but is preferably a notch. In one embodiment, the purpose of open region 304 is believed to allow direct access to the membrane 340 or any matter disposed above it, before, during, and/or after experimentation; such access is not available in earlier closed microfluidic devices for simulating tissues. While previous microfluidic devices, such as OOC, may have allowed for low viscosity fluids to be directed through limited-access channels to a membrane, such as illustrated in FIGS. 1 and 2, the open region 304 in top structure 320 additionally allows for the placement of high viscosity gels, high viscosity fluids, solids, aerosols, and powders on an area of interest of membrane 340 (e.g., on the membrane inclusive of a predetermined tissue culture).

Turning now to FIG. 4, an exploded perspective view of an exemplary open-top microfluidic device 400 includes a fluidic cover 410. The microfluidic device 400 includes an optional base 405 that supports a bottom structure 425. The bottom structure 425 defines a bottom chamber 406. Above the bottom structure 425 and the bottom chamber 406 is an interface region 488 that comprises a membrane 440. The membrane 440 is disposed on the bottom structure 425 and above the bottom chamber 406. A top structure 420 is disposed above the membrane 440 and includes a top chamber 407 with an open region 404. When the top structure 420 is disposed on the membrane 440 during assembly of the device 400, it may be desirable that all or substantially all of the open region 404 is bounded along the bottom by the membrane 440.

The fluidic cover 410 may be designed to permit the perfusion of the open region 404 while the fluidic cover 410 is present. In some embodiments, the present invention contemplates that this configuration provides an advantage over previous similar devices that allows the perfusion of the open region 404 by way of a top fluidic cover fluidic channel 408 in the top structure 420. One of the benefits of including a top fluidic cover fluidic channel 408 in the fluidic cover 410 instead of the top structure 420, is that cells, gel or other materials disposed in the open region 404 are not allowed to leak or spread into the top fluidic cover fluidic channel 408, where they may be undesirable. For example, cells in the top fluidic cover fluidic channel 408 will not be allowed to lie away from the active region 437 of membrane 440. In contrast, by disposing a top fluidic cover fluidic channel 408 in the fluidic cover 410, a benefit is provided of top fluidic cover fluidic channels 408 being absent when a fluidic cover 410 is removed, which disallows top fluidic cover fluidic channels 408 from being similarly filled with cells during seeding, as would happen with channels being directly disposed in the top structure 420.

To minimize "leakage" of a substance of interest placed into an open region 404 into areas where the substance is not desired, different configurations of the open-top microfluidic device are contemplated. For example, a fluidic cover 410 can include a top chamber 407 (which may be a channel or part thereof) that substantially aligns with all or a portion of the open region 404 cover disposed in top structure 420. The top chamber 407 may optionally be hydraulically connected to one or more fluidic cover inlet ports 414 and/or fluidic cover outlet ports 416 (see also, fluidic cover inlet port 514, FIG. 5D), which in some embodiments may be similar to the ports described for upper body segment 101 in FIGS. 1 and 2. The presence of the top chamber 407 is especially significant where the open region 404 is filled with a gel or other substance that impedes fluid flow. In such a case, the top chamber 407 may be filled or perfused, enabling its contents to fluidically interact with the substance in the open region 404. For example, if the open region 404 holds a gel containing cells, flowing tissue-culture media through the top chamber 407 (or even incubating this media without flow) would allow nutrients and reagents to be delivered to the cells, as well as for waste products to be removed.

Through the use of a clamping device the fluidic cover 410 can be mechanically secured to the top structure 420 (e.g., see FIG. 5E) to prevent or minimize leakage of any fluidic substance of interest from the open region 404 of the open-top microfluidic device 400. For example, a spring-loaded clamp can be used to provide compression to a biocompatible polymer that uniformly seals the open region without adhesives. Such sealing can be further improved by including an elastomeric, pliable or soft material in at least one of the fluidic cover 410 or top structure 420; one with ordinary skill in the art will appreciate that many forms of gasketing and sealing may be applied here. An advantage of some embodiments that employ clamping is that they facilitate the application, removal and potentially the reapplication of a lid or cover, which may desirably allow access to the open region 404 after it was covered. Allowing access to an open region 404 of a microfluidic device during experimentation can be useful, for example, in (i) the application of topical treatment, aerosol, additional cells or other biological reagents, (ii) change of fluidic (e.g. tissue-culture media), (iii) sampling of fluidic or solid matter, or (iv) imaging using optical or other techniques. The option to reposition the cover or apply a different cover further permits the continued use of the device (e.g. in a biological experiment). Alternatively, the lid or cover may be removed at the end of the device's use to permit sampling that may be destructive, such as taking biopsies or otherwise removing samples, staining, fixing, or imaging.

In some embodiments, the present invention contemplates that a fluidic cover 410 can also, or alternatively, be bonded or otherwise disposed onto the top structure 420. For example, for fluidic or gas sealing, an adhesive membrane, laminate, film, or sheet can be used to temporarily or permanently seal the open region at the interface between the top structure that defines the open region and a removable cover. It is also contemplated that biocompatible polymer plugs or pistons can be used to seal off the open region. It is further contemplated that an open region 404 of an open-top microfluidic device 400 can be simply covered (e.g., similar to cell culture plates) with a cover or plate that limits evaporation and improves sterile handling.

In embodiments one embodiment, the present invention contemplates that a top structure 420 can be used with an open region 404, similar to a well, or with a removable fluidic cover 410 that may be akin to a flat layer that seals the top structure 420. An optional configuration in FIG. 4 includes a top chamber 407 with a fluidic cover fluidic channel 408 that can also introduce fluids into the microfluidic device such as for perfusion or the introduction of other liquids into the system.

As discussed above, open-top microfluidic devices described herein offer a number of advantages. For example, these devices allow the topical application of compounds to a membrane, including compounds in the form or a gel or powder. The open-top design also allows for aerosol delivery to effect a simulated function of a tissue directly from the top of the microfluidic device. Furthermore, the open-top configuration allows access to apply simulated effects of wounding to a tissue (e.g., simulate effects of a burn or scratch on the skin or intestine) during the course of testing and the application of a treatment of interest all within the same microfluidic device and as part of the same experimentation cycle.

Furthermore, the open-top configurations described herein also allow direct access to the epithelium, and thus, allow the ability to biopsy a sample during testing. An open-top configuration also allows microscopy to be applied during use of a chip, such as the application of electron microscopy, high-magnification imaging methods, and laser-based imaging methods by removing the top cover of the microfluidic device, while optionally maintaining the integrity of the experiment.

In some embodiments, it is desirable to simulate one or more functions of lung, as such function simulations may be beneficial, for example, in testing compound transport and absorption through the lung, the effect of aerosolized or inhaled compounds, model lung disease, or otherwise observe lung response. In vitro models are known in the art, including for example a lung-on-a-chip microdevice disclosures in U.S. Pat. No. 8,647,861, entitled, "Organ Mimic Device with Microchannels and Methods of Use and Manufacturing Thereof," and the small-airway on-a-chip microdevice disclosures in International Publication No. WO 2015/0138034, entitled, "Low Shear Microfluidic Devices and Methods of Use and Manufacturing Thereof," both of which are hereby incorporated by reference herein in their entireties. A lung model that combines several of desired features in the same model would be beneficial. Desired features include recapitulation of various elements of lung structure and morphology, and the ability to satisfactorily introduce compounds or materials as aerosols, fluidic access (e.g. to emulate blood or air flow), or mechanical forces. For example, a lung model is desirable that minimizes loss of aerosol that can occur in delivery tubing and channels and variation in the aerosol delivery along the length of the channel. According to some embodiments of the present disclosure, a lung model that includes one or more of such desired features can be constructed. For example, in one embodiment, a lung module is constructed using an open-top device, such as that illustrated in FIG. 4 (whether employing a fluidic cover 410, the optional cover of FIG. 3, or no cover). Accordingly, lung epithelial cells (e.g. alveolar epithelial cells) can be included or deposited within the open region 404. Optionally, the bottom structure 425 may include endothelial cells, motivated by the presence of similar cells in the vasculature (e.g. capillary bed) of an in vivo lung. It is also contemplated that using the various embodiments of open-top devices described herein, a lung model may be biologically cultured or operated statically (i.e., for example, without continuous flow or with discrete exchanges of some portion of the liquid in the device) or under flow in either fluidic channels disposed in, for example, the bottom structure 425, top structure 420, or cover 410, as well as any combination of these modalities, which may optionally be varied during operation (e.g. begin with discrete fluid exchanges, then introduce flow). In addition, the open region 404 or cell layers within it may be cultured dry, under an air-liquid interface, or submerged, with this mode of culture optionally varied during use. For example, following the example of the lung-on-a-chip and small-airway-on-a-chip devices, it may be desirable to begin lung culture under submerged conditions and transition to an air-liquid interface culture after some maturation period (e.g. ranging without limitation from 1 hour to 7 days, or from 1 day to 14 days).

A particular advantage of the various open-top embodiments of the present disclosure is that aerosol may be delivered to the lung cells in the open region, such as open region 404. In one exemplary embodiment, while operating the device without the optional cover (or by removing the cover), aerosol can be delivered directly into the open region 404 from above (or substantially above). The aerosol may be generated using any of a variety of aerosol-generation techniques known in the art. Alternatively, an aerosol generation means may be included in a cover that can be placed on top of the open region 404. A cover may be optionally removed or exchanged during use; for example, an aerosol-generating cover may be applied when aerosol is desired and replaced with a fluidic cover 410 when fluidic perfusion is desired. In some embodiments, non-aerosol materials or samples can be applied to cells present in an open region, such as open region 404. This may include, but are not limited to, materials or samples that are difficult to apply fluidically due to their properties, such as slurries, pastes, solids, or viscous fluids.

Referring now to FIGS. 5A-5F, multiple perspective views, including additional cross-sectional details through an exemplary open-top microfluidic device, are illustrated. The microfluidic device 500 includes a membrane 540 disposed between a bottom structure 525 and a top structure 520. The bottom structure defines a bottom chamber 506, 'and the top structure 520 includes a top chamber 506 that defines an open region 504, of the microfluidic device 500. In some embodiments, it is desirable that the open region 504, includes a gel layer 550, comprising a porous volume, or another material for testing (e.g., an extracellular matrix or cells embedded in an extracellular matrix). For example, a gel layer 550 can include gels used in an organ-on-chip model of the skin to house fibroblasts and to support a layer or keratinocytes. In FIG. 5B, a gel layer 550 is introduced into the open region 504 (see FIG. 5A) where the gel layer 550 is bounded on the bottom by membrane 540.

Figure 5C:
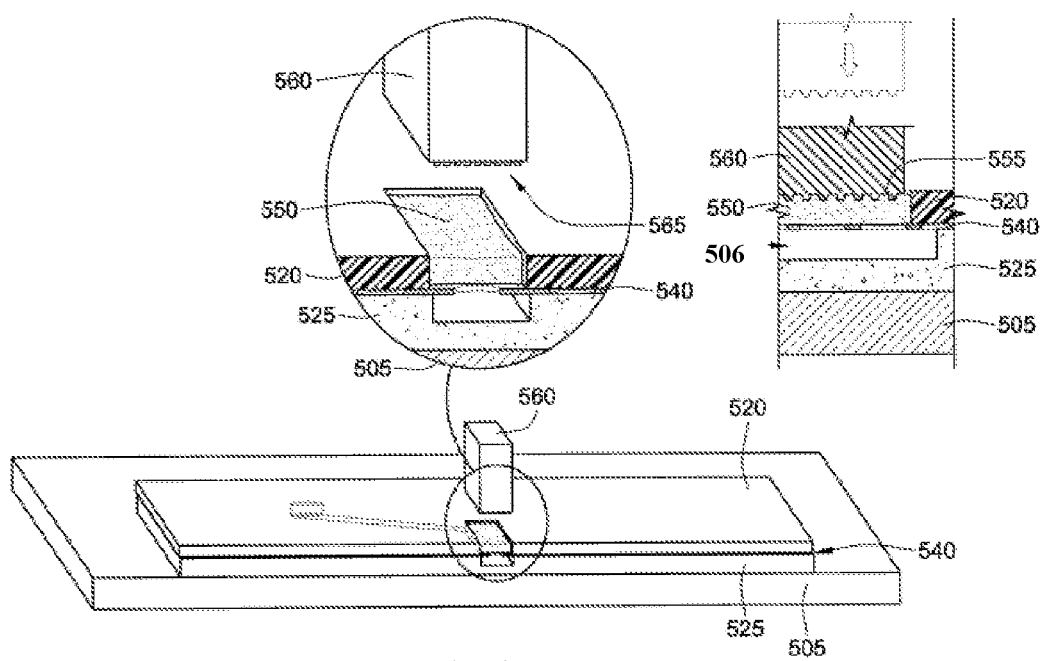
FIG. 5C illustrates a perspective view of the exemplary open-top microfluidic device of FIG. 5B including placement of a plunger stamp into the opened region of the top structure according to embodiments of the present disclosure.

In some embodiments, a gel layer 550, or porous volume, is formed by injecting one or more suitable precursors through one or more fluidic channels included in the top structure 520 (such optional channels are depicted in FIGS. 5A-5C). The one or more precursors can then be treated as desired to form the gel or porous volume (e.g. UV light, chemical treatment, temperature treatment and/or incubation/waiting). Alternatively, the one or more precursors are in a final or near-final form, where no additional active process is applied in order to generate the gel or porous volume. While the approach of injecting the one or more precursors through one or more fluidic channels included in the top structure 520 can be adapted to permit consistent filling with gel or other porous volume, it typically results in the gel or porous volume filling at least part of the said fluidic channels. This may be undesirable in some situations; for example, when dealing with a gel containing cells, it is desirable to limit the cells to the active region, lest they may not receive sufficient nutrient or biochemical cues through the membrane.

Alternatively, the one of more precursors can be placed into the top of the open-top microfluidic device via the open region 504. Such an approach permits alternative embodiments that eliminate or limit spaces into which the precursors may spread (e.g. one may avoid fluidic channels included in the top structure 520 that are in fluidic communication with the open region 504). In other embodiments, the one or more precursors may be injected into the open region 504, by means of a fluidic cover 510 that includes one or more fluidic cover fluidic channels 508 (an example is illustrated in FIG. 5D). Although such embodiments may also result in a gel layer 550 formed in the fluidic cover fluidic channels 508, the fluidic cover 510 can be removed and optionally replaced, removing at least part of the undesired material.

In some embodiments, it is desirable to limit or shape the gel volume or porous volume. For example, in an organ-on-chip model of the skin, it is may be desirable to limit the thickness of a gel layer housing fibroblasts and supporting keratinocytes to a selected thickness. Without limitation, such thickness may be chosen from one or more of the ranges of 10 um to 200 um, 100 um to 1 mm, 0.5 mm to 5 mm, or 1 mm to 10 mm. According to some embodiments, the extent of a gel layer 550, or porous volume, may be limited by a shaping device 559 (e.g., a shaping cover, a plunger 560 with a patterned base) that is present during the introduction or formation of the gel or porous volume. This shaping device 559 may be removed and optionally replaced with a cover (e.g., a fluidic cover 510) once a gel layer 550, or porous volume, has formed. The shaping device 559 may optionally include a chamber into which the gel or porous volume can conform, at least in part. Alternatively, a shaping device 559 may include one or more features that protrude into the open region 504. FIG. 5C illustrates one type of a shaping device with features that protrude into the open region 504, which takes the form of a plunger stamp 560. In some embodiments, shaping devices are applied before the introduction of one or more precursors for a gel or porous volume; for example, it could be introduced through fluidic channels present in the top structure 520, a fluidic cover 510 or even in the shaping device itself. In other embodiments, the one or more precursors are introduced before the application of the shaping device, whether through fluidic channels in the top structure 520 or fluidic cover 510, or introduced directly into the open region 504 (e.g. using a syringe, pipette or printing process). In such cases, the shaping device may optionally include features (e.g. holes, fluidic channels, cavities) designed to allow the capture of excess precursor. In some embodiments, the shaping device comprises a plurality of layers. For example, the shaping device may include a spacer layer used to define gel height and a flat cover to prevent the gel from passing the spacer's height. All or only a subset of these layers may be removed once the gel or porous volume is defined, with the remaining layers (e.g. spacer layer) potentially remaining during device use or experimentation. In some embodiments, the top structure 520 may be removed after gel or porous volume formation, and can be optionally replaced with a different structure or cover, that may or may not include an open region.

In one embodiment, the present invention contemplates a gel layer 2050 comprising a plurality of gel micropillars 2053. FIG. 20A. For example, such gel micropillars 2053 may be arranged in symmetrical rows along the surface of the gel layer 2050. FIG. 20B.

In one embodiment, the present invention contemplates a gel layer formed as a gel mesh 2054. FIG. 20A. For example, such a gel mesh 2054 may be formed as an insert within a top chamber 2006 or bottom chamber 2007. FIG. 20B.

In one embodiment, the present invention contemplates a shaping device comprising a plunger stamp 560 having a patterned surface 665 that creates a pattern in the gel or porous volume at a patterning interface 555. Depending on the properties of the precursor materials (e.g. viscosity of the precursor and its change through curing), the shaping device may be removed before the gel or porous volume have fully formed.

FIG. 5D next illustrates a perspective view of the exemplary open-top microfluidic device of FIG. 5C after a plunger stamp 560 has been removed, including a patterned top surface 557 in the gel layer 550. The patterning includes depressions 558 in the patterned top surface 557 of the gel layer 550. The removable fluidic cover 510 can then be placed onto microfluidic device 500 such that top chamber 507 aligns with bottom chamber 506. An exemplary fluidic cover 510 can optionally include fluidic channels. In the example illustrated, one of the fluidic channels 508 extends from inlet hole 514 to the top chamber 507. An outlet fluidic chamber 515 ends at outlet hole 516 wherein the outlet fluidic chamber 515 extends downwardly through the fluidic cover 510, and connects through an opening in the membrane 540, such that it is fluidically connected with chamber 506. The fluidic cover 510 may be removable, and once removed it may be optionally reapplied or optionally replaced with a different cover.

Figure 5E:
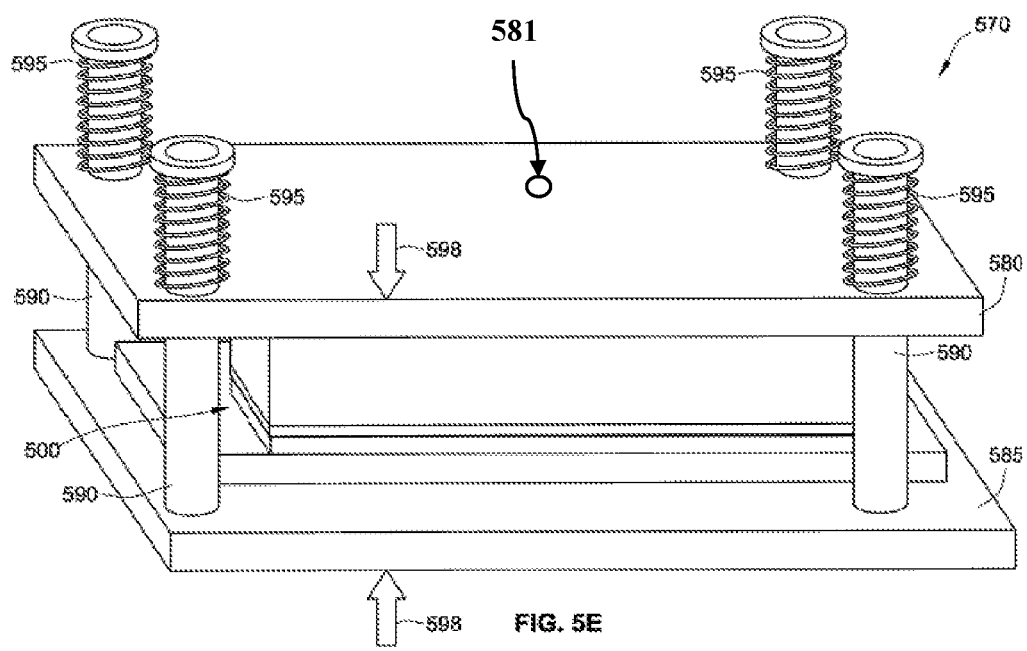
FIG. 5E illustrates a perspective view of the exemplary open-top microfluidic device of FIG. 5D in an exemplary clamping device according to, embodiments of the present disclosure.

FIG. 5E illustrates the exemplary open-top microfluidic device disposed within an exemplary clamping device 570. A clamping device 570 can be desirable because no glue or bonding is needed to hold the various layers of the microfluidic device together. The clamping device applied to an open-top microfluidic device optionally allows efficient removal of the removable cover during an experiment. The clamping device 570 for the microfluidic device 500 can include an optional platform 585 for engaging a first side (e.g., the bottom side) of the microfluidic device 500. In some embodiments, a plurality of elongated posts 590 can extend upwardly from the platform 585. A compression plate 580, which may flat or may in some embodiments be uneven, is movably coupled to the plurality of elongated posts 590 such that the compression plate 580 is vertically slidable along the posts 590. In some embodiments, the compression plate 580 engages a second side (e.g., the top side) of the microfluidic device 500; in other embodiments, the compression plate 580 retains a cover to the microfluidic device 500. A compression device 580 provides compressive forces (e.g., see arrows 598) generally in a direction along the elongated posts 590. The compression device (e.g., springs 595, elastomers, flextures, etc.) is operatively connected to the compression plate 580 such that the compressive forces (e.g., see arrows 598) create a substantially uniform pressure on the second side (e.g., the top side) of the microfluidic device 500. Clamping device components can be made from different types of materials, including, but not limited to, PMMA (e.g., acrylic), thermoplastics, thermoset polymers, other polymer materials, metals, wood, glass, or ceramics. In alternate embodiments, the compressive plate 580 may be held in place using a retention mechanism including, but not limited to, one or more of screws, clips, tacky/sticky materials, other retention mechanisms known in the art, or the combination of any of these mechanisms and/or the aforementioned compression device. In some embodiments, a retention mechanism retains a compressive plate 580 with respect to or against a platform 585. In alternate embodiments, a retention mechanism retains a compression plate 580 with respect to or against a microfluidic device 500. For example, screws can be used to fasten a compression plate 580 against a microfluidic device 500 with a corresponding threaded holes included in a microfluidic device 500. As another example, a compression plate 580 can include a clip feature (as a retention mechanism)

that clips into a suitable receiving feature of a microfluidic device. In some embodiments, that compression plate 580 comprises a cover for an open area included in a microfluidic device 500. In other embodiments, a compression plate 580 retains an additional substrate that comprises a cover for an open area included in a microfluidic device 500.

In some embodiments, a compression plate 580 may include at least one access hole 581 that substantially aligns with a corresponding fluid port (e.g., inlet hole 514 or outlet hole 516) on a microfluidic device 500 or an optional cover. In some embodiments, an access hole 581 securely holds or comprises a fluid connector. Such a fluidic connector may be beneficial in fluidically interfacing with a microfluidic device 500 or optional cover without necessitating that a connector be included in a microfluidic device 500 or optional cover.

A bottom surface area of the compression plate 580 may be greater or smaller than a top surface area of the microfluidic device 500. In some embodiments, the platform 585 can have a width such that the compression plate width is greater than the base width. The compression plate 580 can further include finger nubs or tabs (not shown) protruding from a central portion of the compression plate and extending beyond the base such that a compression plate width with the finger nubs is greater than the base width.

In embodiments that include elongated posts 590, it is contemplated that the plurality of elongated posts 590 are substantially parallel and the compression plate 580 includes a plurality of apertures operative to allow an elongated post to pass through a respective aperture. The plurality of elongated posts 590 supports the compression device (e.g., springs 595). The compression device can include at least one spring 595 extending around an outer boundary of at least one of the plurality of elongated posts 590. In some embodiments, a compression plate 580 comprises two springs 595 that provide a substantial uniform or equalized pressure to a compression plate where a compression plate is a mobile part of the clamping device 570 that moves easily up and down (or along other axes) to allow for easy manipulation of the clamped system. For example, the use of springs in a clamping device can be desirable because springs constants can provide for a wide range of translation distances and forces and are versatile for situations where a clamping device may be positioned upside down for extended periods of time. A compression plate 580 can be modified in area, shape, thickness, or material.

Although it is not necessary to understand the mechanism of an invention, it is believed that a maximum compressive force provided to a microfluidic device by a clamping device is determined based on the force required to create a fluidic seal between a compression plate 580 or optional cover and a microfluidic device 500 (if such a seal is desired), and a propensity for the collapse of microfluidic channels or chambers within the microfluidic device 500 or optional cover. In some embodiments, compressive forces provided can range from approximately 50 Pa (approximately 0.007 psi) to approximately 400 kPa (approximately 58 psi). In some embodiments, compressive forces provided can range from approximately 5 kPa (0.7 psi) to approximately 200 kPa (29 psi). In some embodiments, it is desirable that the amount of force or pressure applied by a compression plate 580 to a microfluidic device 500 keep a microfluidic device sealed or properly sandwiched between the compression plate 580 and a platform 585 while not being so extreme as to cause the collapse of the microfluidic channels or to prevent desired gas exchange.

A glass slide or other transparent window (e.g. made of PMMA, polycarbonate, sapphire, etc.) can be integrated into a clamping device 570 to provide a rigid support for the microfluidic device which improves pressure distribution for flexible devices (such as those made from PDMS silicone) while enabling good optical access for macroscopic, visual, or microscopic imaging that may be desirable through viewing portions of the clamp system.

In one embodiment, the present invention contemplates that the described clamping device can facilitate the use or positioning of the device in an upside down position. This can be a particularly desirable feature during cell seeding of the underside of a chip membrane, commonly done during OOC co-culture. A compression device for the clamping device 570 can include alternatives to springs or other aforementioned compression devices or retention mechanisms. For example, hydraulic or pneumatic compression systems are contemplated. It is also contemplated that for rigid microfluidic devices compliant gaskets can be used. For example, the clamping device 570 can be fitted with a compliant gasket that has a level of springiness to it rather than a spring itself. The compliant gasket materials would create an interface between the compression plate 580 and the microfluidic device 500 or between an optional cover and the microfluidic device 500. It is also contemplated that in some embodiments a compression device can utilize geometric shapes, such as cantilevered beams, as part of the device design to provide compressive force resulting from the case material flexure or compression. In some embodiments, the compressive force can also be provided with magnetic or electromagnetic systems.

Figure 5F:
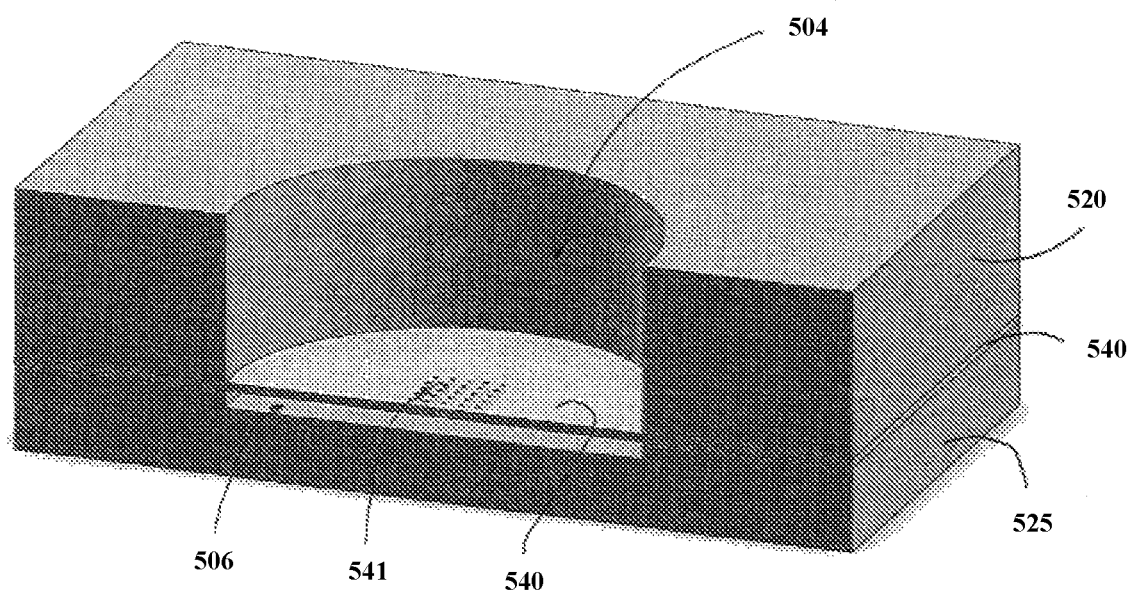
FIG. 5F illustrates a perspective view of an alternative exemplary cross-section through an open-top microfluidic device according to embodiments of the present disclosure.

FIG. 5F illustrates a perspective view of an alternative exemplary cross-section through an open-top microfluidic device, similar to device 500, with a bottom chamber 506 and open region 504 that are generally circular from a top or bottom view perspective. Other embodiments can include an oval or football shape. Another exemplary feature includes a membrane 540 disposed between the bottom structure 525 and the top structure 520, where the bottom structure defines the bottom chamber 506 and the top structure defines the open region 504. The illustrated membrane 540 limits passage between the channels (e.g., the open region 504 and the bottom chamber 506) to a plurality of holes 541 that in some embodiments comprise less than the entire surface area of the membrane 540 within the open region 504 and bottom chamber 506. The plurality of holes 541 may include laser cut holes for passage of a gel, a porous volume, or another material (e.g., an extracellular matrix or cells embedded in an extracellular matrix) that has been disposed in the open region for testing.

In some embodiments, an open-top microfluidic device allows for the direct deposition of a matrix, for example a gel or a porous volume or a biodegradable polyester such as polycaprolactone, into the open region or open portion of an open-top microfluidic device. For example, a gel-forming solution or precursor can be placed in a mold that is separate from the microfluidic device. The mold can approximate the shape of the chamber or open region into which the gel volume will be disposed for a desired experiment. Similar to setting a gel layer 550 directly into the microfluidic device 500 (see FIGS. 5C-5D), a plunger stamp 560 is placed into the gel solution in the mold such that a bottom surface of the plunger stamp is in contact with the gel solution in the mold. The bottom surface of the plunger stamp includes the pattern of features 555 for imprinting into the gel solution. After the gel solution has at least partially solidified, the plunger stamp is then removed from the gel solution, thereby creating a patterned gel surface 557 to simulate the functions of a tissue microstructure. Once the gel has solidified to the point where the gel will not break apart or otherwise separate, the patterned gel can be removed from the mold and be inserted into the similarly shaped open region of the actual microfluidic device to be used for experimentation. Alternatively, or in combination, a suitably shaped volume or gel or porous volume can be cut to size, 3D printed or aggregated from smaller volumes, then disposed into the open region. Further, a gel or porous volume can be 3D printed directly into the open region. In another related embodiment, a matrix (e.g., gel or porous volume) such as one formed as described for FIGS. 5C-5D, can also be easily extracted (whether whole or in part) from the top structure of an open-top microfluidic device, which provides benefits by overcoming the problem of staining and high-resolution imaging without having to stain an entire chip or having to reconstruct cell-monolayers. The removal or insertion of a gel, porous material and/or biological sample (e.g. biopsy, blood) to or from the open region of an open-top microfluidic device is also desirable because it can allow access for testing of the subject tissue sample in the microfluidic device and/or then the subsequent removal of the sample from an OOC device, which can then be used for other applications (e.g., for implantation into a patient; additional analysis in another device). In an alternative embodiment, the gel or gel containing cells or tissue can be patterned following culture of cells in the gel material.

In some embodiments of a microfluidic device, it is desirable to include a cover that comprises sensors or actuators. For example, a cover can comprise one or more electrodes that can be used for measurement of electrical excitation. In some embodiments, such as where the device comprises a membrane (e.g., membrane 540), the one or more electrodes can be used to perform a measurement of trans-epithelial electrical resistance (TEER) for the membrane. It may also be desirable to include one or more electrodes on the opposite side of the membrane 540. In some embodiments, the electrodes can be included in a bottom structure (e.g., bottom structure 525). In some embodiments, the bottom structure can be an open bottom with bottom electrodes included on a bottom cover that can be brought into contact with the bottom structure. The bottom cover may support any of the features or variations discussed herein in the context of a top cover, including, for example, removability, fluidic channels, multiple layers, clamping features, etc.

In some embodiments, it is desirable to simulate one or more functions of skin, for example, in testing compound transport and absorption through the skin, the effect of topical treatments on skin aging or healing, modeling skin disease, or observing skin response such as damage or sensitization. While in vitro skin models are known, such as living skin equivalent (LSE), a skin model that combines several features in the same model would is desirable. For example, desirable features can include recapitulation of various elements of skin structure and morphology, topical access, fluidic access (e.g. to emulate blood flow), or mechanical forces. According to some embodiments of the present invention, a skin model that includes one or more of such desired features can be constructed. In one exemplary embodiment, the skin model is constructed using the open-top device illustrated in FIG. 5D. Accordingly, a gel layer 550, which may be considered to correspond to the skin's dermal layer, is present in or introduced into (e.g. using any of the aforementioned methods) the open region 504. Optionally, the gel layer 550 (or other matrix) may include embedded fibroblasts or related cells, motivated by the presence of similar cells in the dermal layer of in vivo skin. Furthermore, the gel layer 550 is topped by keratinocytes, which are a primary cell type of the skin. The keratinocytes may, for example, be deposited on top of the gel layer 550 (which can be done, for example, directly through the open top or introduced fluidically through channels present in the top structure 520 or cover 510) or present in the gel or other device component and allowed to biologically mature or develop into a cell layer at the top of the gel layer 550. Optionally, the bottom structure 525 includes endothelial cells, motivated by the presence of similar cells in the vasculature (e.g. capillary bed) of in vivo skin. Using various embodiments of the open-top device described herein, the resulting skin model may be biologically cultured or operated statically (i.e., for example, without continuous flow or with discrete exchanges of some portion of the liquid in the device) or under flow in either fluidic channels disposed in the bottom structure 525 top structure 520 or cover 510, as well as any combination of these modalities, which may optionally be varied during operation (e.g. begin with discrete fluid exchanges, then introduce flow). In addition, the open region 504 or cell layers within the open-top microfluidic device may be cultured dry, under an air-liquid interface, or submerged, with this mode of culture optionally varied during use. For example, following the example of prior skin models such as the LSE, it may be desirable to begin keratinocyte culture under submerged conditions and transition to an air-liquid interface culture after some maturation period (e.g. ranging without limitation from 1 hour to 3 days, or from 1 day to 14 days). The gel layer 550 may comprise a biological or synthetic gel or other porous volume, including for example, collagen I, collagen IV, fibronectin, elastin, laminin, gelatin, polyacrylamide, alginate, or Matrigel®. Collagen I in particular has been used by prior skin models, whereas it is known that elastin is present in in vivo skin, motivating its use in the disclosed in vitro model.

In some embodiments, it can be similarly desirable to simulate one or more functions of the intestine, for example, in testing compound transport and absorption through the intestine or its parts, the effect of treatments on intestine health or healing, modeling intestinal disease, or observing intestinal response such as damage or sensitization. In vitro intestinal models are known in the art, including for example transwell-based systems or the gut-on-a-chip microdevice disclosures in U.S. Patent Publication No. 2014/0038279, entitled "Cell Culture System," which is incorporated by reference herein in its entirety. In some embodiments, it is desirable construct an intestinal model that combines several of the desired features in the same model, including recapitulation of various elements of intestinal structure and morphology, fluidic access (e.g. to emulate luminal transport or blood flow), or mechanical forces. According to some embodiments of the present disclosure, an intestine model that includes one or more of such desired features can be constructed. In one exemplary embodiment, the intestine model is constructed using the open-top device illustrated in FIG. 5D. Accordingly, a gel layer 550, is present in or introduced into (e.g. using any of the aforementioned methods) the open region 504. Furthermore, the gel layer 550 is topped by intestinal epithelial cells. The intestinal epithelial cells may, for example, be deposited on top of the gel layer 550 (which can be done, for example, directly through the open top or introduced fluidically through channels present in the top structure 520 or cover 510) or be present in the gel or other device component and allowed to biologically mature or develop into a cell layer at the top of the gel layer 550. Optionally, the bottom structure 525 includes endothelial cells, motivated by the presence of similar cells in the vasculature (e.g. capillary bed) of in vivo intestines. Optionally, the gel layer 550 includes cells, for example, smooth muscle cells, neuronal cells, lymphatic cells or other cells types, cultures within the gel layer 550. Using various embodiments of the open-top device described herein, the resulting model may be biologically cultured or operated statically (i.e., for example, without continuous flow or with discrete exchanges of some portion of the liquid in the device) or under flow in either fluidic channels disposed in the bottom structure 525 top structure 520, or cover 510, as well as any combination of these modalities, which may optionally be varied during operation (e.g. begin with discrete fluid exchanges, then introduce flow). Although cells of the intestine are typically cultured submerged, the open-top device also permits the open region 504 or cell layers within it to be cultured dry or under an air-liquid interface, to simulate intestinal gas or various pathologies (e.g. swallowed air or gas presence with irritable bowel syndrome or lactose intolerance), or cultured with highly viscous or solid particulate material (e.g., food, fecal matter, etc.) with the mode of culture optionally varied during use. The gel layer 550 may comprise a biological or synthetic gel or porous volume, including for example, collagen I, collagen IV, fibronectin, elastin, laminin, gelatin, polyacrylamide, alginate, or Matrigel®.

It some embodiments, it can be similarly desirable to simulate one or more functions of the small airway, for example, in testing compound transport and absorption through the airway or its parts, the effect of treatments on airway health or healing, modeling airway disease, or observing airway response such as damage or sensitization. In vitro small airway models are known in the art, including for example the small-airway on-a-chip microdevice disclosures in International Publication No. WO 2015/0138034, entitled, "Low Shear Microfluidic Devices and Methods of Use and Manufacturing Thereof," which is hereby incorporated by reference herein in its entirety. According to some embodiments of the present disclosure, a small-airway model can be constructed to include one or more desired features, including for example fluidic access to airway and vasculature, several of the differentiated cell types found in the in vivo airway (e.g. ciliated cells, mucus-producing cells), and immune response. In one exemplary embodiment, the small-airway model is constructed using the open-top device illustrated in FIG. 5D.

Accordingly, a gel layer 550, is present in or introduced into (e.g. using any of the aforementioned methods) the open region 504. Furthermore, the gel layer 550 is topped by small-airway epithelial cells. The small-airway epithelial cells may, for example, be deposited on top of the gel layer 550 (which can be done, for example, directly through the open top or introduced fluidically through channels present in the top structure 520 or cover 510). Optionally, the bottom structure 525 includes endothelial cells, motivated by the presence of similar cells in the vasculature (e.g. capillary bed) of in vivo airway. Using various embodiments of the open-top device described herein, the resulting model may be biologically cultured or operated statically (without continuous flow or with discrete exchanges of some portion of the liquid in the device) or under flow in either fluidic channels disposed in the bottom structure 525, top structure 520, or cover 510, as well as any combination of these modalities, which may optionally be varied during operation (e.g. begin with discrete fluid exchanges, then introduce flow). In addition, the open region 504 or cell layers within it may be cultured dry, under an air-liquid interface, or submerged, with this mode of culture optionally varied during use. The gel layer 550 may comprise a biological or synthetic gel or porous volume, including for example, collagen I, collagen IV, fibronectin, elastin, laminin, gelatin, polyacrylamide, alginate, or Matrigel®.

In some embodiments, it is desirable to provide mechanical strain or force to at least a portion of the fluidic device. In particular, it may be desirable to apply mechanical force to at least some cells present within the fluidic device. According to some embodiments, a mechanical force is applied to at least one portion of an open-top device by incorporating an actuation mechanism. In some embodiments, this actuation mechanism can include one or more operational channels, similar to ones described by U.S. Pat. No. 8,647,861, which is hereby incorporated by reference herein in its entirety. Such operational channels can be evacuated or pressurized to cause the application of force to a portion of the device, for example, a membrane separating a top and bottom fluidic channels. In this example, any cells present on top or below the membrane may experience the mechanical force, leading to a potential biological effect. In some embodiments, an open-top device is included in a system that additionally includes an actuation mechanism. In some embodiments, this actuation mechanism comprises a system for mechanically engaging the open-top device and a system for applying a stretch or compression force. A number of examples of actuation systems included in a fluidic device or in systems that include a fluidic device are described by International Application No. PCT/US2014/071570, filed Dec. 19, 2014, entitled "Organomimetic Devices and Methods of Use and Manufacturing Thereof", which is hereby incorporated by reference herein in its entirety. In one exemplary embodiment, a system comprises an open-top device, a mechanical engaging device including one or more clamps or pins, and a mechanical actuation device including one or more electrical motors or pneumatic cylinders. According to one method to employ such a system, the open-top device is engaged with the mechanical engaging mechanism (e.g. by slipping the one or more pins into corresponding holes included in the open-top device), and actuating said one or more electrical motors or pneumatic cylinders to apply a cyclical mechanical force on at least part of the open-top device.

Figure 6:
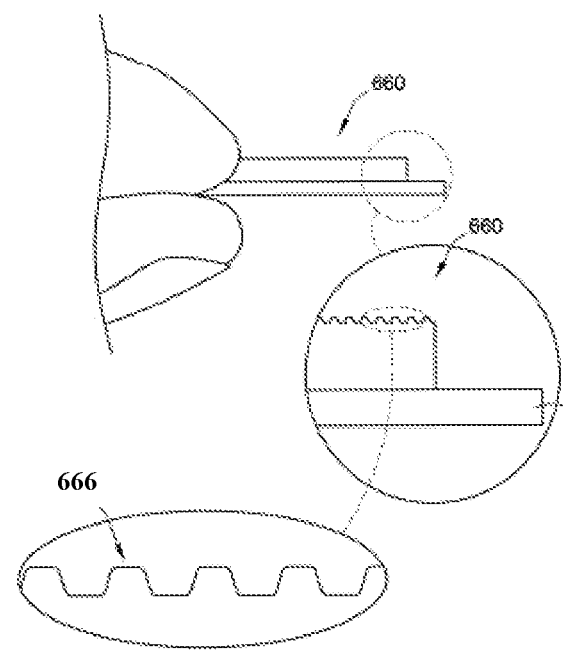
FIG. 6 illustrates an exemplary plunger stamp with a patterned surface according to embodiments of the present disclosure.

Turning now to FIG. 6, another exemplary shaping device 560 (in this case a plunger stamp 660) with a textured bottom surface 666 is illustrated for simulating biological conditions in an open-top microfluidic device (e.g., an open-top OOC device). The plunger stamp 660 can be used in a similar manner as illustrated in FIGS. 5C and 5D. Plunger stamps can also be used to create gel layers of a defined thickness in the open region of an open-top microfluidic device. This can be particularly beneficial where a separate section or layer may be needed to introduce a dermal equivalent layer, such as a collagen plus a fibroblast. A plunger stamp can also be beneficial for skin development in, for example, an open-top OOC device, by allowing the creation of a thick gel layer (e.g., about 50 micrometers to about 10 millimeter thick, about 100 micrometers to about 1 millimeter thick), such as for an in vivo skin section. The plunger stamp can also be used in applications where cells are embedded into a system, such as an ECM with the introduction of cells into the matrix. Application of a plunger stamp to a gel in an open region of an open-top microfluidic device also allows for the embedding of fibroblasts into the gel layer.

Patterned surfaces created with a shaping device (e.g. plunger stamp) can provide for more accurate simulation of tissue or organ characteristics, such as for skin tissue, small-airway tissue and intestine. For example, a gel layer for a skin model can be formed to be undulating, with the undulations mimicking features of in vivo papillae or rete peg structures. Such structures are hallmarks of in vivo skin and can vary with skin health and age. Accordingly, the ability to form and control structures in the open-top chip that mimic in vivo structures is a beneficial embodiment of the disclosed open-top microfluidic systems. As a further example, patterning using a shaping device (e.g. plunger stamp 660) can be used to recreate structure in an intestinal model that mimic intestinal villi. Villi are understood to be a predominant cellular structure of the in vivo intestine, as amongst other things, they are believed to correspond to a villus-crypt axis of cell differentiation. An ability to controllably form structures that mimic villi in an intestinal model is another beneficial embodiment of the disclosed open-top microfluidic systems.

A type of pattern formed on a gel or porous volume may also determine if desired cell types will form in, or on, the said gel or porous volume. For example, adult keratinocyte cells may not differentiate and may die if the anatomy of the gel does not sufficiently simulate the cells' native environment. Using a patterned shaping device (e.g. patterned plunger stamp 660) that allows the imprinting of specific and sophisticated patterns (e.g., patterning and/or geometries simulating the native environment for cells being cultured) into the gel or porous volume surface, a desirable microenvironment can be created that may allow for cell survival and cell differentiation.

Figure 7:
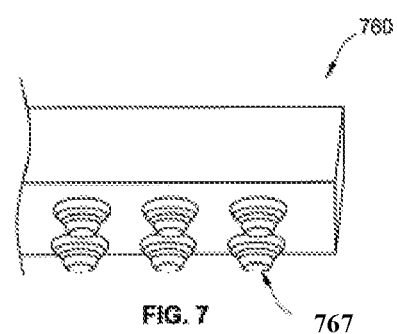
FIG. 7 illustrates an exemplary pattern for a plunger stamp according to embodiments of the present disclosure.

Turning now to FIG. 7, an exemplary pattern for a plunger stamp 760 is illustrated. The plunger stamp 760 includes a patterned bottom surface with a plurality of papillae structures 767 that simulate the papillae structure of the dermis, which when imprinted into the surface of a gel layer can be useful for differentiation of an adult skin equivalent.

In some embodiments, a gel layer is first placed into an open region of a top structure of a microfluidic device or placed into a mold (e.g., simulating an open region) followed by stamping of a gel surface with a plunger stamp. In other embodiments, a plunger stamp is first inserted into an open region to a predetermined desired based on a desired gel layer thickness and a pre-polymerized gel with a lower-viscosity than in its final cured form is placed or allowed to flow into an open region confined by a plunger stamp, a membrane, and the sides of the open region. A plunger stamp is dimensioned such that there are sufficient tolerances (e.g., gaps) between the side of a plunger stamp and the side walls of an open region (e.g., channel) so that a gel does not ooze or leak up the side of an open region when a pre-polymerized gel is imprinted with a patterned surface of a plunger stamp.

Figure 8A:
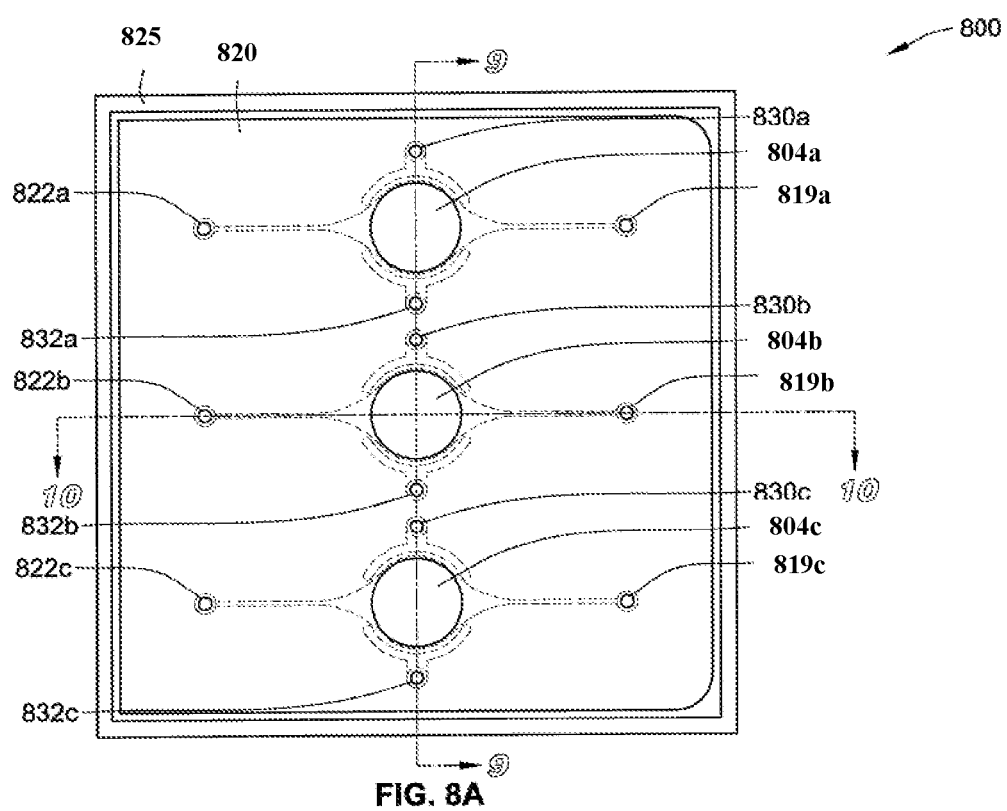
FIG. 8A illustrates a top view of an exemplary stretchable open-top microfluidic device according to embodiments of the present disclosure.
Figure 8B:
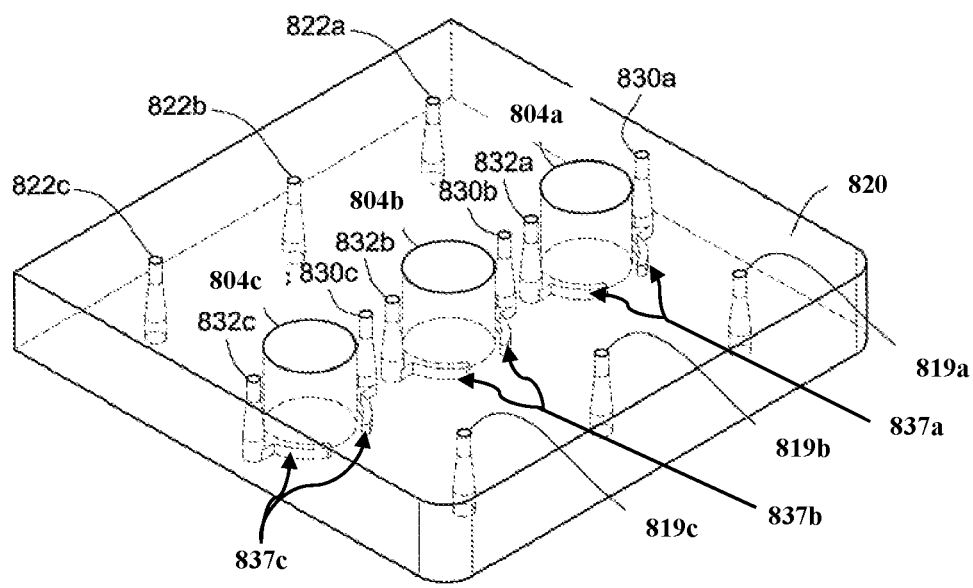
FIG. 8B illustrates a perspective view of the chip top of the exemplary stretchable open-top microfluidic device of FIG. 8A.
Figure 8C:
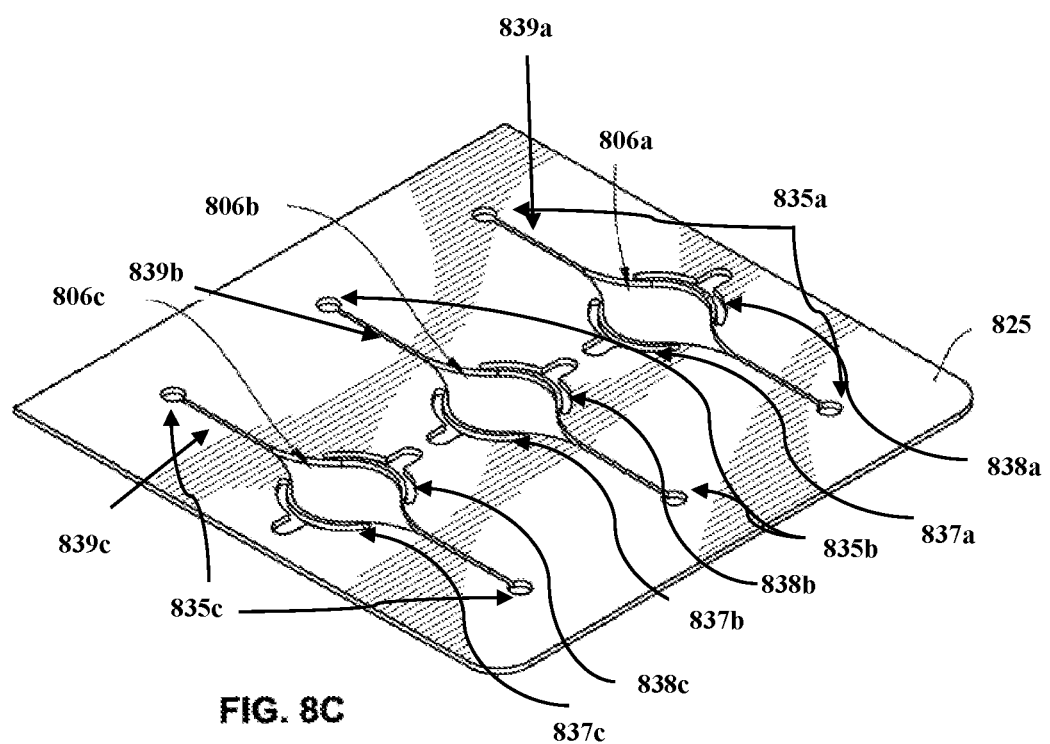
FIG. 8C illustrates a perspective view of the chip bottom of the exemplary stretchable open-top microfluidic device of FIG. 8A.

Referring now to FIGS. 8A-C-10, an exemplary embodiment of an open-top device 800 including round open regions 804a, 804b, 804c is illustrated. The round open regions 804a, 804b, 804c offer advantages in the use of the device. For example, the device is amenable to biopsy with round biopsy punches typical for in vivo work, there is broad area available for topical treatments or experimental procedures, and they may provide a more isotropic biological environment than, for example, elongated sections. A more isotropic environment can be especially beneficial when present cells affect contractile or expansive forces, as is often the case with fibroblasts such as those present in the dermal-like layer of skin models. Although the depicted embodiments in FIG. 8A-C are round, some of the aforementioned advantages also apply to other shapes, including for example ovals, shapes that inscribe round sections, or other broad shapes.

FIGS. 8A-C-10 specifically illustrate stretchable embodiments of an open-top microfluidic device 800. A stretchable open-top microfluidic device, such as the one illustrated in FIGS. 8A-C-10 can include open regions shaped in various ways including linear sections, although circular, elliptical (e.g., from circular to a 1:2 ratio), or ovoid top region seem to reduce the impact of tissue-induced stress that can lead to delamination of the tissue culture of interest (e.g., skin tissues). A stretchable device may allow for flow in a bottom fluidic layer that is separated from a top fluidic layer by a permeable membrane (not shown), similar to the open-top microfluidic devices described for FIGS. 3-5A-F. While the open-top microfluidic device 800 is described as a stretchable device, it can be used with membranes other than stretchable membranes (e.g., PDMS membranes) for applications where membrane stretch is not desired.

Turning to FIG. 8A, a top view of the exemplary assembled stretchable open-top microfluidic device 800 is illustrated. The device 800 includes a top structure 820 that has three apertures therethrough which define a plurality of open-top open regions 804a, 804b, 804c that may include a gel or porous volume. The open-top open regions may extend through the entire thickness of the top structure 820. As mentioned, mechanical actuation can be effected in a variety of ways; in the illustrated example, mechanical stretch is attained using one or more operating channels that on the perimeter of the open region. The top structure 820 further includes a plurality of vacuum port pairs: i) 830a, 832a; ii) 830b, 832b; and iii) 830c, 832c, that are in communication with the one or more vacuum chambers 837a, 838a, 837b, 838b and 837c, 838c. The vacuum port pairs can be connected to a vacuum device that is used to generate pressure differences that cause, for example, a membrane (not shown) to stretch (e.g., radially). Each open-top open region (e.g., 804a) is illustrated as having two opposing vacuum ports (e.g., 830a, 832a), thereby forming a vacuum port pair. The illustrated configuration permits a mechanical stretch generated by the opposing vacuum chambers 837a-c and 838a-c to apply a biaxial force on the device's membrane active regions. Combined with the circular shape of the open regions, the device approximates isotropic stretch, which may be desirable in the recapitulation of the biological mechanical environment of some organs, including the skin. In alternative embodiments, the shape of the open regions and vacuum chambers can be modified to augment the directionality and non-isotropicity of the stretch. Moreover, devices that include a plurality of vacuum chambers corresponding to one or more of the open regions allow the application of different pressures (including vacuum levels) permitting the selection of stretch directionality during use. The top structure 820 further includes a plurality of bottom fluidic layer inlet ports 819a, 819b, 819c and outlet ports 822a, 822b, 822c that allow for the introduction and extraction of fluids (e.g., for perfusion) from the open-top microfluidic device 800. FIG. 8B illustrates a perspective view of the top structure of the exemplary stretchable open-top microfluidic device of FIG. 8A, and in particular shows how the open-top open regions, vacuum ports, vacuum chambers and bottom fluidic layer extend through the entire top structure 820. More or fewer (e.g., one, two, four, five or more) open-top open regions and related support features are contemplated.

Turning now to FIG. 8C, a perspective view of the bottom structure 825 of the exemplary stretchable open-top microfluidic device 800 is illustrated. Similar to the previously described embodiments of an open-top microfluidic device, a permeable membrane (not shown) is disposed along the interface between the top structure 820 and the bottom structure 825. The bottom structure includes feeding channels 839a-c comprising a plurality of feeding channel wells (e.g., first feeding channel well 835a, second feeding channel well 835b, third feeding channel well 835c) that align with open-top inlet and outlet ports (e.g., 514 and 516), respectively. A membrane (not shown) separates the open-top open region (e.g., 804a) from the feeding channels 839a-c and feeding channel wells (e.g., 835a-c). It is contemplated that a gel layer in the device 800 can be formed on top of the membrane in the open-top openings similar to what is described elsewhere herein (see, e.g., FIGS. 5C-5D).

FIGS. 9 and 10 illustrate exemplary perspective views of cross-sections 9-9 and 10-10 through the stretchable open-top microfluidic device. of FIG. 8A. With the top and bottom structure assembled, the bottom fluidic layer inlet (e.g., 819b) and outlet ports (e.g., 822b) each extend through the membrane (not shown) such that the ports are each hydraulically connected to feeding channels 839a, 839b, 839c (e.g., illustrated as long narrow channels) in the bottom structure 825 to allow for the circulation or introduction of fluids into the open-top microfluidic device. FIG. 8A-C. Similarly, in FIG. 9 the vacuum port pairs (e.g., 930a, 932a; 930b, 932b; 930c, 932c) in the top structure 920 each extend to vacuum chamber pairs: i) 937a, 938a; ii) 937b, 938b; and iii) 937c, 938c formed by the interfacing of the top structure 920 and bottom structure 925. The vacuum chambers are at least partially defined by a stretchable or deformable surface pairs such as 1045b and 1046b that introduces pressure changes to actuate the membranes (not shown) at the interface of each of the open-top openings (e.g., 1004b) and with the bottom wells (e.g., 1006b. FIG. 10.

Figure 16:
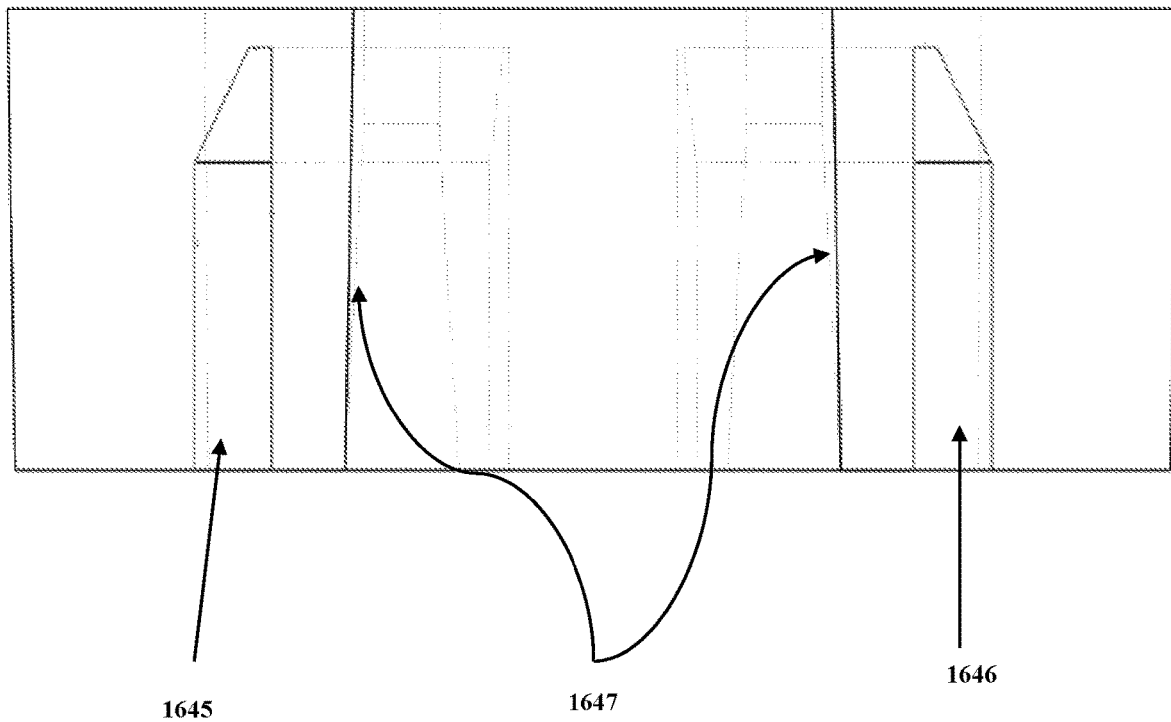
FIG. 16 shows one embodiment of vacuum channels designed to allow for uniform physiological stretching of a thick gel.

Although it is not necessary to understand the mechanism of an invention, it is believed that the presently disclosed vacuum chambers function to provide a pneumatic stretching of a membrane. For example, when placed under a vacuum, a first deformable surface 1645 and second deformable surface 1646 deflect towards each other as depicted by a deflection line 1647. FIG. 16. It is further believed that since the top portion of the deformable surfaces are deflected at a greater angle than the bottom portion of the deformable surfaces, the induced stress is transferred to the underlying membrane, thereby causing the membrane to stretch. A more detailed depiction of deformable surfaces 1945, 1946 induce a deflection 1947 that causes bending around the corner of the vacuum chamber wall, as shown by the change in position of the inner and outer dotted lines. FIG. 22.

Figure 11:
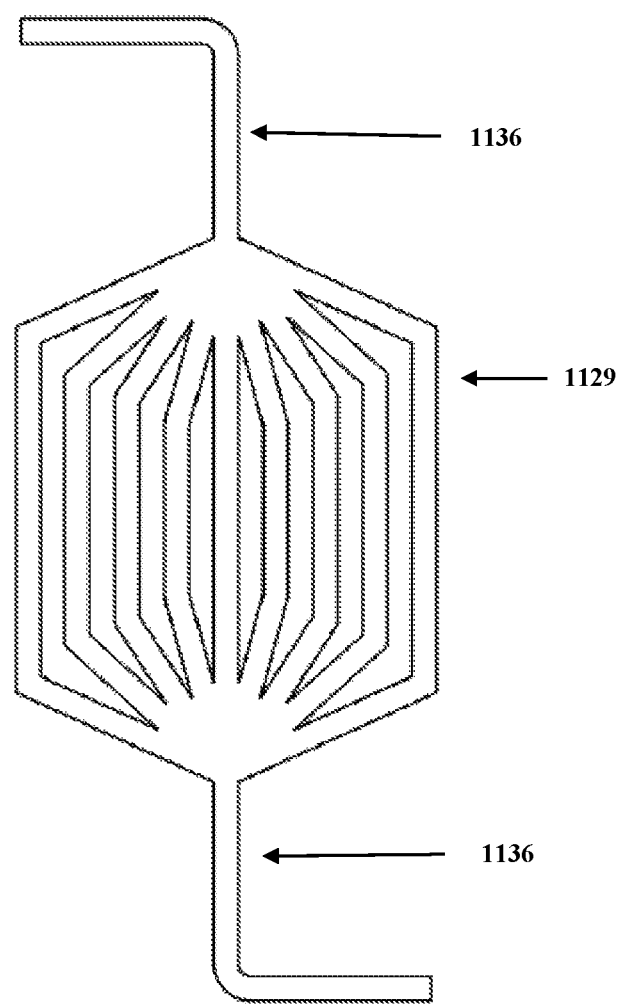
FIG. 11 illustrates a partial top view of an exemplary configuration of multiple parallel channels for a stretchable open-top micro-fluidic device.
Figure 12:
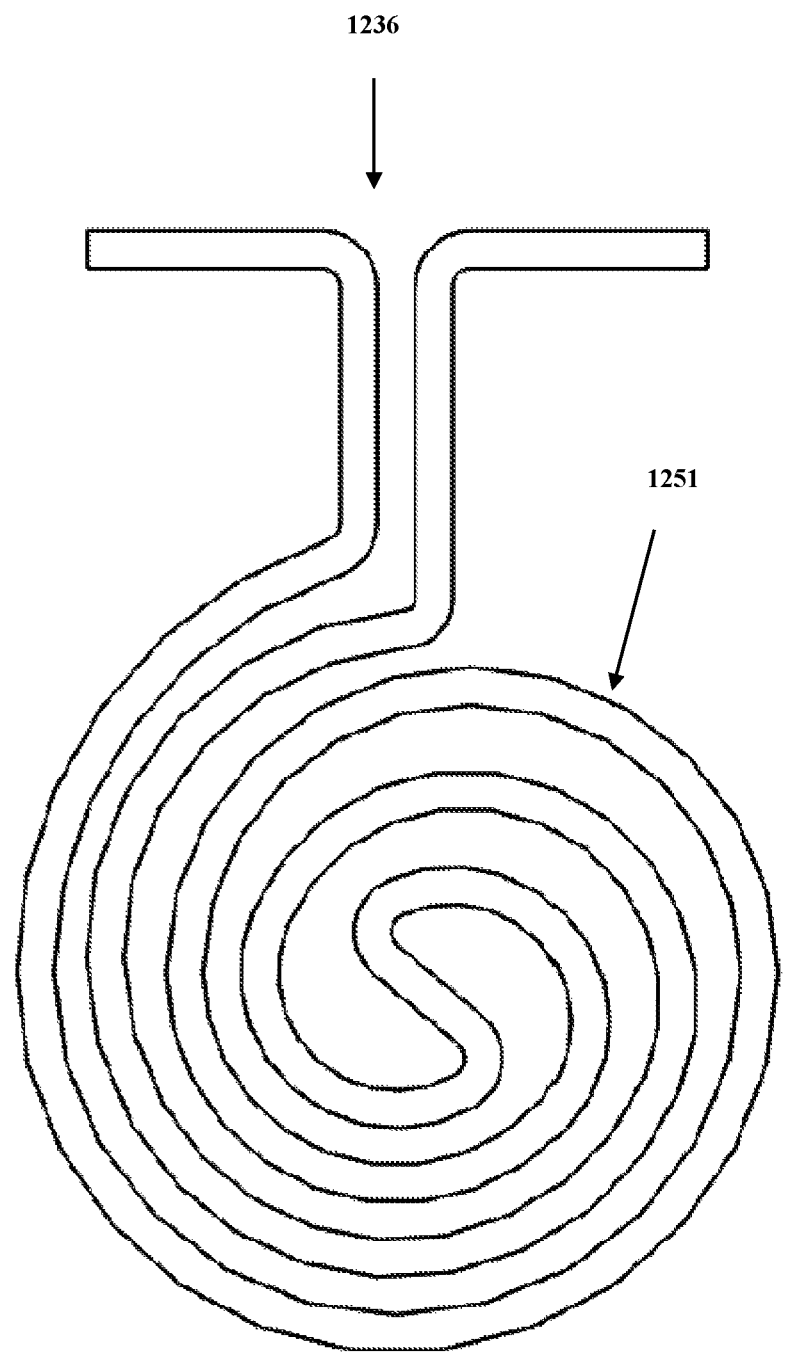
FIG. 12 illustrates a partial top view of an exemplary configuration of spiral channel for a stretchable open-top microfluidic device.

FIGS. 11 and 12 illustrate exemplary views of different bottom fluidic channel configurations. In the embodiment illustrated in FIG. 11, a lower microchannel 1136 is split into a number of constituent channels 1129. Although it is not necessary to understand the mechanism of an invention, it is believed that the smaller diameter of these constituent channels 1129, as compared to the diameter of a lower microchannel 1136, may offer an advantage in terms of bubble/debris clearance and flow uniformity compared to the single wider channel. Alternatively, as illustrated in FIG. 12, the lower microchannel 1236 can be take a spiral form 1251, or a serpentine or meandering form 2252 as illustrated in FIG. 22. Although it is not necessary to understand the mechanism of an invention, it is believed that the configuration of FIG. 12 can provide increased robustness in the face of bubbles and debris that may be present, and can provide a more even flow rate than the lower microchannel 1136 design illustrated in FIG. 11. However, the resulting channel length of the lower microchannel 1236 configuration in FIG. 12 is typically longer than in the lower microchannel 1136 designs similar to FIG. 11, with a shorter microchannel length being advantageous in some applications. For example, the spiral lower microchannel 1251 design illustrated in FIG. 12 first winds inwardly towards the center of the active region and the winds outwardly. An alternative design avoids the outward winding by flowing downward, either to a fluidic port or to an additional fluidic channel that may run underneath the spiral channel.

In one embodiment, the present invention contemplates an open-top microfluidic device 1300 comprising at least two open regions 1304. Each open region 11304 may be configured with an inlet port 1314, an outlet port 1316 and a vacuum port pair (1330, 1332).

Figure 14A:
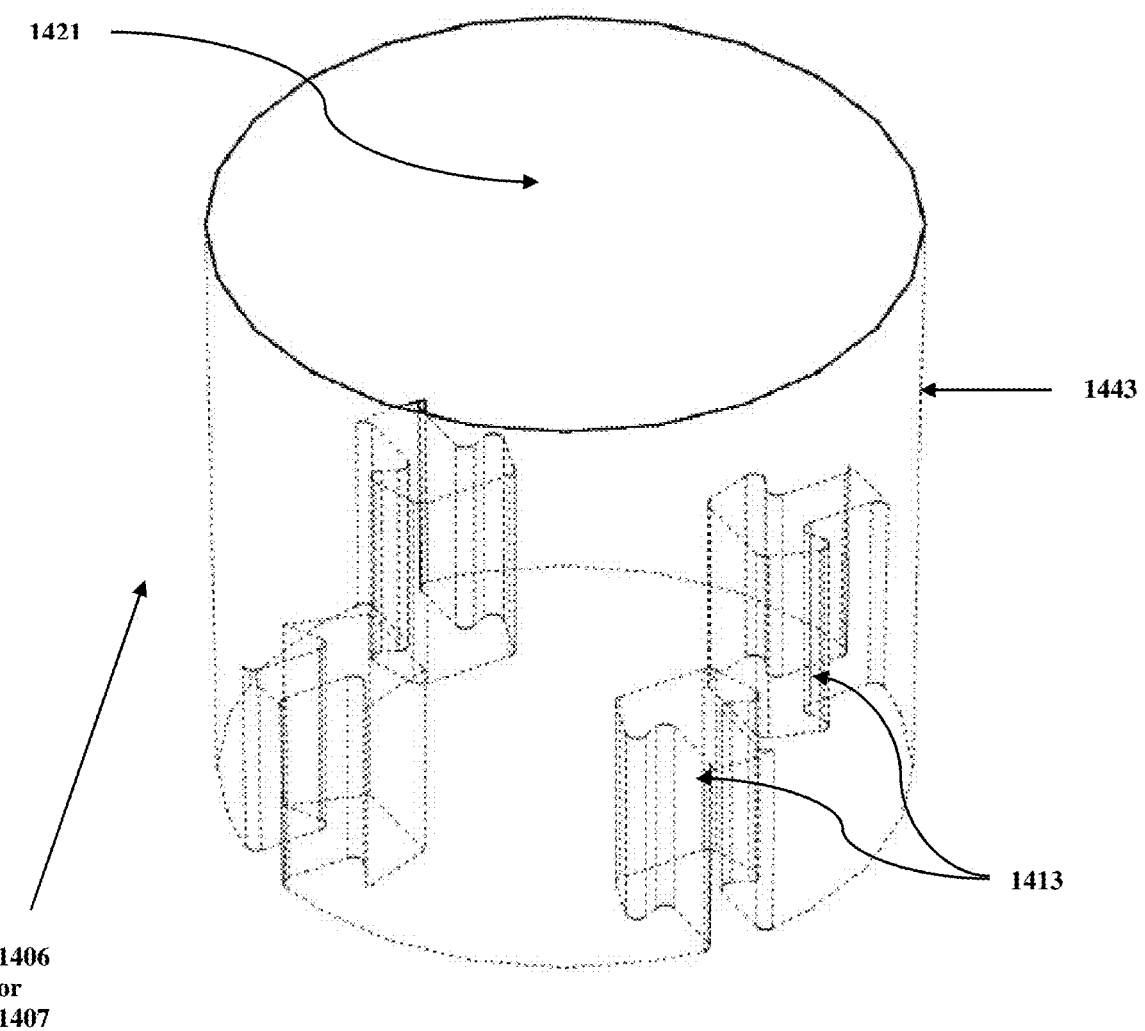
FIG. 14A-B shows one embodiment of structural anchors along the cavity/chamber walls in order to prevent shrinkage-induced delamination of a gel (not shown).
Figure 14B:
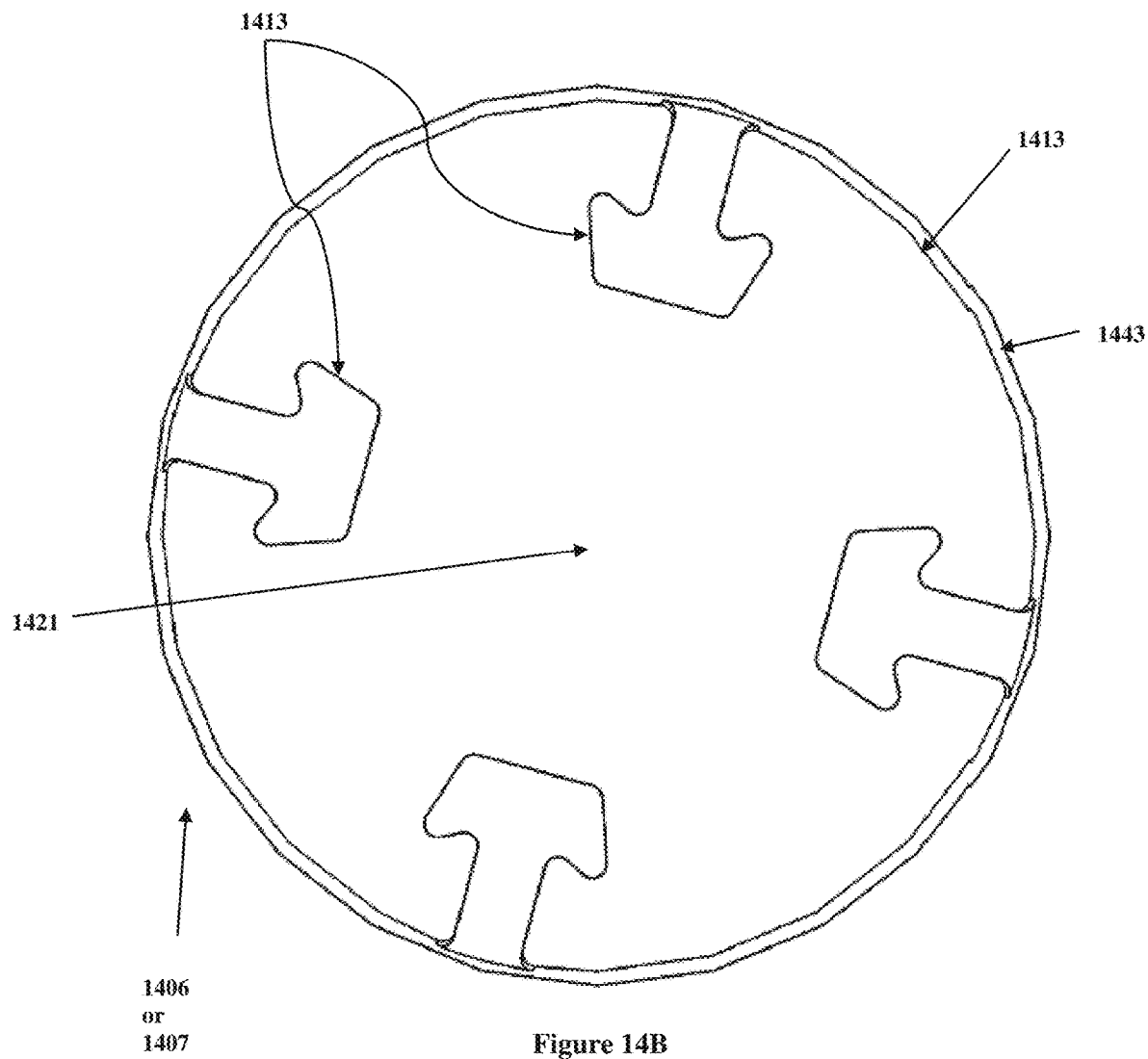

In one embodiment, the present invention contemplates an open top microfluidic device 1400 comprising a top chamber 1407 or a bottom chamber 1406, said chambers having side walls 1443 where a plurality of projections 1413 protrude into a chamber lumen 1421. FIG. 14A and FIG. 14B.

Figure 15:
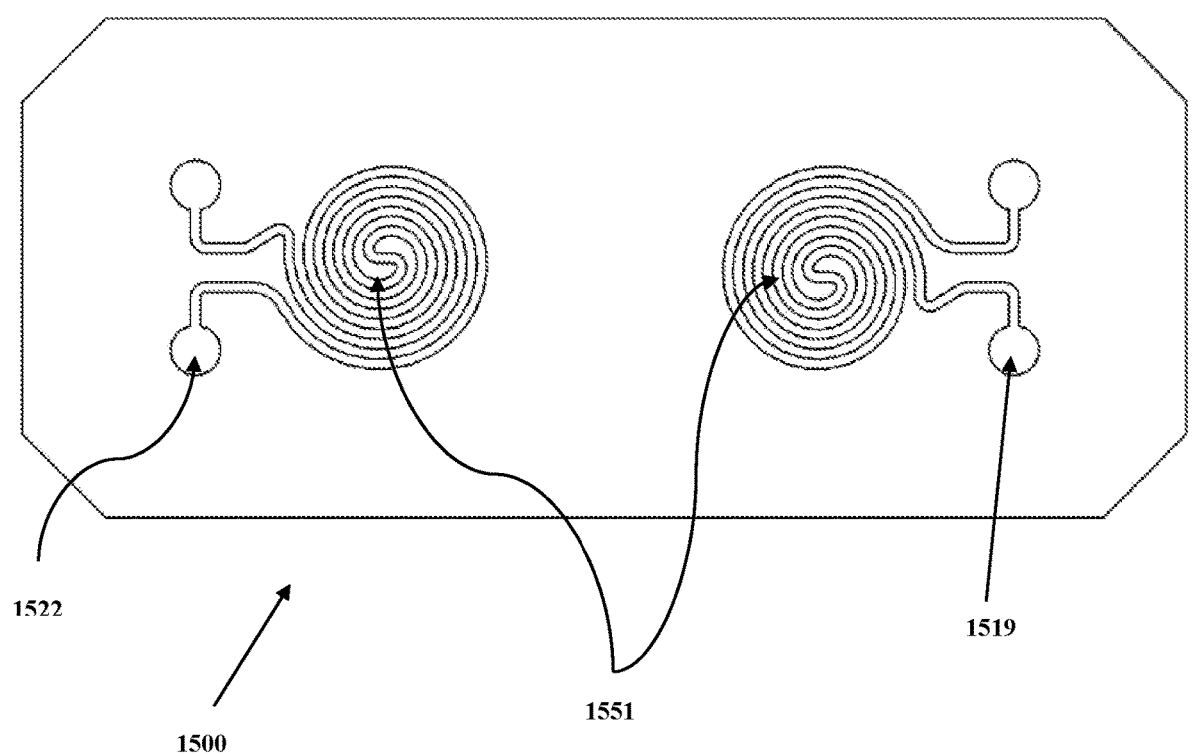
FIG. 15 shows one embodiment of bottom layer microfluidics, which allow for shear forces, concentration gradients, and vascularization (e.g. of endothelial cells).

In one embodiment, the present invention contemplates an open-top chip device 1500 comprising at least two spiral lower microchannels 1551, wherein each of the microchannels are in fluidic communication with an inlet port 1519 and an outlet port 1522. FIG. 15.

Figure 17:
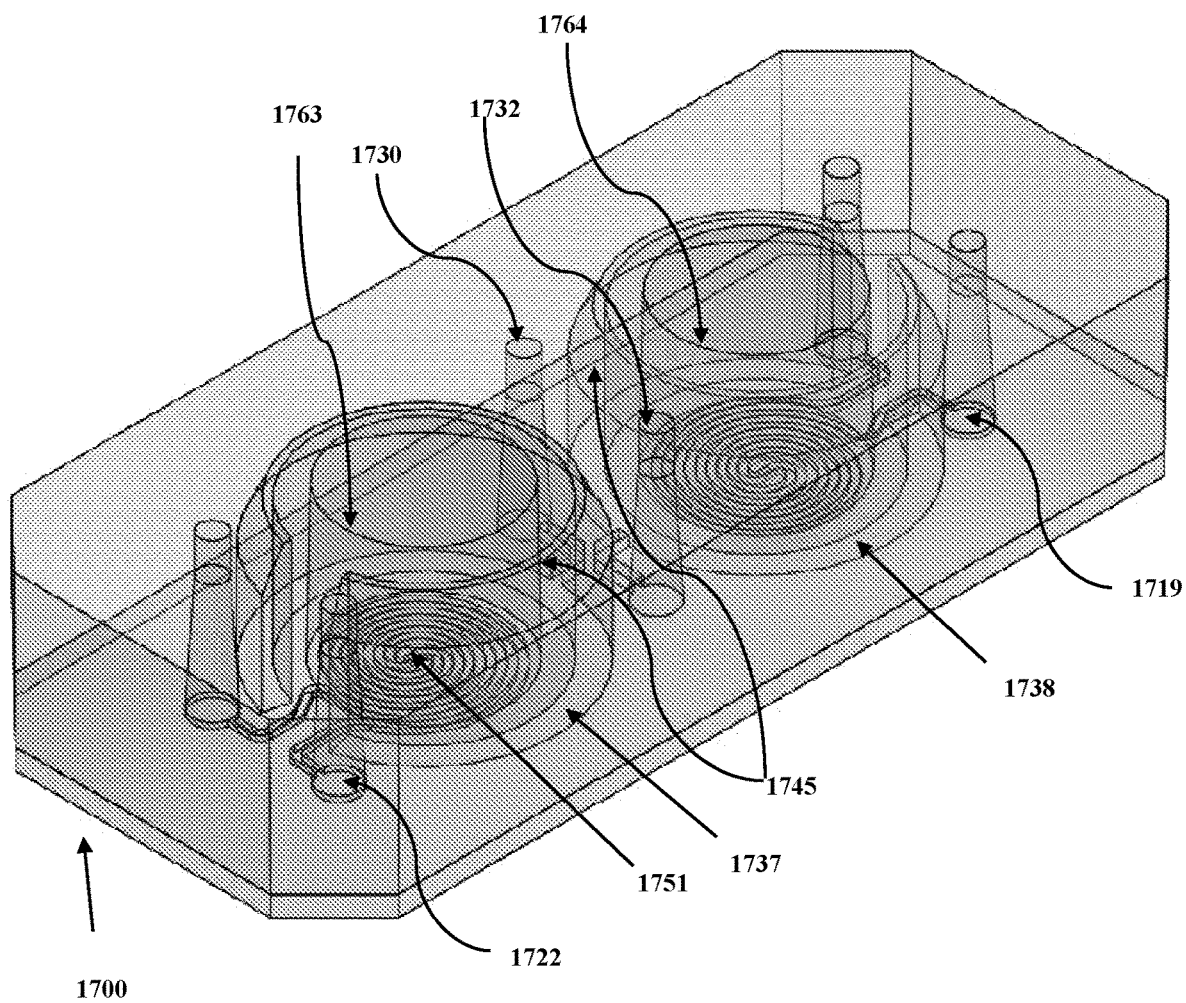
FIG. 17 shows one embodiment of an assembled chip, showing the open-top chambers above the fluidics.
Figure 18:
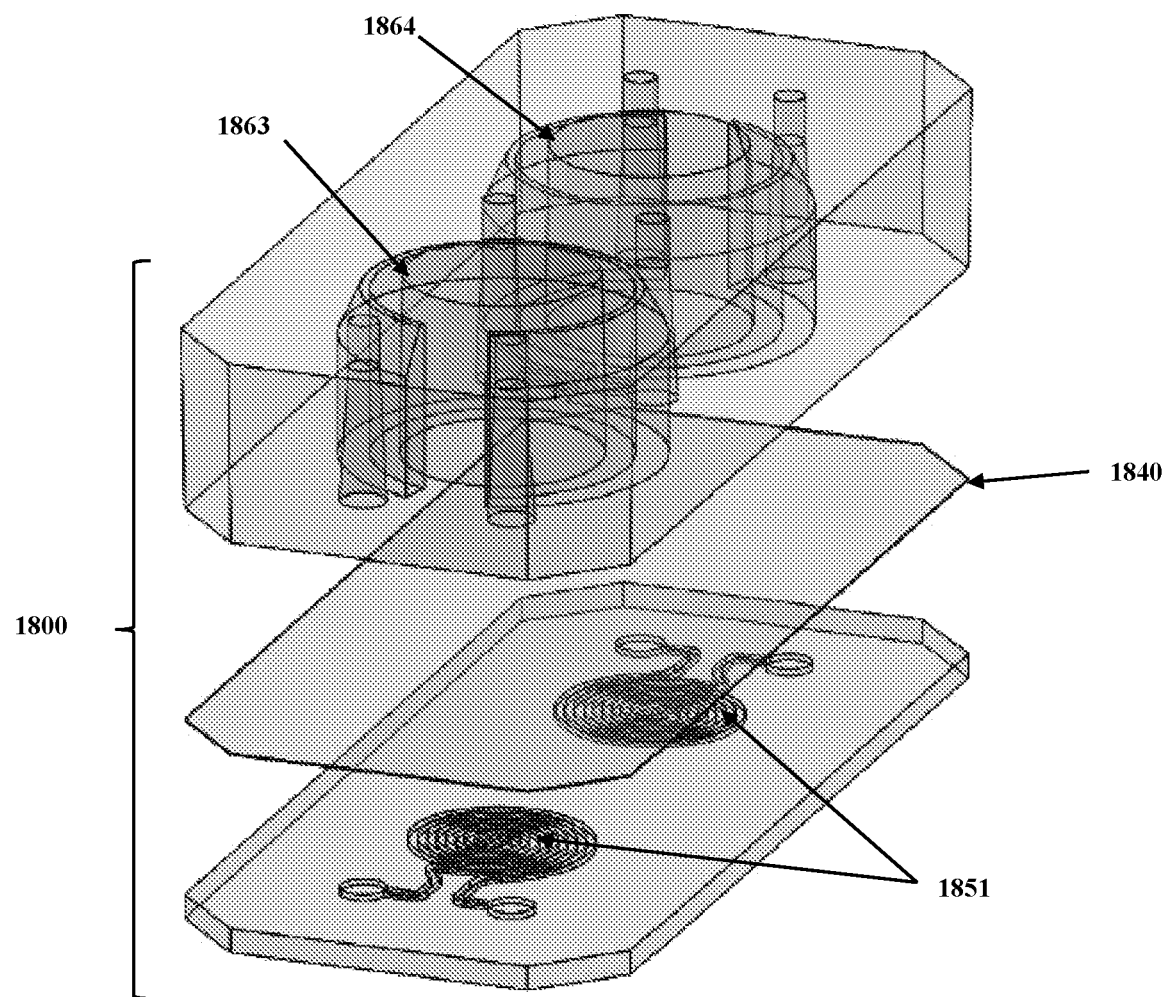
FIG. 18 shows the embodiment of FIG. 17, wherein the membrane is highlighted in order to illustrate the relationship of the assembled components.
Figure 19:
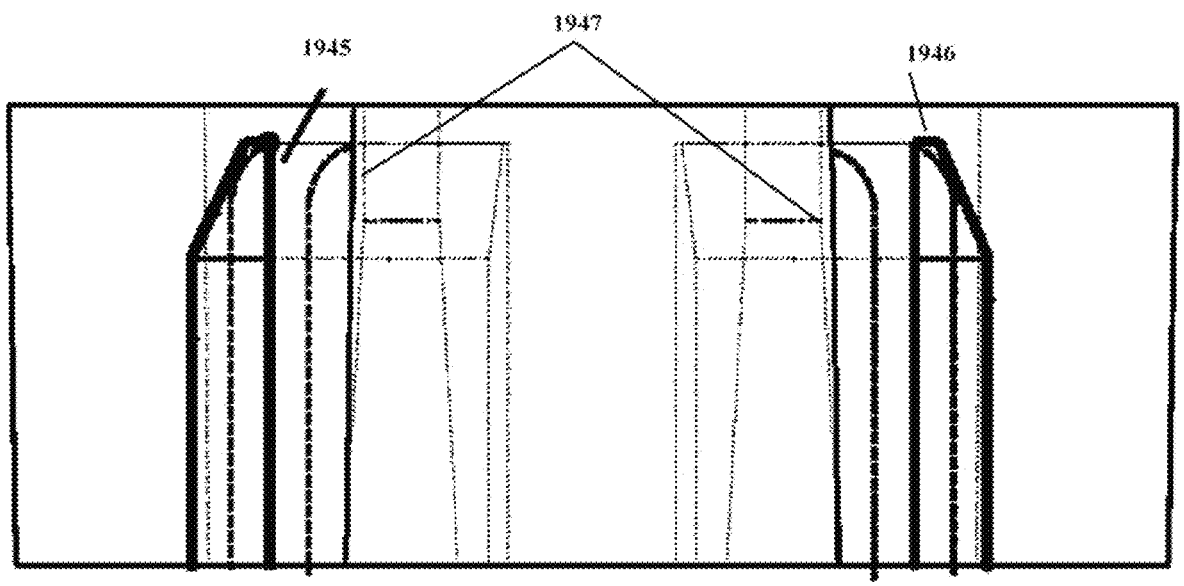
FIG. 19 shows a vacuum channel cross-section design that allows bending of the wall about the corner.

In one embodiment, the present invention contemplates an open-top chip device 1700 comprising: i) a first chamber 1763 and a second chamber 1764, wherein each chamber is surrounded by a deformable surface 1745; and ii) at least two spiral microchannels 1751 located on the bottom surface of the chambers, wherein each of the microchannels are in fluidic communication with an inlet port 1719 and an outlet port 1722 and are respectively configured with a first vacuum port 1730 or a second vacuum port 1732, such that each vacuum port is respectively connected to a first vacuum chamber 1737 or a second vacuum chamber 1738. FIG. 17. An exploded view of the embodiment depicted FIG. 17 shows an open-top chip device 1800, wherein a membrane 1840 resides between the bottom surface of the first chamber 1863 and the second chamber 1864 and the at least two spiral microchannels 1851. FIG. 18.

In some embodiments, the present invention contemplates an open-top chip device 2700 comprising at least two spiral lower microchannels 2751, wherein the microchannels are in fluidic communication with an inlet port 2719 and an outlet port 2722. FIG. 27. The spiral lower microchannel 2751 is also flanked by a vacuum port 2730 configured with a vacuum chamber 2737. A deformable surface 2745 is configured on the inside surface of the vacuum chamber 2737, In some embodiments, the present invention contemplates an array device 2811 comprising a plurality of open top chip devices 2800. Each of the open top chip devices 2800 is configured with at least an open region 2804 and flanked by an inlet port 2814 and an outlet port 2816, or alternatively, a first vacuum port 2730 and a second vacuum port 2732. FIG. 28. An exploded view of an array device 3911 is provided showing the open top chip devices 3900 in top structure 3920 and a bottom chamber 3906 in bottom structure 3925 with a membrane 3940 layered between the top structure 3920 and bottom structure 3925. FIG. 39.

Although it is not necessary to understand the mechanism of an invention, it is believed that an array device comprising open top chips represents a fundamental shift in architecture as compared to conventional "tissue-on-a-chip" designs. It is further believed that this array design facilitates multiplexing of 3D scaffold models for scaffold optimization. Furthermore, the array test platforms are designed to be compatible with existing 3D scaffold models in transwell. For example, array devices as contemplated herein are useful for 3D scaffold models, ECM/gel optimization and tissue chips including, but not limited to, skin, lung and intestine (e.g., gut). In one embodiment, an array device 2811 may have the following specifications:

| Body Material | PDMS Sylgard 184 |
|---|---|
| Membrane Material | PDMS Sylgard 184 |
| Dimensions | |
| Width | 51.8 mm |
| Length | 50.8 mm |
| Height | 8.0 mm |
| Open-Top Chamber Dimensions | |
| Top Chamber Diameter | 6.3 mm |
| Top Chamber Height | 6 mm |
| Top Channel Volume | 193.02 mm$^3$ |
| Top Culture Area | 32.17 mm$^2$ |
| Bottom Chamber Dimensions | |
| Bottom Chamber Diameter | 5.4 mm |
| Bottom Channel Height | 1 mm |
| Bottom Channel Volume | 22.90 mm$^3$ |
| Bottom Culture Area | 22.90 mm$^2$ |
| Membrane Dimensions | |
| Pore Diameter | 7 μm |
| Pore Spacing | 40 μm (hexagonally packed) |
| Thickness | 50 μm |
| Co-culture Area | 22.9 mm$^2$ |
| Minimum Imaging Distance (top of membrane) | 2 mm |

Additional exemplary embodiments of open-top microfluidic devices, such as the devices discussed above in FIGS. 1-12, are now described further. In some embodiments, the dimensions of the top area of the open region in a top structure for a chip can range from about 0.1 to about 17 millimeters (or 1 to about 7 millimeters) along in the narrowest dimension. In some embodiments, the dimensions range from about 0.5 to about 200 or more millimeters (or about 0.5 to about 20 millimeters). The lower end of the range of the narrowest dimension of the open region is also desirably sized to allow accessibility to the region for pipettes or syringes that are used to place, for example cell cultures or gel materials. The open region can be sized to limit any capillary action, which may be undesirable in some applications (capillary action may nevertheless be desirable in other applications). It is further desirable in some applications for the upper range of the open region dimensions to be sized to maintain accuracy in the flow distribution for the bottom channel across the cell culture area.

In some embodiments, the depth of the open region (e.g., measuring vertically upward in the open region from the interface of the top structure with the membrane) can vary from about 0.1 to about 20 millimeters (or about 1 to about 5 millimeters). In some embodiments, an additional well or spacer may be added to increase the well volume of the open region, such as where the full depth of the open region is completely filled. It is contemplated that aspect ratios of the dimensions for the top area to the depth of the open region in some applications should range from about 1 to above 100, or in some applications from about less than 0.01 to 2.

In some embodiments, it is desirable to have different geometries for the open region based on the type of tissue that is subject to experimentation. For example, certain types of tissue, such as skin, are highly contractile during culturing. When placed into high-aspect ratio (e.g., 16 millimeters by 1 millimeter) channels, delamination of the tissue can occur along the narrow dimension. However, an open region that has a circular (e.g., open region 804a) provides radial symmetry that can allow tissue to shrink uniformly and not move out of plane. A wider channel geometry that minimizes edge effects can also be beneficial for other organ systems that may require multiple layers, such as the blood-brain barrier, airways, or digestive tract, because the layers can be more easily formed by the sequential deposition of thin gel or cellular tissue layers, which is difficult to do in closed channels or chambers. In some embodiments, the geometry of the open region is something different than the rectangles or circles illustrated in the exemplary embodiments of FIGS. 5A-F and 8A-C. For example, a triangular or star geometry can be used to look at the effects of cell crowding or diffusion of signaling molecules as affected by geometry. In another example, a "FIG. 8A-C" shape can be beneficial for analyzing the interaction between two three-dimensional cultures For fluidic channel(s) disposed in the top structure of an open-top device that might be used for skin, bronchial, or gut tissue simulations, the geometry and dimensions for the open region of a chamber can include a channel-type geometry with a channel height ranging, for example, from about 0.02 millimeters to about 10 millimeters, a channel width of about 0.05 millimeter to 20 millimeter, and a channel length of about 0.5 millimeters to about 300 millimeters. In some embodiments, the geometry and dimensions for the open region of a top chamber can include a channel-type shape with a height ranging, for example, from about 0.02 millimeters to about 10 millimeter and a fluidic cover fluidic channel width of about 0.05 millimeter to 20 millimeter. The base or bottom chamber can also have a channel-type shape with a height ranging, for example, from about 0.02 millimeters to about 10 millimeter. For an optional top structure 420 that might be used for brain-barrier and lung tissue simulations, the geometry and dimensions for the top structure, for example, include a height of about 0.05 millimeters to about 5 millimeter. A taller top structure spacer in an open-top microfluidic device is often used for simulations where three-dimensionality is desirable, such as where fibroblast or other cells are embedded in the gel layer for the formation of, for example, a dermal layer. A shorter top structure spacer in an open-top microfluidic device can be used, for example, for simulations where two- or three-dimensionality is desired, such as for small airway simulations where small airway cells feel the paracrine stimulation of neighbor cells, which stimulates their full differentiation.

Various tissue types are contemplated for testing in an open-top microfluidic device (e.g., an open-top OOC device), such as skin, small-airway, and alveolar tissues. However, open-top microfluidic devices can also accommodate other types of tissues, as well, including other epithelial tissues.

The properties of gels or porous volumes that can be used for an open-top microfluidic device can vary and the properties will often depend on the different tissue type that is being tested. For example, different tissue types or specific models may employ different extracellular matrix proteins (ECMs) and ECM mixtures (for example, collagen I, collagen IV, Matrigel®, laminin, fibronectin, gelatin, elastin, etc., and combinations thereof). Additionally, some embodiments may employ synthetic polymer gels (e.g. polyacrylamide, polyvinyl alcohol, etc.) or various other gels known in the art (e.g. agarose, alginate, etc.) alone, in mixture, or in combinations with ECMs. Similarly, porous volumes used for an open-top microfluidic device may include a variety of open-cell foams, for example, expanded polyurethane, expanded polystyrene, expanded cellulose, expanded polylactic acid, etc. Without being bound by example, for the simulation of a skin or bronchial tissue, the gel can have a higher concentration of collagen, roughly at about 1 to about 11 milligrams per milliliter of gel. For the simulation of gut tissue function, one exemplary embodiment contemplates a gel with a 1:1 ratio of a high concentration collagen to an ECM such as the Corning® Matrigel® matrix available from Corning Life Sciences, is desirable. For the simulation of alveolar tissue function, one exemplary embodiment contemplates a gel with a 1:1 ratio of a low concentration of collagen (e.g., about 3 milligrams per milliliter of gel) to ECM, such as the Corning® Matrigel® matrix or fibronectin, is desirable. It is contemplated in one embodiment that extracellular matrices or other gel precursors that form gels with concentrations of above 5 milligrams per milliliter of gel, or ranging from about 3 to about 15 milligrams per milliliter of gel, or ranging from about 0.2 to 4 milligrams, can be used in the open-top microfluidic devices described herein. Moreover, cross-linking agents such as, but not limited to, transglutaminase, glutaraldehyde, bis(sulfosuccinimidyl)suberate, and many other cross-linkers known in the art, can be used to increase gel stiffness and optionally lower gel concentration. With the use of cross-linkers, it is contemplated that extracellular matrices or other gel precursors that form gels with concentrations ranging from about 0.05 to 5 milligrams per milliliter of gel, or ranging from about 1 to 10 milligrams per milliliter of gel, can be used in the open-top microfluidic devices described herein.

While the described open-top microfluidic devices, including open-top OOC devices, are compatible with standard microfluidic fluids having relatively low viscosities (e.g., about 1 to about 10 centipoise or less), the open-top devices are well-suited for high viscosity solutions and gels having a viscosity equal to or greater than 10 centipoise along with being well-suited for the polymerization of gels in situ for later removal from the microfluidic device and other manipulation of the gel. For example, collagen gels with a high protein content (e.g., 3 milligrams per milliliter) can be directly pipetted into the open tops and gelled in place without shearing cells or requiring high pressure actuation. For drug testing applications, creams and similar high-viscosity materials can be spread directly on the tissue using the open tops to test compounds in the final formulations rather than dissolved drugs alone. Thick gels layers can also be easily generated for three-dimensional culture applications with the potential for providing mechanical stretch. Other desirable embodiments of open-top microfluidic devices include the open tops are readily compatible with aerosol and other particulate (e.g., liquid or solid) delivery while minimizing loss, which allows for enabling high dosing accuracy. Because the particles can be delivered directly to the tissue, there is minimal loss due to adsorption to other surfaces, such as tubing and microchannels.

In some embodiments, the gel layer described in the above embodiments does not need to be patterned. It is also contemplated that a gel or other material suitable for growing tissues can be patterned externally, shaped to fit the open region of the channel or chamber of the top structure, and subsequently inserted into the open-top microfluidic device for cell culture. The gel or other material could also be a large sheet that is compressed using the spring loaded clamps with the two chambers or channels on either side of the gel or other material, where the gel or other material acts as a membrane in the open-top microfluidic device. The externally-prepared material can include biological tissue such as a biopsy from a patient or small piece of artificial tissue prior to implantation, and thus allow the performance of assays on tissue to determine drug response, tissue quality, and other factors. It is further contemplated that the gel or a similar material from the open-top microfluidic device can be extracted via the open top and used for in vivo applications. For example, the microfluidic device could be used to pattern and mature the tissue prior to implantation.

Numerous skin substitutes are commercially available, such as epidermal substitutes, dermal substitutes, and bilayer substitutes. These can be employed together with the devices, layered structures and methods described above.

Preferred Embodiments

A. Blood Brain Barrier

Brain microvascular endothelial cells (BMEC) are interconnected by specific junctional proteins forming a highly regulated barrier separating blood and the central nervous system (CNS), the so-called blood-brain-barrier (BBB). Together with other cell-types such as astrocytes or pericytes, they form the neurovascular unit (NVU), which specifically regulates the interchange of fluids, molecules and cells between the peripheral blood and the CNS.

The blood-brain barrier is of major clinical relevance because dysfunction of the blood-brain barrier leads to degeneration of the neurovascular unit, and also because drugs that are supposed to treat neurological disorders often fail to permeate the blood-brain barrier. Due to its importance in disease and medical treatment, it would be highly advantageous to have a predictive model of the human blood-brain barrier that recapitulates aspects of the cerebral endothelial microenvironment in a controlled way.

In one embodiment, the present invention contemplates a layered structure comprising i) fluidic channels covered by ii) a porous membrane, said membrane comprising iii) a layer of brain microvascular endothelial cells and said membrane positioned below iv) a gel matrix (or other porous volume). The present invention contemplates, in one embodiment, living neuronal cells (e.g. neurons, astrocytes, pericytes, etc.) on, in or under the gel matrix. It is preferred that some portion of the device can be opened for access to these cells. In one embodiment, the device comprises a removable top. The gel can be patterned to control the positioning and/or orientation of the cells or portions thereof. For example, the pattern on the gel matrix can direct neurite growth for neurons seeded on the patterned surface.

B. Transepithelial Electric Resistance

There are many ways to evaluate the integrity and physiology of an in vitro system that mimics the blood brain barrier. Two of the most common methods are Transepithelial Electric Resistance (TEER) and Lucifer Yellow (LY) rejection. Lucifer Yellow (LY) travels across cell monolayers only through passive paracellular diffusion (through spaces between cells) and has low permeability. Therefore it is considerably impeded in passing across cell monolayers with tight junctions. Permeability (Papp) for LY of <5 to 12 nm/s has been reported to be indicative of well-established monolayers. One of skill in the art would understand that manipulations should be performed using aseptic techniques in order for the cells to remain in culture without contamination. TEER measures the resistance to pass current across one or more cell layers on a membrane. Specifically, this electrical resistance is a direct measurement of the resistance of the cell monolayer to the transport of ions. The measurement may be affected by the pore size and density of the membrane, but it aims to ascertain cell and/or tissue properties. The TEER value is considered a good measure of the integrity of the cell monolayer.

Figure 23:
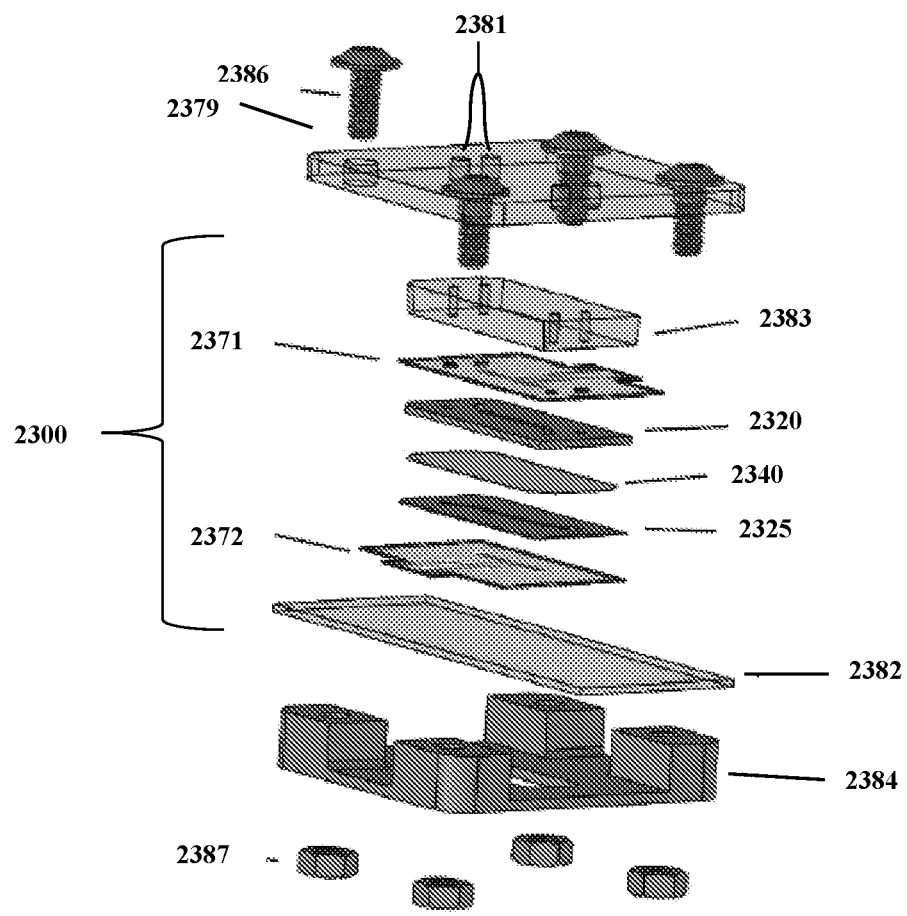
Figure 24:
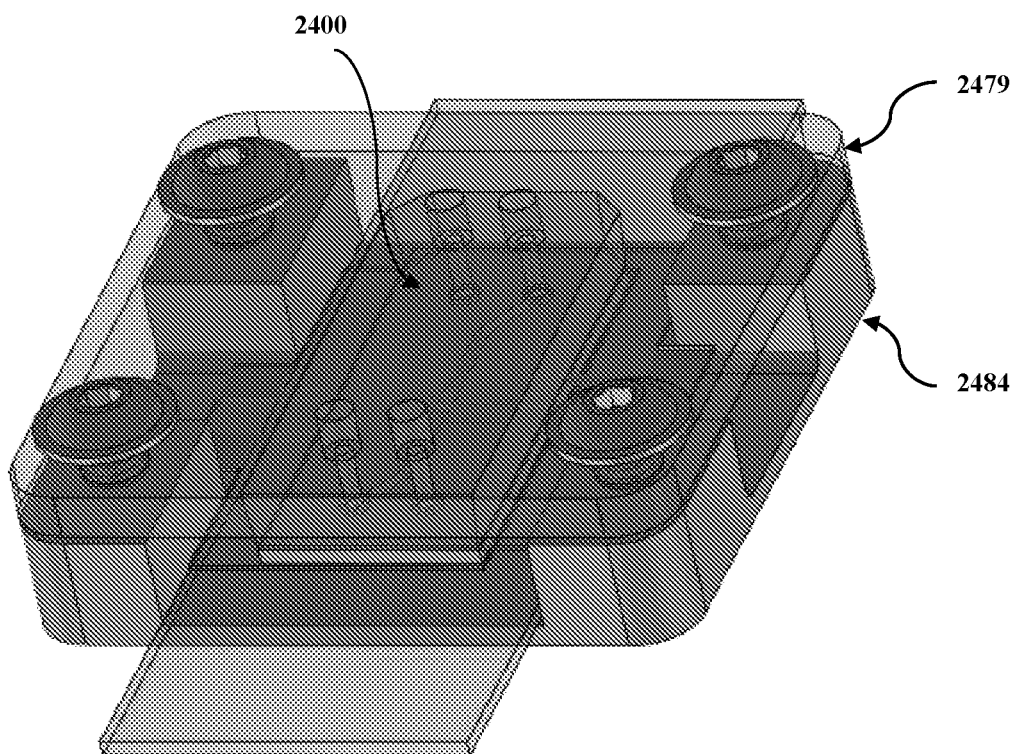

For TEER measurements, an embodiment is contemplated wherein a layered structure or microfluidic device 2300 has a top electrode 2371 and a bottom electrode 2372 configured for measuring the electrophysiology of said brain microvascular endothelial cells. FIG. 23 In one embodiment, the top electrode 2371 is a chromium/gold (Cr—Au) electrode. In one embodiment, the bottom electrode 2372 is a chromium/gold (Cr—Au) electrode.

However, it is not intended that the present invention be limited to only TEER measurements. In one embodiment, the present invention contemplates a method of testing, comprising 1) providing a layered TEER microfluidic device 2300 comprising i) a bottom structure 2325 comprising at least one upper microfluidic channel 2334 covered by ii) a porous membrane 2340, said membrane comprising iii) a layer of brain microvascular endothelial cells in contact with said at least one upper microfluidic channel, said membrane position below iv) a gel matrix (or other porous volume), said gel matrix (preferably) under a removable cover; and 2) measuring the electrophysiology of said brain microvascular endothelial cells. In one embodiment, the porous membrane 2340 is covered by a top structure 2320. In one embodiment, the layered TEER microfluidic device 2300 further comprises a top clamp 2379 and a bottom clamp 2384, wherein said top clamp 2379 has at least one access hole 2381. In one embodiment, the at least one access hole 2381 is configured to align with a port adapter 2383. In some embodiments, a glass slide 2382 is placed between the bottom electrode 2372 and the bottom clamp 2384. In one embodiment, the top clamp 2379 comprises a lasercut acrylic material. In one embodiment, the port adapter 2383 comprises a cast PDMS material. In one embodiment, the top electrode 2371 comprises a lasercut PET material. In one embodiment, the bottom electrode 2372 comprises a lasercut PET material. In one embodiment, the top structure 2320 comprises an open-top channel gasket having a cast PDMS material. In one embodiment, the bottom structure 2325 comprises an open-bottom channel gasket having a spincoated and lasercut PDMS material. In one embodiment, the bottom clamp 2384 comprises a 3D printed ABS plastic material. Although not limiting, the top clamp 2379 and bottom clamp 2384 may be attached with M4 screws 2386 and M4 nuts 2387. Although it is not necessary to understand the mechanism of an invention, it is believed that a TEER microfluidic device is clamped because the various layered components described above would be difficult to glue (e.g., bonding). It is further believed that a clamp facilitates an ability to open the device and have direct access to cells for patch-clamp measurements. Alternatively, if this openable feature is not desired, the device layers can be bonded together. A fully assembled layered TEER chip 2400 between a top clamp 479 and bottom clamp 2384 is presented in FIG. 24.

Figure 25:
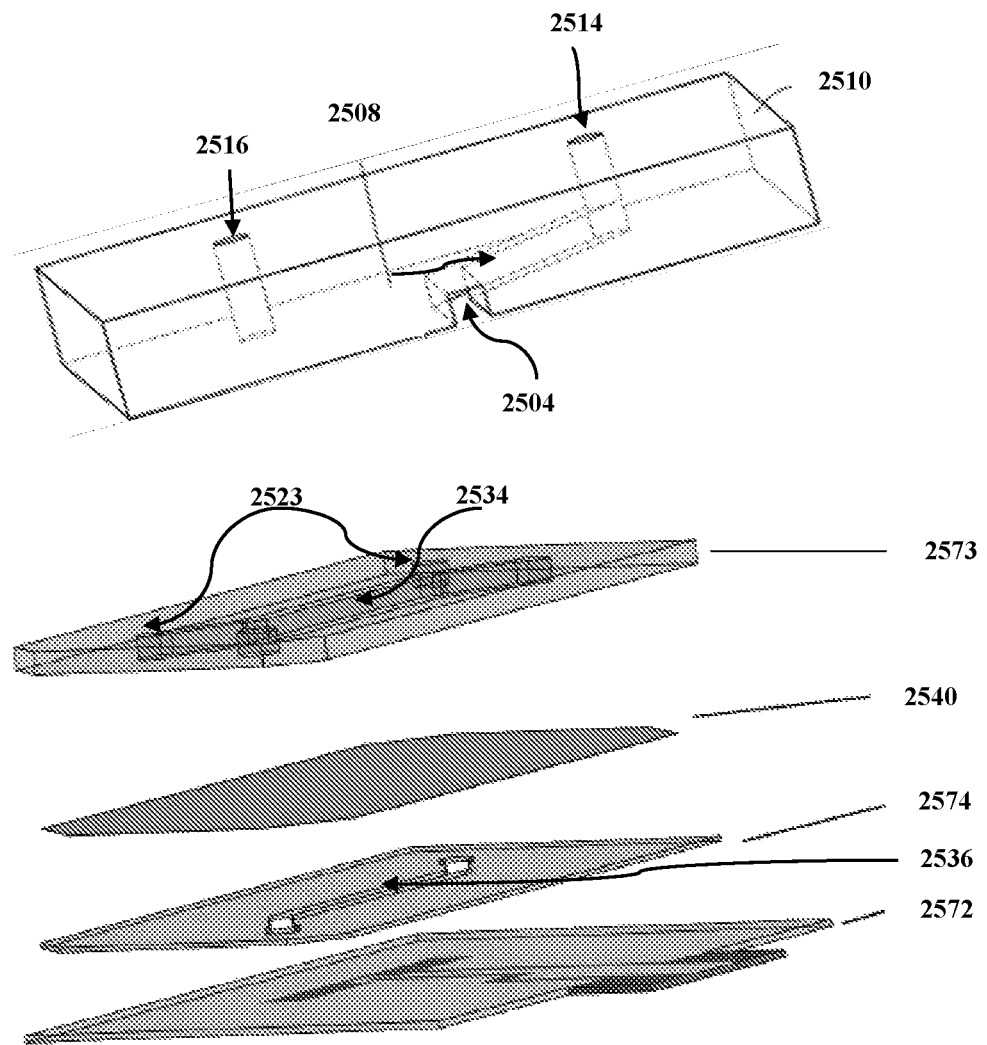

A variety of techniques are contemplated including but not limited to using a multi-electrode array or patch clamping. In one embodiment, the present invention contemplates an "open top" design that allows for patch clamping through the opening. For example, an open-top patch clamp layered TEER microfluidic device 2500 may comprise an optional top microfluidic cover 2510 comprising an open region 2504, an optional top microfluidic cover fluidic channel 2508 and inlet port 2514, wherein the open region 2504 provides access to an open-top channel gasket 2573. In one embodiment, the TEER microfluidic subassembly device 2500 comprises an open-top channel gasket 2573 having at least one upper microchannel 2534 in fluid communication with at least one upper microchannel well 2523. A porous membrane 2540 is placed between the open-top channel gasket 2573 and an open-bottom channel gasket 2574, wherein the open-bottom channel gasket 2574 comprises at least one lower microchannel 2536. A bottom electrode 2572 is placed underneath the open-top channel gasket/porous membrane/open-bottom channel gasket layered stack. In one embodiment, the bottom electrode 2572 is a chromium/gold electrode. FIG. 25

Figure 26:
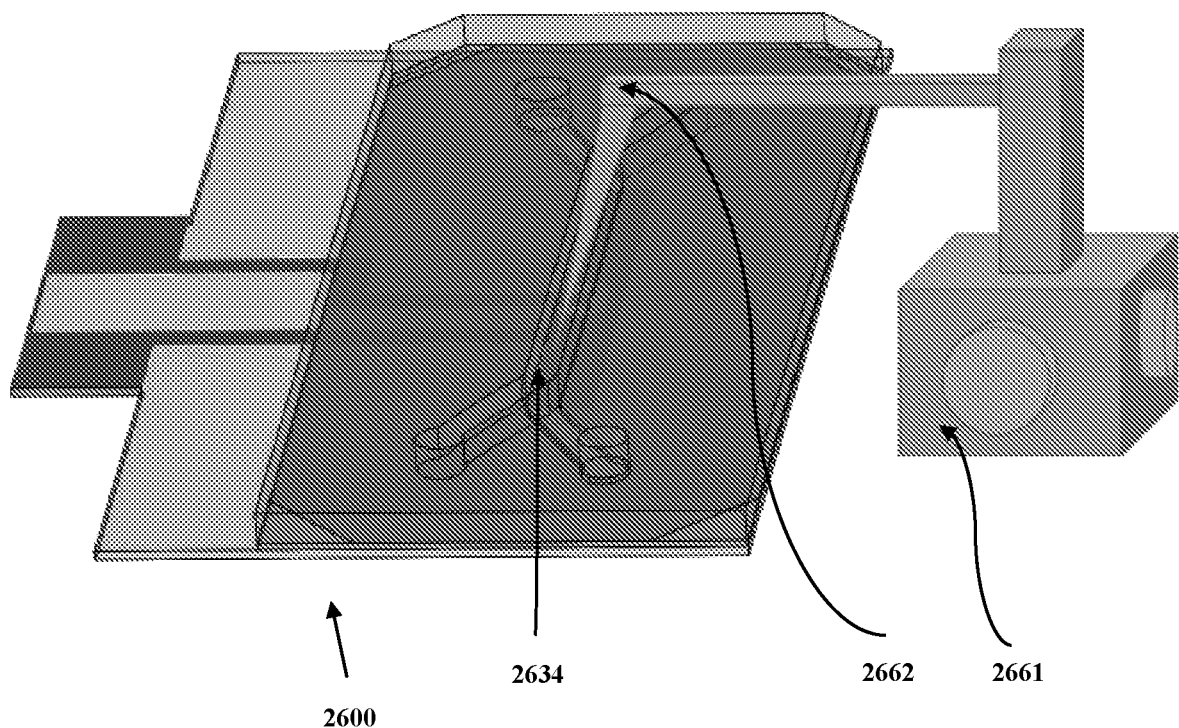

An open-top TEER microfluidic subassembly patch clamp device 2600 may be exposed to allow access with a micro-manipulator 2661. FIG. 26. For example, a micromanipulator arm 2661 my be placed directly within an upper microchannel 2634. Although it is not necessary to understand the mechanism of an invention, it is believed that the micromanipulator arm 2661 may, for example, add reagents, remove a fluid sample, add cells and/or remove cells. This allows the configuration of the patch clamp device 2600 to interchangeably go between a flow configuration (e.g., where the upper microchannel 2634 is not exposed) and an open configuration (e.g., where the upper microchannel 2634 is exposed).

C. Stretchable Open Top Chips

In one embodiment, the present invention contemplates a stretchable open top chip device 2900 comprising at least one spiral microchannel 2951 configured with at least one fluid inlet 2917 and at least one fluid outlet 2924. FIG. 29A. In one embodiment, the microfluidic chip device 2900 further comprises a upper microchannel with a circular chamber 2956 configured with a first fluid or gas port pair 2975 and second fluid or gas port pair 2976, a first vacuum port 2930 connected to a first vacuum chamber 2937 and a second vacuum port 2932 connected to a second vacuum chamber 2938, wherein the vacuum chambers are proximally configured around the spiral microchannel. In one embodiment, the upper microchannel with a circular chamber 2956 is positioned above the spiral microchannel 2951. FIG. 29B.

Although it is not necessary to understand the mechanism of an invention it is believed that the stretchable open top chip design represents a fundamental shift in architecture as compared to conventional "tissue-on-a-chip" designs. It is further believed that the open top design is compatible with 3D scaffold models. For example, an open top chip design may include, but is not limited to, three layers exemplified by a bottom channel, a middle chamber and a top channel. In one embodiment, the bottom channel layout may be spiral in shape in order to fit within the circular shape of the chamber. In another embodiment, the top channel allows for the ability to run media solutions or humidity-controlled gases (e.g., for example, air and/or oxygen-carbon dioxide mixtures such as 95% $O_2$/5% $CO_2$) to prevent gel evaporation. In another embodiment, the membrane is porous to facilitate cell-to-cell communication. Other embodiments provide a vacuum channel design that provides a mechanical stretch to the entire 3D scaffold thickness.

Furthermore, the open top stretchable chips as contemplated herein are useful for biological interfaces, co-cultures, multiple cell type cultures, tissue stretching, 3D scaffold models, micro-patterning and tissue chips including, but not limited to, skin, lung and intestine (e.g., gut). In one embodiment, an open top stretchable device may have the following specifications:

| Body Material | PDMS Sylgard 184 |
|---|---|
| Membrane Material | PDMS Sylgard 184 |
| Dimensions | |
| Width | 15.87 mm |
| Length | 35.87 mm |
| Height | 6.0 mm |
| Top Channel Dimensions | |
| Top Channel Height | 200 µm |
| Top Chamber Diameter | 5.70 mm |
| Top Chamber Dimensions | |
| Top Chamber Diameter | 5.70 mm |
| Top Chamber Height | 4.00 mm |
| Top Channel Volume | 102.07 mm³ |
| Top Culture Area | 25.52 mm² |
| Bottom Channel Dimensions | |
| Bottom Channel Width | 600 µm |
| Bottom Channel Height | 400 µm |
| Bottom Channel Volume | 5.446 mm³ |
| Bottom Culture Area | 13.6 mm² |
| Membrane Dimensions | |
| Pore Diameter | 7.0 µm |
| Pore Spacing | 40 µm (hexagonally packed) |
| Thickness | 50 µm |
| Minimum Imaging Distance (top of membrane) | 850 mm |

In one embodiment, the present invention contemplates a stretchable open top chip device 3000 comprising: i) a fluidic cover 3010 comprising an upper microchannel with a circular chamber 3056 configured with a first fluid or gas port pair 3075 and second fluid or gas port pair 3076; a fluid inlet port 3014, a fluid outlet port 3016, a first vacuum port 3030 and a second vacuum port 3032; ii) a top structure 3020 comprising a chamber 3063, a first vacuum chamber 3037 connected to the first vacuum port 3030, and a second vacuum chamber 3038, connected to the second vacuum port 3032, wherein the upper microchannel with a circular chamber 3056 overlays the top surface of the chamber 3063; and iii) a bottom structure 3025 comprising a spiral microchannel 3051 comprising an inlet well 3068 connected to the fluid inlet port 3014 and an outlet well 3069 connected to the fluid outlet port 3016, wherein a membrane 3040 is layered between the top structure 3020 and bottom structure 3025. FIG. 30.

In one embodiment, the present invention contemplates a stretchable open top chip device 3100 comprising a chamber 3163 comprising an epithelial region 3177 and a dermal region 3178. In one embodiment, the epithelial region comprises an epithelial cell layer. In one embodiment, the dermal region comprises a dermal cell layer, wherein said epithelial cell layer adheres to the surface of the dermal cell layer. In one embodiment, the device further comprises a spiral microchannel 3151 in fluid communication with a fluid inlet port 3114, wherein the microchannel comprises a plurality of vascular cells. In one embodiment, a membrane 3140 is placed between the chamber dermal cell layer and the microchannel plurality of vascular cells. In one embodiment, the device further comprises an upper microchannel with a circular chamber 3156 connected to a fluid or gas port pair 3175. In one embodiment, the device further comprises a first vacuum port 3130 connected to a first vacuum chamber 3137 and a second vacuum port 3132 connected to a second vacuum chamber 3138. In one embodiment, the membrane 3140 comprises a PDMS membrane comprising a plurality of pores 3141, wherein said pores 3141 are approximately 50 µm thick, approximately 7 µm in diameter, packed as 40 µm hexagons, wherein each pore has a surface area of approximately 0.32 cm². Although it is not necessary to understand the mechanism of an invention, it is believed that the pore surface area contacts a gel layer (if present). FIGS. 31A and 31B.

In one embodiment, the present invention contemplates a stretchable open top chip device 3200 comprising: i) a fluidic cover 3210 comprising an upper microchannel with a circular chamber 3256 configured with a first fluid or gas port pair 3275 and second fluid or gas port pair 3276; a fluid inlet port 3214, a fluid outlet port 3216, a first vacuum port 3230 and a second vacuum port 3232; ii) a top structure 3220 comprising a chamber 3263, a first vacuum chamber 3237 connected to the first vacuum port 3230, and a second vacuum chamber 3238, connected to the second vacuum port 3232, wherein the upper microchannel with a circular chamber 3256 seals with the top surface of the chamber 3263; and iii) a bottom structure 3225 layered underneath said top structure 3220. FIG. 32.

FIGS. 33A and 33B illustrate exploded views of two embodiments of a stretchable open top chip device comprising: i) a fluidic cover 3310 comprising an upper microchannel with a circular chamber 3356 configured with a first fluid or gas port pair 3375 and second fluid or gas port pair 3376; a fluid inlet port 3314, a fluid outlet port 3316, a first vacuum port 3330 and a second vacuum port 3332; ii) a top structure 3320 comprising a chamber 3363, a first vacuum chamber 3337 connected to the first vacuum port 3330, and a second vacuum chamber 3338, connected to the second vacuum port 3332, wherein the upper microchannel with a circular chamber 3356 overlays the top surface of the chamber 3363 and a first membrane 3340 layered between the fluidic cover 3310 and the top structure 3320; and iii) a bottom structure 3325 layered underneath said top structure 3220, wherein a second membrane 3340 is layered between the bottom structure 3325 and the top structure 3320. FIG. 33A-B.

FIG. 34A illustrates an assembled top view of a stretchable open top chip device as shown in FIG. 33A. FIG. 34B illustrates a cutaway assembled side view of a stretchable open top chip device as shown in FIG. 33A.

In one embodiment, the present invention contemplates a tall channel stretchable open top chip device 3500 comprising: i) a fluidic cover 3510 comprising an open region 3504; ii) a top structure 3520 comprising an upper microchannel 3534 attached to the fluidic cover 3510; iii) a bottom structure 3525 comprising a lower microchannel 3536 attached to the top structure 3520; and iv) a membrane 3540 layer between the bottom structure 3525 and the top structure 3520. In one embodiment, the open region 3504, upper microchannel 3534 and lower microchannel 3536 are configured to at least partially overlay each other. FIG. 35A and FIG. 35B. Although not intended to be limiting, the tall channel stretchable open top chip device 3500 may also comprise a vacuum port pair and/or inlet/outlet ports as shown and described above.

Although it is not necessary to understand the mechanism of an invention it is believed that a tall channel stretchable open top chip design represents a fundamental shift in architecture as compared to conventional "tissue-on-a-chip" designs. It is further believed that this tall channel open top design incorporates an openable lid for direct access to the top channel that allows for the ability to load thick gel matrices as well as micro-patterning of the gel.

Furthermore, the open top stretchable test platforms as contemplated herein are useful for biological interfaces, co-cultures, multiple cell type cultures, tissue stretching, 3D scaffold models, micro-patterning and tissue chips including, but not limited to, skin, lung and intestine (e.g., gut). In one embodiment, a tall channel open top stretchable device may have the following specifications:

| Body Material | PDMS Sylgard 184 |
| Membrane Material | PDMS Sylgard 184 |
| Dimensions | |
| Width | 15.87 mm |
| Length | 35.87 mm |
| Height | 5.85 mm |
| Top Channel Dimensions | |
| Top Channel Width | 1000 µm |
| Top Channel Height (closed) | 1000 µm |
| Top Channel Height (open) | 2000 µm |
| Top Channel Volume | 28.041 mm$^3$ |
| Top Culture Area | 28.0 mm$^2$ |
| Bottom Channel Dimensions | |
| Bottom Channel Width | 1000 µm |
| Bottom Channel Height | 200 µm |
| Bottom Channel Volume | 5.584 mm$^3$ |
| Bottom Culture Area | 24.5 mm$^2$ |
| Membrane Dimensions | |
| Pore Diameter | 7.0 µm |
| Pore Spacing | 40 µm (hexagonally packed) |
| Thickness | 50 µm |
| Co-culture Area | 17.1 mm$^2$ |
| Minimum Imaging Distance (top of membrane) | 850 mm |

In one embodiment, the present invention contemplates a fully assembled stretchable open top microfluidic device 3600 comprising a fluidic cover 3610 comprising microfluidic channel 3608, a first vacuum port 3630 and a second vacuum port 3632, wherein the microfluidic channel 3608 terminates at either end an inlet port 3614 and an outlet port 3616, respectively. FIG. 36.

A first cross-sectional view across plane A of FIG. 36 presents an open top microfluidic device 3700 in an assembled configuration comprising a fluidic cover 3710 attached to a membrane 3740, wherein the membrane 3740 overlays an open region 3704 (shown as hidden open region 3604 in FIG. 36) within a top structure 3720 that is attached to a bottom structure 3725. FIG. 37A. A second cross-section view across plane A of FIG. 36 presents an open top microfluidic device 3700 in a separated configuration where a fluidic top 3710 comprising a membrane 3740 is removed from top structure 3720 thereby providing access to an open region 3704, wherein a microfluidic channel 3608 is configured within the fluidic cover 3710. FIG. 37B.

A third cross-sectional view across plane A of FIG. 36 presents an open top microfluidic device 3800 in an assembled configuration comprising a fluidic cover 3810 attached to a membrane 3840, wherein the membrane 3840 overlays an open region 3804 (shown as hidden open region 3604 in FIG. 36) within a top structure 3820 that is attached to a bottom structure 3825. FIG. 38A. A fourth cross-section view across plane A of FIG. 36 presents an open top microfluidic device 3800 in a separated configuration where a fluidic top 3810 comprising a membrane 3840 is removed from top structure 3820 thereby providing access to an open region 3804, wherein a microfluidic channel 3608 is configured to traverse between fluidic cover 3810 and top structure 3820. FIG. 38B.

EXPERIMENTAL

Example 1—Keratinocyte and Fibroblast Cell Culture

This example describes the preparation of keratinocytes, and in particular human foreskin keratinocytes (HFKs). An aliquot of Lonza Gold KGM media (Lonza 192060) is placed in a 50 ml tube (i.e. with 1 cryovial of HFK cells, one needs 12 ml for the flask, 10 ml for the washing step and 1 to 5 ml to break the pellet for a total of about 25 ml). The medium is warmed by putting it into the water bath for 5-10 min and then transferred inside the sterile hood. The needed number of 15 and 50 ml conical tubes are prepared, along with the needed number of flasks. These are filled with the appropriate amount of Lonza medium.

To thaw the HFKs, a cryovial is removed from the liquid nitrogen container and transferred into the basket containing dry ice. The cryovial is placed into the water bath until the freezing medium inside it is completely melted. The cryovial is sprayed with ethanol and brought to the sterile hood. The cryovial is opened in the hood and the contents are collected from the cryovial (freezing medium+cells) using a 1000 µl pipette. The contents are transferred into the 15 ml conical tube containing Lonza Gold KGM medium previously warmed. This conical tube is closed and then tilted to mix. Thereafter, it is centrifuged at 1000 rpm for 5 minutes. The conical tube is sprayed with ethanol and returned to the sterile hood. It is opened and the supernatant is withdrawn, leaving the cell pellet. The pellet is re-suspended using fresh pre-warmed Lonza Gold KGM and the mixture is transferred to a flask (or flasks), which were previously filled with Lonza Gold KGM medium. The flasks are gently agitated to make sure that the medium covers the entire bottom surface. The flasks are then transferred to the incubator. The keratinocytes are fed with new media approximately every other day (about every 36 hours).

To thaw the fibroblasts, a cryovial is removed from the liquid nitrogen tank and transferred into the basket containing dry ice. The cryovial is placed into the water bath until the freezing medium inside it is completely melted. The cryovial is sprayed with ethanol and brought to the sterile hood. The cryovial is opened in the hood and the contents are collected from the cryovial (freezing medium+cells) using a 1004.1 pipette. Tee contents are transferred into the 15 ml conical tube containing Lonza FGM-2 medium previously warmed. This conical tube is closed and then tilted to mix. Thereafter, it is centrifuged at 1200 rpm for 5 minutes. The conical tube is sprayed with ethanol and returned to the sterile hood. It is opened and the supernatant is withdrawn, leaving the cell pellet. The pellet is re-suspended using fresh pre-warmed Lonza FGM-2 and the mixture is transferred to a flask (or flasks) which were previously filled with Lonza FGM-2 medium. The flasks are gently agitated to make sure that the medium covers the entire bottom surface. The flasks are then transferred to the incubator. The fibroblasts are fed with new media approximately every other day (about every 36 hours).

For detaching the HFKs by trypsinization, the protocol is as follows. First, an aliquot Lonza Gold KGM (Lonza 192060), Lonza reagent subculture reagent CC-5034 and E-medium (or variants) 10% FBS medium is placed in 15 ml and 50 ml tubes. It is convenient to us 4 mls of Lonza reagent subculture reagent CC-5034 per T75 flask and to add 8 mls of 10% FBS medium to the flask (which corresponds to 2 ml for each ml of reagent Lonza reagent subculture reagent CC-5034). The media and enzymes are warmed by putting it into the water bath for 5-10 min. The flask containing HFK (typically when the cells are between 50 and 70% confluence) is removed from the incubator, sterilized on the outside with ethanol, and transferred into the hood. The flask is opened and the Lonza Gold KGM medium is aspirated, being careful to not scratch the bottom flask surface where the cells are attached. Fresh pre-warmed Lonza Gold KGM medium (e.g. 5 mls) is then added to wash the cells. This media is also aspirated carefully. Then, 4 ml of 0.05% trypsin/EDTA (Corning 25-052 CL) is added to the flask and the flask is returned to the incubator. The detaching cells can be monitored using the microscope if desired. As a rule of thumb, keratinocytes should detach in about 2-3 minutes. Longer exposure to Lonza subculture reagent CC-5034 (or 0.05 EDTA trypsin Invitrogen 25200-056) could damage keratinocytes irreversibly. When the cells detach completely, the outside of the flask is sterilized and brought to the hood. The flask is opened and 8 ml of 10% FBS E-medium (or variants) is added to the flask (2 ml for each ml of 0.05 EDTA trypsin Corning 25-052-CL). Thereafter, the contents of the flask are conveniently transferred to a 15 ml conical tube. The tube is closed and centrifuged at 1000 rpm for 5 min. The tube is then sterilized with ethanol, returned to the hood and opened. The supernatant is gently aspirated, being careful not to disturb the cell pellet. After the supernatant is removed, the pellet is re-suspended using fresh pre-warmed Lonza Gold KGM medium. The mixture is then transferred to the flask/flasks, which were previously filled with Lonza Gold KGM medium. The flasks are gently agitated to make sure that the medium covers the entire bottom surface, and they are returned to the incubator. Feeding is as stated above.

For detaching the fibroblasts by trypsinization, the protocol is as follows. An aliquot of Lonza FGM-2 medium (Lonza CC-3132), Lonza reagent subculture reagent CC-5034 and 10% FBS medium is added in 15 ml and 50 ml tubes. It is convenient to use 4 ml Lonza reagent subculture reagent CC-5034 per T75 flask and 8 ml of 10% FBS medium to the flask (which corresponds 2 ml for each ml of reagent Lonza reagent subculture reagent CC-5034). The media and enzymes are warmed by putting them into the water bath for 5-10 min. The flask containing fibroblasts (typically when the cells are between 50 and 70% confluence) is removed from the incubator, sterilized on the outside with ethanol, and transferred into the hood. The flask is opened and the media is aspirated gently, being careful to not scratch the bottom flask surface containing the cell layer. 5 ml of fresh PBS is added to wash the cells (this can be done twice). The PBS is aspirated carefully, and 4 ml of 0.05% trypsin/EDTA (Lonza CC-5012) is added and the flask is returned to the incubator. The detaching cells can be monitored using the microscope if desired. As a rule of thumb, fibroblasts should detach in about 2-3 minutes. Longer exposure could damage the cells irreversibly. When the cells detach completely, the outside of the flask is sterilized and brought to the hood. The flask is opened and 8 ml of Trypsin Neutralizing Solution (CC-5002) [2 ml for each ml of 0.05% trypsin/EDTA (Lonza CC-5002)] is added. The flask contents are transferred to a 15 ml conical tube and this tube is centrifuged at 1000 rpm for 5 min. The tube is sterilized with ethanol and returned to the hood. The supernatant is aspirated, being careful not to disturb the cell pellet. Then, the pellet is re-suspended using fresh pre-warmed Lonza FGM-2 medium and the contents are transferred to the flask/flasks, which were previously filled with Lonza FGM-2 medium. The flasks are gently agitated to make sure that the medium covers the entire bottom surface and then returned to the incubator. Feeding is as indicated above.

Example 2—Embedding Cells in the Dermal Layer

For embedding fibroblasts into the dermal layer (e.g. gel matrix), the protocol is as follows. First, the fibroblasts are detached using the trypsinization protocol described above. However, the pellet is re-suspended in complete E-medium low calcium (0.6 mM $Ca^{++}$), supplemented with 0.5% (V/V) FBS (Invitrogen 16140071) and 2% penicillin/streptomycin (invitrogen 15140-122) and then added back to the flasks, where they are allowed to reach 50-60% confluence. Once again, the fibroblasts are detached according to the protocol described above. Once re-suspended, they are embedded into the dermal layer. From Day 0 to Day 1-2, the cells in the dermal layer are fed using complete E-medium low calcium (0.6 mM $Ca^{++}$), supplemented with 0.5% (V/V) FBS (Invitrogen 16140071) and 100 μm ascorbic acid, RM/TI transglutaminase 50 μg/ml. From Day 1-2 to Day 3-4, the cells in the dermal layer are fed using complete E-medium low calcium (1.2 mM $Ca^{++}$), supplemented with 0.5% (V/V) FBS (Invitrogen 16140071) and 100 μm ascorbic acid and RM/TI transglutaminase 50 μg/ml. From Day 14-18 on, the cells in the dermal layer are fed using complete cornification medium (1.8 mM $Ca^{++}$), supplemented with 5% (V/V) FBS (Invitrogen 16140071) and 100 μm ascorbic acid and RM/TI transglutaminase 50 μg/ml.

Example 3—Preparing the Dermal Layer

First, pipette tips are cooled by putting into refrigerator for 15-30 min (Pipettes need to be cold when working with rat-tail type I collagen in order to avoid coagulation). Both the pipette tips and the ECM matrix should stay in the ice box during the procedure.

In order to calculate the final volume of rat-tail type I collagen mixture needed, one calculates the number of dermal equivalent cultures that are needed. This calculation is based on 12 well+3 extra (those are needed to compensate for the ECM matrix that adheres to the surface of pipette). Where $2 \times 10^4$ neonatal or adult Human Foreskin Fibroblast per raft are employed and 12+3 rafts are prepared, one needs $15 \times 2 \times 10^4 = 30 \times 10^4$ fibroblasts (or 300,000 fibroblasts). To impede fibroblasts proliferation, one can irradiate the fibroblast with 70 Gy.

Now, to make 150 μl/raft×(12+3) rafts=2.25 ml. 10% 10×DMEM or variants *=0.225 ml or 225 μl. 10% reconstruction buffer +=0.225 ml or 225 μl 80% ECM matrix=1.8 ml or 1800 μl. (1.8 ml ECM matrix×2.4×10 1N NaOH (1M))=43.2 μl 1M NaOH (1M) (NaOH makes ECM matrix to coagulate). This is put into INCUBATOR 37° C. for 2-4 Hours.

One can trypsinize the fibroblasts using 0.05% trypsin/ EDTA (Corning 25-052 CL) according to protocol described above. One can then re-suspend the fibroblast pellet in the predetermined amount of 10×DMEM or variants. This is mixed with the necessary amount of reconstitution buffer. (Note: best results are obtained when fibroblasts are collected in active growth phase, which occurs when fibroblast are between 50 and 70% confluence).

100 µl ECM+fibroblast are added to each well and this is incubated (37° C. for 2 Hours). Thereafter, 100 µl of E medium is added to the top of each collagen gel. 100 µl of E medium+RM TG* is then added to the bottom of each collagen gel. This is incubated (37° C. for 12-16 Hours).

A variety of collagen containing matrices are contemplated for making an artificial derma and ECM to embed fibroblasts:

Tropoelastin:Collagen I:Collagen III:Dermatan sulfate (1 mg:3 mg:3 mg:0.5 mg)
   Col I (3 mg/ml)/Elastin (3 mg/ml)
   Col I (3 mg/ml)/Elastin (1 mg/ml)
   Col I (10 mg/ml)/MaxGEL
   Col I (3 mg/ml)/Elastin (3 mg/ml) 1:1 MaxGel
   Col I (3 mg/ml)/Elastin (3 mg/ml)/Col III (3 mg/ml) 1:1:1 MaxGel
   Col I (10 mg/ml)/Elastin (10 mg/ml)

Additional embodiments are contemplated:

1. A device comprising i) a chamber, said chamber comprising a lumen, said lumen positioned under ii) a removable top and above iii) a porous membrane, said membrane positioned above one or more iv) fluidic channels.

2. The device of Claim 1, further comprising a gel matrix.

3. The device of Claim 2, further comprising parenchymal cells on or in the gel matrix, or both.

4. The device of Claim 3, wherein said parenchymal cells are selected from the group consisting of epithelial cells of the lung and epithelial cells of the skin.

5. The device of Claim 4, wherein said epithelial cells of the lung are selected from the group consisting of alveolar epithelial cells and airway epithelial cells.

6. The device of Claim 4, wherein said epithelial cells of the skin comprise keratinocytes.

7. The device of Claim 1, further comprising positioned on the bottom of the membrane so as to be in contact with the fluidic channels.

8. The device of Claim 7, wherein the endothelial cells are primary cells.

9. The device of Claim 8, wherein said primary cells are small vessel human dermal microvascular endothelial cells.

10. The device of Claim 8, wherein said primary cells are human umbilical vein endothelial cells.

11. The device of Claim 8, wherein said primary cells are bone marrow-derived endothelial progenitor cells.

12. The device of Claim 6, wherein said keratinocytes are epidermal keratinocytes.

13. The device of Claim 6, wherein said keratinocytes are human foreskin keratinocytes.

14. The device of Claim 1, wherein said device is a microfluidic device and said fluidic channels are microfluidic channels.

15. A device comprising i) a chamber, said chamber comprising a lumen, said lumen comprising ii) a gel matrix, said gel matrix comprising parenchymal cells, said gel matrix positioned above iii) a porous membrane, said membrane comprising endothelial cells in contact with iv) fluidic channels.

16. The device of Claim 15, wherein said parenchymal cells are selected from the group consisting of epithelial cells of the lung and epithelial cells of the skin.

17. The device of Claim 16, wherein said epithelial cells of the lung are selected from the group consisting of alveolar epithelial cells and airway epithelial cells.

18. The device of Claim 16, wherein said epithelial cells of the skin comprise keratinocytes.

19. The device of Claim 18, further comprising fibroblasts within the gel matrix, wherein the keratinocytes are on top of the gel matrix.

20. The device of Claim 19, wherein the keratinocytes comprise more than one layer on top of the gel matrix.

21. The device of Claim 15, wherein the endothelial cells are primary cells.

22. The device of Claim 21, wherein said primary cells are small vessel human dermal microvascular endothelial cells.

23. The device of Claim 21, wherein said primary cells are human umbilical vein endothelial cells.

24. The device of Claim 21, wherein said primary cells are bone marrow-derived endothelial progenitor cells.

25. The device of Claim 18, wherein said keratinocytes are epidermal keratinocytes.

26. The device of Claim 18, wherein said keratinocytes are human foreskin keratinocytes.

27. The device of Claim 15, further comprising an open region in contact with at least one of said gel, said membrane, said parenchymal cells or said endothelial cells.

28. A method of testing a drug, comprising 1) providing a) a candidate drug and b) device comprising i) a chamber, said chamber comprising a lumen, said lumen positioned above ii) a porous membrane, said membrane comprising parenchymal cells and positioned above one or more iii) fluidic channels; and 2) contacting said parenchymal cells with said candidate drug.

29. The method of Claim 28, wherein said parenchymal cells are selected from the group consisting of epithelial cells of the lung and epithelial cells of the skin.

30. The method of Claim 29, wherein said epithelial cells of the lung are selected from the group consisting of alveolar epithelial cells and airway epithelial cells.

31. The method of Claim 29, wherein said epithelial cells of the skin comprise keratinocytes.

32. The method of Claim 31, further comprising fibroblasts within the gel matrix, wherein the keratinocytes are on top of the gel matrix.

33. The method of Claim 28, wherein said chamber lacks a covering and said candidate drug is introduced into said lumen under conditions such that said parenchymal cells are contacted.

34. The method of Claim 28, wherein said candidate drug is in an aerosol.

35. The method of Claim 28, wherein said candidate drug is in a paste.

36. The method of Claim 28, wherein said device further comprises a removable top and said method further comprises, prior to step 2), removing said removable top.

37. A method of testing an agent comprising 1) providing a) an agent and b) microfluidic device comprising i) a chamber, said chamber comprising a lumen, said lumen comprising ii) a gel matrix comprising cells in, on or under said gel matrix, said gel matrix positioned above iii) a porous membrane and under iv) a removable cover, said membrane positioned above one or more v) fluidic channels; 2) removing said removable cover; and 3) contacting said cells in, on or under said gel matrix with said agent.

38. The method of Claim 37, wherein said agent is in an aerosol.

39. The method of Claim 37, wherein said agent is in a paste.

40. The method of Claim 37, wherein said agent is in a liquid, gas, gel, semi-solid, solid, or particulate form.

41. A device comprising i) a chamber, said chamber comprising a lumen and projections into the lumen, said lumen comprising ii) a gel matrix anchored by said projections, said gel matrix positioned above iii) a porous membrane, said membrane positioned above one or more iv) fluidic channels.

42. The device of Claim 41, wherein fibroblasts are within the gel matrix and keratinocytes are on top of the gel matrix.
43. The device of Claim 42, wherein the keratinocytes comprise more than one layer on top of the gel matrix.
44. The device of Claim 41, wherein a layer of endothelial cells is positioned on the bottom of the membrane so as to be in contact with the fluidic channels.
45. The device of Claim 44, wherein the endothelial cells are primary cells.
46. The device of Claim 45, wherein said primary cells are small vessel human dermal microvascular endothelial cells.
47. The device of Claim 45, wherein said primary cells are human umbilical vein endothelial cells.
48. The device of Claim 45, wherein said primary cells are bone marrow-derived endothelial progenitor cells.
49. The device of Claim 42, wherein said keratinocytes are epidermal keratinocytes.
50. The device of Claim 42, wherein said keratinocytes are human foreskin keratinocytes.
51. The device of Claim 41, further comprising a removable cover.
52. The device of Claim 41, wherein said device is a microfluidic device and said fluidic channels are microfluidic channels.
53. A microfluidic device comprising i) a chamber, said chamber comprising a lumen and projections into the lumen, said lumen comprising ii) a gel matrix anchored by said projections, said gel matrix comprising fibroblasts and keratinocytes, said gel matrix positioned above iii) a porous membrane, said membrane comprising endothelial cells in contact with iv) microfluidic channels.
54. The device of Claim 53, wherein the membrane is above said fluidic channels and wherein the layer of endothelial cells is positioned on the bottom of the membrane so as to be in contact with the fluidic channels.
55. The device of Claim 53, wherein the fibroblasts are within the gel matrix and the keratinocytes are on top of the gel matrix.
56. The device of Claim 55, wherein the keratinocytes comprise more than one layer on top of the gel matrix.
57. The device of Claim 53, wherein the endothelial cells are primary cells.
58. The device of Claim 57, wherein said primary cells are small vessel human dermal microvascular endothelial cells.
59. The device of Claim 57, wherein said primary cells are human umbilical vein endothelial cells.
60. The device of Claim 57, wherein said primary cells are bone marrow-derived endothelial progenitor cells.
61. The device of Claim 53, wherein said keratinocytes are epidermal keratinocytes.
62. The device of Claim 53, wherein said keratinocytes are human foreskin keratinocytes.
63. The device of Claim 53, wherein said matrix comprises collagen.
64. The device of Claim 53, wherein said collagen matrix is between 0.2 and 6 mm in thickness.
65. A method of testing a drug on keratinocytes, comprising 1) providing a) a candidate drug and b) microfluidic device comprising i) a chamber, said chamber comprising a lumen and projections into the lumen, said lumen comprising ii) a gel matrix anchored by said projections, said gel matrix comprising fibroblasts and keratinocytes, said gel matrix positioned above iii) a porous membrane, said membrane comprising endothelial cells in contact with iv) fluidic channels; and 2) contacting said keratinocytes with said candidate drug.
66. The method of Claim 28, wherein the fibroblasts are within the gel matrix and the keratinocytes are on top of the gel matrix.
67. The method of Claim 28, wherein said chamber lacks a covering and said candidate drug is introduced into said lumen under conditions such that said keratinocytes are contacted.
68. The method of Claim 28, wherein said candidate drug is in an aerosol.
69. The method of Claim 28, wherein said candidate drug is in a paste.
70. The method of Claim 28, wherein said microfluidic device further comprises a removable top and said method further comprises, prior to step 2), removing said removable top.
71. The method of Claim 28, wherein said microfluidic device further comprises an open region in contact with at least one of said gel matrix, said membrane, said keratinocytes or said endothelial cells.
72. A method of testing an agent comprising 1) providing a) an agent and b) microfluidic device comprising i) a chamber, said chamber comprising a lumen and projections into the lumen, said lumen comprising ii) a gel matrix anchored by said projections and comprising cells in, on or under said gel matrix, said gel matrix positioned above iii) a porous membrane and under iv) a removable cover, said membrane positioned above one or more v) fluidic channels; 2) removing said removable cover; and 3) contacting said cells in, on or under said gel matrix with said agent.
73. The method of Claim 72, wherein said agent is in an aerosol.
74. The method of Claim 72, wherein said agent is in a paste.
75. The method of Claim 72, wherein said agent is in a liquid, gas, gel, semi-solid, solid, or particulate form.

Still additional embodiments are contemplated:

28. A fluidic cover comprising a fluidic channel, said fluidic cover configured to engage a microfluidic device.
29. The fluidic cover of Claim 28, wherein said microfluidic device comprises an open chamber, and wherein said fluidic cover configured to cover and close said open chamber.
30. The fluidic cover of Claim 28, further comprising one or more electrodes.
31. An assembly comprising a fluidic cover comprising a fluidic channel, said fluidic cover detachably engaged with a microfluidic device.
32. The assembly of Claim 31, wherein said microfluidic device comprises an open chamber, and wherein said fluidic cover configured to cover and close said open chamber.
33. The assembly of Claim 32, wherein said open chamber comprises a non-linear lumen.
34. The assembly of Claim 33, wherein said non-linear lumen is circular.
35. The assembly of Claim 31, wherein said fluidic cover further comprises one or more electrodes.
36. A method of making an assembly, comprising: a) providing a fluidic cover comprising a fluidic channel, said fluidic cover configured to engage b) a microfluidic device, said microfluidic device comprises an open chamber, and wherein said fluidic cover configured to cover and close said open chamber; and b) detachably engaging said microfluidic device with said fluidic cover so as to make an assembly.
37. The method of making an assembly of Claim 36, wherein said open chamber comprises a non-linear lumen.

38. The method of making an assembly of Claim 37, wherein said non-linear lumen is circular.

39. The method of making an assembly of Claim 36, wherein said fluidic cover further comprises one or more electrodes.

The invention claimed is:

1. A method of using a microfluidic device for cell culture, comprising:
   a) providing an open-top microfluidic device comprising i) a chamber with a lumen and a fluidic cover comprising a microfluidic channel, ii) a porous membrane below said chamber wherein said fluidic cover is configured to detachably cover and close said chamber;
   b) seeding cells in said lumen without said fluidic cover covering said chamber; and
   c) detachably closing said chamber with said fluidic cover.

2. The method of claim 1, wherein said chamber further comprises a gel matrix.

3. The method of claim 1, further comprising the step of introducing fluid flow to said chamber after step c).

4. The method of claim 1, wherein said cells are epithelial cells.

5. The method of claim 4, further comprising the step of seeding endothelial cells.

6. The method of claim 1, wherein said chamber is circular.

7. A method for cell culture, comprising
   a) providing an open-top microfluidic device comprising i) a fluidic cover comprising a microfluidic channel, ii) a top structure comprising a chamber, said chamber comprising a lumen, and iii) a porous membrane layered below said chamber;
   b) detachably engaging said fluidic cover with said top structure such that said fluidic cover closes said chamber in said top structure, and such that said microfluidic channel is fluidically coupled to said chamber; and
   c) seeding cells in said lumen of said chamber after step a).

8. The method of claim 7, further comprising providing fluid flow to said microfluidic channel after step b).

9. The method of claim 7, wherein said fluidic channel is fluidically connected to a fluid input.

10. The method of claim 7, wherein said lumen comprises a gel matrix and said cells are seeded on or in said gel matrix.

11. The method of claim 10, extracting said gel matrix in whole or in part from the lumen.

12. The method of claim 11, further comprising staining the cells from the extracted gel matrix.

13. The method of claim 10, wherein said gel matrix comprises at least one of neurons and astrocytes.

* * * * *